United States Patent
Shin et al.

(10) Patent No.: US 12,037,599 B2
(45) Date of Patent: Jul. 16, 2024

(54) METHODS AND CONSTRUCTS FOR PRODUCTION OF LENTIVIRAL VECTOR

(71) Applicant: LONZA WALKERSVILLE, INC., Walkersville, MD (US)

(72) Inventors: Young Shin, Houston, TX (US); Anandita Seth, Houston, TX (US); Bingnan Gu, Houston, TX (US)

(73) Assignee: LONZA WALKERSVILLE, INC., Walkersville, MD (US)

( * ) Notice: Subject to any disclaimer, the term of this patent is extended or adjusted under 35 U.S.C. 154(b) by 675 days.

(21) Appl. No.: 17/001,114

(22) Filed: Aug. 24, 2020

(65) Prior Publication Data

US 2021/0062220 A1 Mar. 4, 2021

Related U.S. Application Data

(60) Provisional application No. 62/890,904, filed on Aug. 23, 2019.

(51) Int. Cl.
| | |
|---|---|
| C12N 15/867 | (2006.01) |
| C07K 14/16 | (2006.01) |
| C12N 5/071 | (2010.01) |
| C12N 9/12 | (2006.01) |
| C12N 15/86 | (2006.01) |

(52) U.S. Cl.
CPC .......... *C12N 15/867* (2013.01); *C07K 14/161* (2013.01); *C07K 14/162* (2013.01); *C07K 14/163* (2013.01); *C12N 5/0686* (2013.01); *C12N 9/1241* (2013.01); *C12N 15/8673* (2013.01); *C12N 15/8676* (2013.01); *C12N 15/86* (2013.01); *C12N 2740/15051* (2013.01); *C12N 2740/16052* (2013.01); *C12N 2760/20222* (2013.01)

(58) Field of Classification Search
CPC .. C12N 15/867; C07K 14/161; C07K 14/162; C07K 14/163
See application file for complete search history.

(56) References Cited

U.S. PATENT DOCUMENTS

| | | | |
|---|---|---|---|
| 7,262,049 B2 * | 8/2007 | Marasco | ................. C40B 40/02 536/23.1 |
| 7,745,179 B2 | 6/2010 | McArthur et al. | |
| 9,169,491 B2 | 10/2015 | Truran et al. | |
| 9,441,245 B2 | 9/2016 | Chiara et al. | |
| 10,087,463 B2 | 10/2018 | Fraser et al. | |
| 10,125,352 B2 | 11/2018 | Fenard | |
| 10,465,169 B2 | 11/2019 | Boudeffa et al. | |
| 10,699,284 B2 | 6/2020 | Sheth et al. | |
| 2009/0042297 A1 * | 2/2009 | George, Jr. | ........ C12N 15/8509 536/23.2 |
| 2016/0267432 A1 | 9/2016 | Hodges | |
| 2016/0350715 A1 | 12/2016 | Minvielle | |
| 2017/0051309 A1 | 2/2017 | Lesch et al. | |
| 2017/0368201 A1 | 12/2017 | Gu et al. | |
| 2018/0320147 A1 | 11/2018 | Johnson et al. | |
| 2019/0055568 A1 | 2/2019 | Pule et al. | |
| 2019/0093126 A1 | 3/2019 | High et al. | |
| 2019/0180289 A1 | 6/2019 | Klavins | |
| 2019/0211360 A1 | 7/2019 | Marceau et al. | |
| 2020/0123505 A1 | 4/2020 | Johnson et al. | |
| 2020/0157567 A1 | 5/2020 | Cawood et al. | |
| 2020/0208121 A1 | 7/2020 | Hewitt et al. | |
| 2020/0277629 A1 | 9/2020 | Cawood et al. | |

FOREIGN PATENT DOCUMENTS

| | | |
|---|---|---|
| EP | 3456822 A1 | 3/2019 |
| WO | 2011/097447 A3 | 8/2011 |
| WO | 2017/144893 A1 | 8/2017 |

OTHER PUBLICATIONS

Heinz, N., et al., Feb. 2011, Retroviral and Transposon-Based Tet-Regulated All-In-One Vector with Reduced Background Expression and Improved Dynamic Range, Human Gene Therapy 22:166-176.*
Cary et al., "Transposon mutagenesis of baculoviruses: Analysis of *Trichoplusia ni* transposon IFP2 insertions within the FP-locus of nuclear polyhedrosis viruses," Virology (1989) 172(1):156-169.
Chu et al., "SV40 DNA transfection of cells in suspension: analysis of the efficiency of transcription and translation of T-antigen," Gene (1981) 13(2):197-202.
Elick et al., "Excision of the piggyBac transposable element in vitro is a precise event that is enhanced by the expression of its encoded transposase," Genetica (1996) 98(1):33-41.
Elick et al., "PCR analysis of insertion site specificity, transcription, and structural uniformity of the Lepidopteran transposable element IFP2 in the TN-368 cell genome," Genetica (1996) 97(2):127-139.
Fraser et al., "Acquisition of Host Cell DNA Sequences by Baculoviruses: Relationship Between Host DNA Insertions and FP Mutants of *Autographa californica* and *Galleria mellonella* Nuclear Polyhedrosis Viruses," Journal of Virology (1983) 47(2):287-300.
Fraser et al., "Assay for Movement of Lepidopteran Transposon IFP2 in Insect Cells Using a Baculovirus Genome as a Target DNA," Virology (1995) 211(2):397-407.

(Continued)

*Primary Examiner* — Jeffrey S Parkin
(74) *Attorney, Agent, or Firm* — MEDLER FERRO WOODHOUSE & MILLS PLLC

(57) ABSTRACT

The present disclosure relates to methods for producing lentiviral vector-producing cells. Specifically the methods utilize two plasmids, rather than four, to provide the required packaging elements and transfer vector to a cell, allowing for the production of a large number of lentiviral producer cells, including suspension-based cells, and the production of high amounts of lentivirus. These methods allow for the production of cells that can be later induced to produce lentivirus, and can be tailored to include a specific gene of interest.

14 Claims, 10 Drawing Sheets

Specification includes a Sequence Listing.

(56) References Cited

OTHER PUBLICATIONS

Fraser et al., "Precise excision of TTAA-specific lepidopteran transposons piggyBac (IFP2) and tagalong (TFP3) from the baculovirus genome in cell lines from two species of *Lepidoptera*," Insect Molecular Biology (1996) 5(2):141-151.

Graham et al., "A new technique for the assay of infectivity of human adenovirus 5 DNA," Virology (1973) 52(2):456-467.

Handler et al., "The lepidopteran transposon vector, piggyBac, mediates germ-line transformation in the Mediterranean fruit fly," Proc. Natl. Acad. Sci. USA (1998) 95(13):7520-7525.

Hellmund et al., "Coordination of Genomic RNA Packaging with Viral Assembly in HIV-1," Viruses (2016) 8(192):1-13.

Lobo et al., "Transposition of the piggyBac element in embryos of *Drosophila melanogaster, Aedes aegypti* and *Trichoplusia ni*," Molecular and General Genetics (1999) 261(4-5):803-810.

Merten et al., "Production of lentiviral vectors," Molecular Therapy—Methods & Clinical Development (2016) 3:16017.

Mullick et al., "The cumate gene-switch: a system for regulated expression in mammalian cells," BMC Biotechnology (2006) 6(43):1-18.

Wang et al., "TTAA serves as the target site for TFP3 lepidopteran transposon insertions in both nuclear polyhedrosis virus and *Trichoplusia ni* genomes," Insect Molecular Biology (1993) 1(3):109-116.

Yao et al., "Tetracycline Repressor, tetR, rather than the tetR-Mammalian Cell Transcription Factor Fusion Derivatives, Regulates Inducible Gene Expression in Mammalian Cells," Human Gene Therapy (1998) 9(13):1939-1950.

Gil, Alberto Molina. (2017). Lentiviral vector packaging cell line development using genome editing to target optimal loci discovered by high- throughput DNA barcoding [Doctoral thesis, Institution University College London].

\* cited by examiner

SEQUENCE LISTING

<160> NUMBER OF SEQ ID NOS: 2

<210> SEQ ID NO 1
<211> LENGTH: 19385
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
atgagtattc aacatttccg tgtcgccctt attccctttt ttgcggcatt ttgccttcct        60 gttttgctc  acccagaaac gctggtgaaa gtaaaagatg ctgaagatca gttgggtgca       120
cgagtgggtt acatcgaact ggatctcaac agcggtaaga tccttgagag ttttcgcccc       180
gaagaacgtt ttccaatgat gagcactttt aaagttctgc tatgtggcgc ggtattatcc       240
cgtattgacg ccgggcaaga gcaactcggt cgccgcatac actattctca gaatgacttg       300
gttgagtact caccagtcac agaaaagcat cttacggatg gcatgacagt aagagaatta       360
tgcagtgctg ccataaccat gagtgataac actgcggcca acttacttct gacaacgatc       420
```

-continued

```
ggaggaccga aggagctaac cgcttttttg cacaacatgg gggatcatgt aactcgcctt      480
gatcgttggg aaccggagct gaatgaagcc ataccaaacg acgagcgtga caccacgatg      540
cctgtagcaa tggcaacaac gttgcgcaaa ctattaactg gcgaactact tactctagct      600
tcccggcaac aattaataga ctggatggag gcggataaag ttgcaggacc acttctgcgc      660
tcggcccttc cggctggctg gtttattgct gataaatctg gagccggtga gcgtgggtct      720
cgcggtatca ttgcagcact ggggccagat ggtaagccct cccgtatcgt agttatctac      780
acgacgggga gtcaggcaac tatggatgaa cgaaatagac agatcgctga gataggtgcc      840
tcactgatta agcattggta actgtcagac caagtttact catatatact ttagattgat      900
ttaaaacttc attttttaatt taaaaggatc taggtgaaga tcctttttga taatctcatg      960
accaaaatcc cttaacgtga gttttcgttc cactgagcgt cagacccccgt agaaaagatc     1020 aaaggatctt cttgagatcc ttttttttctg cgcgtaatct gctgcttgca acaaaaaaa     1080 ccaccgctac cagcggtggt ttgtttgccg gatcaagagc taccaactct ttttccgaag     1140
gtaactggct tcagcagagc gcagatacca atactgtcc ttctagtgta gccgtagtta      1200
ggccaccact tcaagaactc tgtagcaccg cctacatacc tcgctctgct aatcctgtta     1260
ccagtggctg ctgccagtgg cgataagtcg tgtcttaccg ggttggactc aagacgatag     1320
ttaccggata aggcgcagcg tcgggctga acggggggtt cgtgcacaca gcccagcttg     1380
gagcgaacga cctacaccga actgagatac ctacagcgtg agctatgaga aagcgccacg     1440
cttcccgaag ggagaaaggc ggacaggtat ccggtaagcg gcagggtcgg aacaggagag     1500
cgcacgaggg agcttccagg gggaaacgcc tggtatcttt atagtcctgt cgggtttcgc     1560
cacctctgac ttgagcgtcg attttttgtga tgctcgtcag ggggggcgag cctatggaaa     1620
aacgccagca acgcggcctt tttacggttc ctggccttttt gctggccttt tgctcacatg     1680
ttctttcctg cgttatcccc tgattctgtg ataaccgta ttaccgcctt tgagtgagct      1740
gataccgctc gccgcagccg aacgaccgag cgcagcgagt cagtgagcga ggaagcggaa     1800
gagcgcccaa tacgcaaacc gcctctcccc gcgcgttggc cgattcatta atgcagctgg     1860
cacgacaggt ttcccgactg gaaagcgggc agtgagcgca acgcaattaa tgtgagttag     1920
ctcactcatt aggcaccccca ggctttacac tttatgcttc cggctcgtat gttgtgtgga     1980
attgtgagcg gataacaatt tcacacagga aacagctatg accatgatta cgccaagcgc     2040
gcccgccggg taactcacgg ggtatccatg tccatttctg cggcatccag ccaggatacc     2100
cgtcctcgct gacgtaatat cccagcgccg caccgctgtc attaatctgc acaccggcac     2160
ggcagttccg gctgtcgccg gtattgttcg ggttgctgat gcgcttcggg ctgaccatcc     2220
ggaactgtgt ccgaaaagc gcgacgaac tggtatccca ggtggcctga acgaacagtt     2280
caccgttaaa ggcgtgcatg gccacacctt cccgaatcat catggtaaac gtgcgttttc     2340
gctcaacgtc aatgcagcag cagtcatcct cggcaaactc tttccatgcc gcttcaacct     2400
cgcgggaaaa ggcacgggct tcttcctccc cgatgcccag atagcgccag cttgggcgat     2460
gactgagccg gaaaaaagac ccgacgatat gatcctgatg cagctagatt aaccctagaa     2520
agatagtctg cgtaaaattg acgcatgcat tcttgaaata ttgctctctc tttctaaata     2580
gcgcgaatcc gtcgctgtgc atttaggaca tctcagtcgc cgcttggagc tcccgtgagg     2640
cgtgcttgtc aatgcggtaa gtgtcactga ttttgaacta taacgaccgc gtgagtcaaa     2700
atgacgcatg attatctttt acgtgacttt taagatttaa ctcatacgat aattatattg     2760
```

-continued

```
ttatttcatg ttctacttac gtgataactt attatatata tattttcttg ttatagatat    2820
caagcttatc gataccgtcg acctcgaggg ggggcccggt acccaattcg ccctatagtg    2880
agtcgtatta agatctaatt aaccctcact aaagggaaca aaagctggag ctccaccgcg    2940
gtggcggccg ctctagaggg acagcccccc cccaaagccc ccagggatgt aattacgtcc    3000
ctcccccgct aggggcagc agcgagccgc ccggggctcc gctccggtcc ggcgctcccc      3060
ccgcatcccc gagccggcag cgtgcgggga cagcccgggc acggggaagg tggcacggga    3120
tcgctttcct ctgaacgctt ctcgctgctc tttgagcctg cagacacctg gggggatacg    3180
gggaaaaagc cataccaatg ggccctaaaa aaggaatcca gtcaattccg ggctaaaacc    3240
tggctgccac tgtttctttta gggacttcgt tcctgtgagg acacctgcag gccggccgga   3300
tcctaggtat acgcgttaat taaagcttgt taacgacatt gattattgac tagttattaa    3360
tagtaatcaa ttacggggtc attagttcat agcccatata tggagttccg cgttacataa    3420
cttacggtaa atggcccgcc tggctgaccg cccaacgacc cccgcccatt gacgtcaata    3480
atgacgtatg ttcccatagt aacgccaata gggactttcc attgacgtca atgggtggag    3540
tatttacggt aaactgccca cttggcagta catcaagtgt atcatatgcc aagtacgccc    3600
cctattgacg tcaatgacgg taaatggccc gcctggcatt atgcccagta catgacctta    3660
tgggactttc ctacttggca gtacatctac gtattagtca tcgctattac catggtgatg    3720
cggttttggc agtacatcaa tgggcgtgga tagcggtttg actcacgggg atttccaagt    3780
ctccacccca ttgacgtcaa tgggagtttg ttttggaacc aaaatcaacg ggactttcca    3840
aaatgtcgta acaactccgc cccattgacg caaatgggcg gtaggcgtgt acggtgggag    3900
gtctatataa gcagagctct ccctatcagt gatagagatc tccctatcag tgatagagat    3960
cgtcgacgag gtgagtttgg ggacccttga ttgttctttc ttttcgcta ttgtaaaatt      4020 catgttatat ggaggggca aagttttcag ggtgttgttt agaatgggaa gatgtccctt     4080
gtatcaccat ggaccctcat gataattttg tttctttcac tttctactct gttgacaacc    4140
attgtctcct cttattttct tttcatttttc tgtaactttt tcgttaaact ttagcttgca    4200
tttgtaacga atttttaaat tcacttttgt ttatttgtca gattgtaagt actttctcta    4260
atcacttttt tttcaaggca atcagggtat attatattgt acttcagcac agttttagag    4320
aacaattgtt ataattaaat gataaggtag aatatttctg catataaatt ctggctggcg    4380
tggaaatatt cttattggta gaaacaacta catcctggtc atcatcctgc ctttctcttt    4440
atggttacaa tgtatacac tgtttgagat gaggataaaa tactctgagt ccaaaccggg      4500
cccctctgct aaccatgttc atgccttctt cttttttccta cagagacgcc atccacgctg    4560 ttttgaccctc ctgccaccat ggctggaaga tctggcgact ctgacgagga cctgctgaaa   4620
gctgtgcggc tgatcaagtt cctgtaccag agcaaccctc cacctaatcc tgagggcacc    4680
agacaggcca gaagaaacag gcggagaaga tggcgcgagc ggcagagaca gatccactcc    4740
atctccgagc ggatcctgtc cacctacctg gaagatccg ctgagcctgt tcctctgcag      4800
ctgcctcctc tggaaagact gaccctggac tgcaacgagg actgcggcac ctctggaaca    4860
caaggcgttg ctctccaca gatcctggtg gaaagcccca ccatcctgga atccggcgcc     4920
aaagaatgag tttaaaccgc tgatcagcct cgactgtgcc ttctagttgc cagccatctg    4980
ttgtttgccc ctcccccgtg ccttccttga ccctggaagg tgccactccc actgtccttt    5040
cctaataaaa tgaggaaatt gcatcgcatt gtctgagtag gtgtcattct attctggggg    5100
gtggggtggg gcaggacagc aagggggagg attgggaaga caatagcagg catgctgggg    5160
```

```
atgcggtggg ctctatggta ccacagattc ccgcttctcg actaattcct cttgtacgtg   5220
tacttcgaca tgtacctccc gtggcacttg ttggtggtga agttcacgtg taggctcccg   5280
cttccgttcg ggatgctccc gtgggtctgg tactcttagt tccaccagct cccgccggga   5340
gaggggaagc ggaagctgta ggaccgatgg tcgaagtaga cattgattat tgactagtta   5400
ttaatagtaa tcaattacgg ggtcattagt tcatagccca tatatggagt tccgcgttac   5460
ataacttacg gtaaatggcc cgcctggctg accgcccaac gacccccgcc cattgacgtc   5520
aataatgacg tatgttccca tagtaacgcc aatagggact ttccattgac gtcaatgggt   5580
ggagtattta cggtaaactg cccacttggc agtacatcaa gtgtatcata tgccaagtac   5640
gccccctatt gacgtcaatg acggtaaatg gcccgcctgg cattatgccc agtacatgac   5700
cttatgggac tttcctactt ggcagtacat ctacgtatta gtcatcgcta ttaccatggt   5760
gatgcggttt tggcagtaca tcaatgggcg tggatagcgg tttgactcac ggggatttcc   5820
aagtctccac cccattgacg tcaatgggag tttgttttgg aaccaaaatc aacgggactt   5880
tccaaaatgt cgtaacaact ccgccccatt gacgcaaatg ggcggtaggc gtgtacggtg   5940
ggaggtctat ataagcagag ctctccctat cagtgataga gatctcccta tcagtgatag   6000
agatcgtcga cgaggtaagt atcaaggtta caagacaggt ttaaggagac aatagaaac   6060 tgggcttgtc gagacagaga agactcttgc gtttctgata ggcacctatt ggtcttactg   6120
acatccactt tgcctttctc tccacaggcg ccgcgacac tgccaccatg aagtgcctgc   6180
tgtacctggc ctttctgttc atcggcgtga actgtaagtt taccatcgtg ttccctcaca   6240
atcagaaggg caactggaag aatgtgccaa gcaactacca ctattgcccc agctcctctg   6300
acctgaactg gcacaatgat ctgatcggca cagccctgca ggtgaagatg ccaaagagcc   6360
acaaggccat ccaggcagac ggatggatgt gccacgcctc caagtgggtg accacatgtg   6420
attttcggtg gtacggccca agtatatca cccacagcat cagatccttc acaccctctg   6480
tggagcagtg caaggagagc atcgagcaga caaagcaggg cacctggctg aatcctggct   6540
ttccccctca gtcctgtgga tacgcaacag tgaccgacgc agaggccgtg atcgtgcagg   6600
tgaccccaca ccacgtgctg gtggacgagt atacaggcga gtgggtggat cccagttca   6660 tcaacggcaa gtgctctaat tacatctgtc ccaccgtgca caactccacc acatggcact   6720
ctgattataa ggtgaagggc ctgtgcgatt ctaatctgat cagcatggac atcacattct   6780
tttctgagga tggagagctg agctccctgg gcaaggaggg aaccggcttt cggagcaact   6840
acttcgccta tgagacaggc ggcaaggcct gcaagatgca gtactgtaag cactggggcg   6900
tgaggctgcc aagcggcgtg tggttcgaga tggccgacaa ggatctgttt gctgccgcca   6960
ggttcccaga gtgcccagag ggatctagca tctctgcccc aagccagacc tccgtggacg   7020
tgtccctgat ccaggatgtg agcggatcc tggactactc cctgtgccag agacatggt   7080 ctaagatcag agccggcctg cctatcagcc agtggacct gtcctatctg caccaaaga   7140 accctggaac aggaccagcc tttaccatca tcaatggcac actgaagtac ttcgagaccc   7200
ggtatatcag agtggacatc gccgccccta tcctgagcag gatggtgggc atgatctccg   7260
gaaccacaac cgagagggag ctgtgggacg attgggcacc ttacgaggat gtggagatcg   7320
gcccaaatgg cgtgctgcgg acctcctctg ctacaagtt tccctgtat atgatcggcc   7380 acggcatgct ggacagcgat ctgcacctga gctccaaggc ccaggtgttc gagcacccac   7440
acatccagga cgcagcatct cagctgcctg acgatgagag cctgttcttt ggcgataccg   7500
```

```
gcctgtccaa gaaccctatc gagctggtgg agggctggtt ttctagctgg aagtcctcta    7560
tcgcctcttt cttttcatc atcggcctga tcatcggcct gttcctggtg ctgagagtgg    7620
gcatccacct gtgcatcaag ctgaagcaca ccaagaagag gcagatctat acagacatcg    7680
agatgaatcg cctgggcaag tgatctagac tcgagcggcc gccactgtgc tggatatctg    7740
cagaattcca ccacactgga ctagtggatc cgagctcggt accaagctta agtttaaacc    7800
gctgatcagc ctcgactgtg ccttctagtt gccagccatc tgttgtttgc cctcccccg    7860 tgccttcctt gaccctggaa ggtgccactc ccactgtcct ttcctaataa aatgaggaaa    7920
ttgcatcgca ttgtctgagt aggtgtcatt ctattctggg gggtggggtg gggcaggaca    7980
gcaaggggga ggattgggaa gacaatagca ggcatgctgg ggatgcggtg ggctctatgg    8040
catgccgtcg tcttggaagt agttggtgtg ggtcccgtag gggctgaaga aattcgtcag    8100
gaagggactc ccgaagtgta ccctctctca gtggtgtatg cttctgcccc cgcacgactg    8160
gcgatgggtc ctgtggtcgg aggtcctgcc gacggagtag atgttgcagt tctagtctcc    8220
ccacttgaag ggtaggttgc gacattgatt attgactagt tattaatagt aatcaattac    8280
ggggtcatta gttcatagcc catatatgga gttccgcgtt acataactta cggtaaatgg    8340
cccgcctggc tgaccgccca acgaccccgc ccattgacg tcaataatga cgtatgttcc    8400
catagtaacg ccaataggga cttccattg acgtcaatgg gtggagtatt tacggtaaac    8460
tgcccacttg gcagtacatc aagtgtatca tatgccaagt acgccccta ttgacgtcaa    8520 tgacggtaaa tggcccgcct ggcattatgc ccagtacatg accttatggg actttcctac    8580
ttggcagtac atctacgtat tagtcatcgc tattaccatg gtgatgcggt tttggcagta    8640
catcaatggg cgtggatagc ggtttgactc acggggattt ccaagtctcc accccattga    8700
cgtcaatggg agtttgtttt ggaaccaaaa tcaacgggac tttccaaaat gtcgtaacaa    8760
ctccgcccca ttgacgcaaa tgggcggtag gcgtgtacgg tgggaggtct atataagcag    8820
agctctccct atcagtgata gagatctccc tatcagtgat agagatcgtc gacgaggtaa    8880
gtatcaaggt tacaagacag gtttaaggag accaatagaa actgggcttg tcgagacaga    8940
gaagactctt gcgtttctga taggcaccta ttggtcttac tgacatccac tttgcctttc    9000
tctccacagg tgtccactcc cagttcaatt acagctctta aggctagagt acttaatacg    9060
actcactata ggctagcctc gagaattcac gcgcacggca agaggcgagg ggcggcgact    9120
ggtgagtacg ccaggatccg cggatccatg gccgcccgcg ccagcgtgct gtccggcggc    9180
gagctggata atgggaaaa aattcggtta aggccagggg gaaagaaaca atataaacta    9240
aaacatatag tatgggcaag cagggagcta gaacgattcg cagttaatcc tggccttta    9300 gagacatcag aaggctgtag acaaatactg ggacagctac aaccatccct tcagacagga    9360
tcagaagaac ttagatcatt atataataca atagcagtcc tctattgtgt gcatcaaagg    9420
atagatgtaa aagacaccaa ggaagcctta gataagatag aggaagagca aaacaaaagt    9480
aagaaaaagg cacagcaagc agcagctgac acaggaaaca acagccaggt cagccaaaat    9540
taccctatag tgcagaacct ccaggggcaa atggtacatc aggccatatc acctagaact    9600
ttaaatgcat gggtaaaagt agtagaagag aaggctttca gcccagaagt aatacccatg    9660
ttttcagcat tatcagaagg agccaccccca caagatttaa ataccatgct aaacacagtg    9720
gggggacatc aagcagccat gcaaatgtta aaagagacca tcaatgagga agctgcagaa    9780
tgggatagat tgcatccagt gcatgcaggg cctattgcac caggccagat gagagaacca    9840
aggggaagtg acatagcagg aactactagt acccttcagg aacaaatagg atggatgaca    9900
```

```
cataatccac ctatcccagt aggagaaatc tataaaagat ggataatcct gggattaaat    9960
aaaatagtaa gaatgtatag ccctaccagc attctggaca taagacaagg accaaaggaa   10020 cccttttagag actatgtaga ccgattctat aaaactctaa gagccgagca agcttcacaa   10080
gaggtaaaaa attggatgac agaaaccttg ttggtccaaa atgcgaaccc agattgtaag   10140
actattttaa aagcattggg accaggagcg acactagaag aaatgatgac agcatgtcag   10200
ggagtggggg gacccggcca taaagcaaga gttttggctg aagcaatgag ccaagtaaca   10260
aatccagcta ccataatgat acagaaaggc aattttagga accaaagaaa gactgttaag   10320
tgtttcaatt gtggcaaaga agggcacata gccaaaaatt gcagggcccc taggaaaaag   10380
ggctgttgga aatgtggaaa ggaaggacac caaatgaaag attgtactga gagacaggct   10440
aattttttag ggaagatctg gccttcccac aagggaaggc cagggaattt tcttcagagc   10500
agaccagagc caacagcccc accagaagag agcttcaggt ttggggaaga gacaacaact   10560
ccctctcaga agcaggagcc gatagacaag gaactgtatc ctttagcttc cctcagatca   10620
ctctttggca gcgacccctc gtcacaataa agatagggg gcaattaaag gaagctctat   10680
tagatacagg agcagatgat acagtattag aagaaatgaa tttgccagga agatggaaac   10740
caaaaatgat agggggaatt ggaggtttta tcaaagtaag acagtatgat cagatactca   10800
tagaaatctg cggacataaa gctataggta cagtattagt aggacctaca cctgtcaaca   10860
taattggaag aaatctgttg actcagattg gctgcacttt aaattttccc attagtccta   10920
ttgagactgt accagtaaaa ttaaagccag gaatggatgg cccaaaagtt aaacaatggc   10980
cattgacaga agaaaaaata aaagcattag tagaaatttg tacagaaatg gaaaggaag   11040 gaaaaatttc aaaaattggg cctgaaaatc catacaatac tccagtatttt gccataaaga   11100 aaaagacag tactaaatgg agaaaattag tagatttcag agaacttaat aagagaactc   11160
aagatttctg ggaagttcaa ttaggaatac cacatcctgc agggttaaaa cagaaaaaat   11220
cagtaacagt actggatgtg ggcgatgcat attttttcagt tcccttagat aaagacttca   11280
ggaagtatac tgcatttacc atacctagta taaacaatga gacaccaggg attagatatc   11340
agtacaatgt gcttccacag ggatggaaag gatcaccagc aatattccag tgtagcatga   11400
caaaaatctt agagcctttt agaaaacaaa atccagacat agtcatctat caatacatgg   11460
atgatttgta tgtaggatct gacttagaaa tagggcagca tagaacaaaa atagaggaac   11520
tgagacaaca tctgttgagg tggggattta ccacaccaga caaaaaacat cagaaagaac   11580
ctccattcct ttgatgggt tatgaactcc atcctgataa atggacagta cagcctatag   11640
tgctgccaga aaaggacagc tggactgtca atgacataca gaattagtg ggaaaattga   11700 attgggcaag tcagatttat gcagggatta agtaaggca attatgtaaa cttcttaggg   11760
gaaccaaagc actaacagaa gtagtaccac taacagaaga agcagagcta gaactggcag   11820
aaaacaggga gattctaaaa gaaccggtac atggagtgta ttatgaccca tcaaaagact   11880
taatagcaga aatacagaag caggggcaag gccaatggac atatcaaatt tatcaagagc   11940
catttaaaaa tctgaaaaca ggaaagtatg caagaatgaa gggtgcccac actaatgatg   12000
tgaaacaatt aacagaggca gtacaaaaaa tagccacaga aagcatagta atatggggaa   12060
agactcctaa atttaaatta cccatacaaa aggaaacatg gaagcatgg tggacagagt   12120 attggcaagc cacctggatt cctgagtggg agtttgtcaa tacccctccc ttagtgaagt   12180
tatggtacca gttagagaaa gaacccataa taggagcaga aactttctat gtagatgggg   12240
```

-continued

```
cagccaatag ggaaactaaa ttaggaaaag caggatatgt aactgacaga ggaagacaaa    12300
aagttgtccc cctaacggac acaacaaatc agaagactga gttacaagca attcatctag    12360
ctttgcagga ttcgggatta gaagtaaaca tagtgacaga ctcacaatat gcattgggaa    12420
tcattcaagc acaaccagat aagagtgaat cagagttagt cagtcaaata atagagcagt    12480
taataaaaaa ggaaaaagtc tacctggcat gggtaccagc acacaaagga attggaggaa    12540
atgaacaagt agataaattg gtcagtgctg gaatcaggaa agtactattt ttagatggaa    12600
tagataaggc ccaagaagaa catgagaaat atcacagtaa ttggagagca atggctagtg    12660
attttaacct accacctgta gtagcaaaag aaatagtagc cagctgtgat aaatgtcagc    12720
taaaagggga agccatgcat ggacaagtag actgtagccc aggaatatgg cagctagatt    12780
gtacacattt agaaggaaaa gttatcttgg tagcagttca tgtagccagt ggatatatag    12840
aagcagaagt aattccagca gagacagggc aagaaacagc atacttcctc ttaaaattag    12900
caggaagatg gccagtaaaa acagtacata cagacaatgg cagcaatttc accagtacta    12960
cagttaaggc cgcctgttgg tgggcgggga tcaagcagga atttggcatt ccctacaatc    13020
cccaaagtca aggagtaata gaatctatga ataaagaatt aaagaaaatt ataggacagg    13080
taagagatca ggctgaacat cttaagacag cagtacaaat ggcagtattc atccacaatt    13140
ttaaaagaaa agggggggatt ggggggtaca gtgcagggga agaatagta gacataatag    13200 caacagacat acaaactaaa gaattacaaa acaaattac aaaaattcaa aattttcggg    13260
tttattacag ggacagcaga gatccagttt ggaaaggacc agcaaagctc ctctggaaag    13320
gtgaaggggc agtagtaata caagataata gtgacataaa agtagtgcca agaagaaaag    13380
caaagatcat cagggattat ggaaaacaga tggcaggtga tgattgtgtg caagtagac    13440 aggatgagga ttaacaccca tagaatggcc aaggcaaaga gaagtggt gcagagaaa    13500 aaaagagcag tgggaatagg agctttgttc cttgggttct tgggagcagc aggaagcact    13560
atgggcgcag cgtcaatgac gctgacggta caggccagac aattattgtc tgatatagtg    13620
cagcagcaga acaatttgct gagggctatt gaggcgcaac agcatctgtt gcaactcaca    13680
gtctggggca tcaaacagct ccaggcaaga atcctggctg tggaaagata cctaaaggat    13740
caacagctcc tggggatttg gggttgctct ggaaaactca tttgcaccac tgctgtgccg    13800
cggccgcaaa aaggggctc gtccctgttt ccggaggaat ttgcaagcgg gtcttgcat    13860 gacggggagg caaacccccg ttcggccgca gtccggccgg cccgagactc gaaccggggg    13920
tcctgcgact caacccttgg aaaataaccc tccggctaca gggagcgagc cacttaatgc    13980
tttcgctttc cagcctaacc gcttacgccg cgcgcggcca gtggccaaaa aagctagcgc    14040
agcagccgcc gcgcctggaa ggaagccaaa aggagcgctc ccccgttgtc tgacgtcgca    14100
cacctgggtt cgacacgcgg gcggtaaccg catggatcac ggcggacggc cggatccggg    14160
gttcgaaccc cggtcgtccg ccatgatacc cttgcgaatt tatccaccag accacgaag    14220 agtgcccgcg gccgcttcga gcagacatga taagatacat tgatgagttt ggacaaacca    14280
caactagaat gcagtgaaaa aaatgcttta tttgtgaaat ttgtgatgct attgctttat    14340
ttgtaaccat tataagctgc aataaacaag ttcgggacac tacgtcttct tttgtgagcc    14400
gaccctccgg ttgtggctct acgacatggg gcgactgccg ccggaccttc cgtcttcgct    14460
gtaccgggac ttcgagcacc cgccccggt ggactagacg ttgaagttct ggtgtatgtc    14520
taggttcttt gggcgattct tggagttcta cgggccgcag atgatacacc tggggggttgg    14580 ggttgcgcct tttccaaggc agccctgggt ttgcgcaggg acgcggctgc tctgggcgtg    14640
```

```
gttccgggaa acgcagcggc gccgaccctg ggtctcgcac attcttcacg tccgttcgca   14700
gcgtcacccg gatcttcgcc gctacccttg tgggccccccc ggcgacgctt cctgctccgc   14760
ccctaagtcg ggaaggttcc ttgcggttcg cggcgtgccg gacgtgacaa acggaagccg   14820
cacgtctcac tagtaccctc gcagacggac agcgccaggg agcaatggca gcgcgccgac   14880
cgcgatgggc tgtggccaat agcggctgct cagcagggcg cgccgagagc agcggccggg   14940
aaggggcggt gcgggaggcg gggtgtgggg cggtagtgtg ggccctgttc ctgcccgcgc   15000
ggtgttccgc attctgcaag cctccggagc gcacgtcggc agtcggctcc ctcgttgacc   15060
gaatcaccga cctctctccc cagggggatc tgtaagtatc aaggttacaa gacaggttta   15120
aggagaccaa tagaaactgg gcttgtcgag acagagaaga ctcttgcgtt tctgataggc   15180
acctattggt cttactgaca tccactttgc ctttctctcc acagctcctg gcaacgtgc    15240 tggttattgt gctgtctcat cattttggca agaattgta atacgactca ctatagggcg    15300
agccaccatg gctagattag ataaaagtaa agtgattaac agcgcattag agctgcttaa    15360
tgaggtcgga atcgaaggtt taacaacccg taaactcgcc cagaagctag gtgtagagca    15420
gcctacattg tattggcatg taaaaaataa gcgggctttg ctcgacgcct tagccattga    15480
gatgttagat aggcaccata ctcactttg ccctttagaa ggggaaagct ggcaagattt     15540
tttacgtaat aacgctaaaa gttttagatg tgctttacta agtcatcgcg atggagcaaa    15600
agtacattta ggtacacggc ctacagaaaa acagtatgaa actctcgaaa atcaattagc    15660
ctttttatgc caacaaggtt tttcactaga gaatgcctta tatgcactca gcgccgtggg    15720
gcattttact ttaggttgcg tattggaaga tcaagagcat caagtcgcta agaagaaag    15780 ggaaacacct actactgata gtatgccgcc attattacga caagctatcg aattatttga    15840
tcaccaaggt gcagagccag ccttcttatt cggccttgaa ttgatcatat gcggattaga    15900
aaaacaactt aaatgtgaaa gtgggtcccc aaaaaagaag agaaaggtcg acggcggtgg    15960
tgctttgtct cctcagcact ctgctgtcac tcaaggaagt atcatcaaga acaaggaggg    16020
catggatgct aagtcactaa ctgcctggtc ccggacactg gtgaccttca aggatgtatt    16080
tgtggacttc accagggagg agtggaagct gctggacact gctcagcaga tcgtgtacag    16140
aaatgtgatg ctggagaact ataagaacct ggtttccttg ggttatcagc ttactaagcc    16200
agatgtgatc ctccggttgg agaagggaga agagccctgg ctggtggaga gagaaattca    16260
ccaagagacc catcctgatt cagagactgc atttgaaatc aaatcatcag tttaagcgta    16320
cagcggctcc cgggagttct agggatctgc ccctctccct ccccccccccc taacgttact    16380 ggccgaagcc gcttggaata aggccggtgt gcgtttgtct atatgttatt ttccaccata    16440
ttgccgtctt ttggcaatgt gagggcccgg aaacctggcc ctgtcttctt gacgagcatt    16500
cctaggggtc tttcccctct cgccaaagga atgcaaggtc tgttgaatgt cgtgaaggaa    16560
gcagttcctc tggaagcttc ttgaagacaa acaacgtctg tagcgaccct ttgcaggcag    16620
cggaaccccc cacctggcga caggtgcctc tgcggccaaa agccacgtgt ataagataca    16680
cctgcaaagg cggcacaacc ccagtgccac gttgtgagtt ggatagttgt ggaaagagtc    16740
aaatggctct cctcaagcgt attcaacaag ggctgaagg atgcccagaa ggtacccat     16800 tgtatgggat ctgatctggg gcctcggtgc acatgcttta catgtgttta gtcgaggtta    16860
aaaaaacgtc taggccccccc gaaccacggg gacgtggttt cctttgaaa aacacgatga    16920 taaggatcca ccggaggcca ccatgaccga gtacaagccc acggtgcgcc tcgccacccg    16980
```

```
cgacgacgtc cccagggccg tacgcaccct cgccgccgcg ttcgccgact accccgccac    17040
gcgccacacc gtcgatccgg accgccacat cgagcgggtc accgagctgc aagaactctt    17100
cctcacgcgc gtcgggctcg acatcggcaa ggtgtgggtc gcggacgacg cgccgcggt     17160 ggcggtctgg accacgccgg agagcgtcga agcgggggcg gtgttcgccg agatcggccc    17220
gcgcatggcc gagttgagcg gttcccggct ggccgcgcag caacagatgg aaggcctcct    17280
ggcgccgcac cggcccaagg agcccgcgtg gttcctggcc accgtcggcg tctcgcccga    17340
ccaccagggc aagggtctgg gcagcgccgt cgtgctcccc ggagtggagg cggccgagcg    17400
cgccggggtg cccgccttcc tggagacctc cgccgccccgc aacctcccct tctacgagcg    17460
gctcggcttc accgtcaccg ccgacgtcga ggtgcccgaa ggaccgcgca cctggtgcat    17520
gacccgcaag cccggtgcct gaccgcgtct ggaacatgca tcggtacctt taagaccaat    17580
gacttacaag gcagctgtag atcttagcca cttttaaaa gaaaaggggg gacgtagtag    17640
ttcatgtcat cttattattc agtatttata acttgcaaag aaatgaatat cagagagtga    17700
gaggaacttg tttattgcag cttataatgg ttacaaataa agcaatagca tcacaaattt    17760
cacaaataaa gcattttttt cactgcattc tagttgtggt ttgtccaaac tcatcaatgt    17820
atcttagtta acgaattcgg cgcgccaatt gatcagcgct taagctagcg atcgcgggac    17880
tttccacacc ctaactgaca cacattccac agaattccca tcacaaagct ctgacctcaa    17940
tcctatagaa aggaggaatg agccaaaatt cacccaactt attgtgggaa gctggccttg    18000
gaggcctttt ccccgtatcc ccccaggtgt ctgcaggctc aaagagcagc gagaagcgtt    18060
cagaggaaag cgatcccgtg ccaccttccc cgtgcccggg ctgtccccgc acgctgccgg    18120
ctcggggatg cggggggagc gccggaccgg agcggagccc cggcggctc gctgctgccc    18180 cctagcgggg gagggacgta attacatccc tgggggcttt ggggggggc tgtccctcta    18240 gaactagtgg atccccggg ctgcaggaat tcgataaaag ttttgttact ttatagaaga    18300
aattttgagt ttttgttttt ttttaataaa taaataaaca taaataaatt gtttgttgaa    18360
tttattatta gtatgtaagt gtaaatataa taaaacttaa tatctattca aattaataaa    18420
taaacctcga tatacagacc gataaaacac atgcgtcaat tttacgcatg attatcttta    18480
acgtacgtca caatatgatt atctttctag ggttaatcta gctgcgtgtt ctgcagcgtg    18540
tcgagcatct tcatctgctc catcacgctg taaaacacat ttgcaccgcg agtctgcccg    18600
tcctccacgg gttcaaaaac gtgaatgaac gaggcgcgct cactggccgt cgttttacaa    18660
cgtcgtgact gggaaaaccc tggcgttacc caacttaatc gccttgcagc acatcccct     18720 ttcgccagct ggcgtaatag cgaagaggcc cgcaccgatc gcccttccca acagttgcgc    18780
agcctgaatg gcgaatggga cgcgccctgt agcggcgcat taagcgcggc gggtgtggtg    18840
gttacgcgca gcgtgaccgc tacacttgcc agcgccctag cgcccgctcc tttcgctttc    18900
ttcccttcct ttctcgccac gttcgccggc tttccccgtc aagctctaaa tcggggctc    18960 cctttagggt tccgatttag tgctttacgg cacctcgacc ccaaaaaact tgattagggt    19020
gatggttcac gtagtgggcc atcgccctga tagacggttt ttcgcccttt gacgttggag    19080
tccacgttct ttaatagtgg actcttgttc caaactggaa caacactcaa ccctatctcg    19140
gtctattctt ttgatttata agggattttg ccgatttcgg cctattggtt aaaaaatgag    19200
ctgatttaac aaaaatttaa cgcgaatttt aacaaaatat taacgcttac aatttaggtg    19260
gcacttttcg gggaaatgtg cgcggaaccc ctatttgttt attttctaa atacattcaa    19320 atatgtatcc gctcatgaga caataaccct gataaatgct tcaataatat tgaaaaagga    19380
``` agagt                                                                          19385

<210> SEQ ID NO 2
<211> LENGTH: 11565
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
atgagtattc aacatttccg tgtcgccctt attcccttt ttgcggcatt ttgccttcct      60
gttttgctc acccagaaac gctggtgaaa gtaaaagatg ctgaagatca gttgggtgca     120
cgagtgggtt acatcgaact ggatctcaac agcggtaaga tccttgagag ttttcgcccc    180
gaagaacgtt ttccaatgat gagcactttt aaagttctgc tatgtggcgc ggtattatcc    240
cgtattgacg ccgggcaaga gcaactcggt cgccgcatac actattctca gaatgacttg    300
gttgagtact caccagtcac agaaaagcat cttacggatg gcatgacagt aagagaatta    360
tgcagtgctg ccataaccat gagtgataac actgcggcca acttacttct gacaacgatc    420
ggaggaccga aggagctaac cgcttttttg cacaacatgg gggatcatgt aactcgcctt    480
gatcgttggg aaccggagct gaatgaagcc ataccaaacg acgagcgtga ccacgatg     540
cctgtagcaa tggcaacaac gttgcgcaaa ctattaactg gcgaactact tactctagct    600
tcccggcaac aattaataga ctggatggag gcggataaag ttgcaggacc acttctgcgc    660
tcggcccttc cggctggctg gtttattgct gataaatctg gagccggtga gcgtgggtct    720
cgcggtatca ttgcagcact ggggccagat ggtaagccct cccgtatcgt agttatctac    780
acgacgggga gtcaggcaac tatggatgaa cgaaatagac agatcgctga gataggtgcc    840
tcactgatta gcattggta actgtcagac caagtttact catatatact ttagattgat    900
ttaaaacttc attttttaatt taaaaggatc taggtgaaga tcctttttga taatctcatg    960
accaaaatcc cttaacgtga gttttcgttc cactgagcgt cagaccccgt agaaaagatc   1020
aaaggatctt cttgagatcc ttttttttctg cgcgtaatct gctgcttgca acaaaaaaa    1080
ccaccgctac cagcggtggt ttgtttgccg gatcaagagc taccaactct ttttccgaag   1140
gtaactggct tcagcagagc gcagatacca aatactgtcc ttctagtgta gccgtagtta   1200
ggccaccact tcaagaactc tgtagcaccg cctacatacc tcgctctgct aatcctgtta   1260
ccagtggctg ctgccagtgg cgataagtcg tgtcttaccg ggttggactc aagacgatag   1320
ttaccggata aggcgcagcg gtcgggctga acggggggtt cgtgcacaca gcccagcttg   1380
gagcgaacga cctacaccga actgagatac ctacagcgtg agctatgaga aagcgccacg   1440
cttcccgaag ggagaaaggc ggacaggtat ccggtaagcg gcagggtcgg aacaggagag   1500
cgcacgaggg agcttccagg gggaaacgcc tggtatcttt atagtcctgt cgggtttcgc   1560
cacctctgac ttgagcgtcg atttttgtga tgctcgtcag gggggcggag cctatggaaa   1620
aacgccagca acgcggcctt tttacggttc ctggcctttt gctggccttt tgctcacatg   1680
ttctttcctg cgttatcccc tgattctgtg ataaccgta ttaccgcctt tgagtgagct    1740
gataccgctc gccgcagccg aacgaccgag cgcagcgagt cagtgagcga ggaagcggaa   1800
gagcgcccaa tacgcaaacc gcctctcccc gcgcgttggc cgattcatta atgcagctgg   1860
cacgacaggt ttcccgactg gaaagcgggc agtgagcgca acgcaattaa tgtgagttag   1920
ctcactcatt aggcaccca ggctttacac tttatgcttc cggctcgtat gttgtgtgga   1980
```

```
attgtgagcg gataacaatt tcacacagga aacagctatg accatgatta cgccaagcgc   2040
gcccgccggg taactcacgg ggtatccatg tccatttctg cggcatccag ccaggatacc   2100
cgtcctcgct gacgtaatat cccagcgccg caccgctgtc attaatctgc acaccggcac   2160
ggcagttccg gctgtcgccg gtattgttcg ggttgctgat gcgcttcggg ctgaccatcc   2220
ggaactgtgt ccggaaaagc cgcgacgaac tggtatccca ggtggcctga acgaacagtt   2280
caccgttaaa ggcgtgcatg ccacaccttc cccgaatcat catggtaaac gtgcgttttc   2340
gctcaacgtc aatgcagcag cagtcatcct cggcaaactc tttccatgcc gcttcaacct   2400
cgcgggaaaa ggcacgggct tcttcctccc cgatgcccag atagcgccag cttgggcgat   2460
gactgagccg gaaaaaagac ccgacgatat gatcctgatg cagctagatt aaccctagaa   2520
agatagtctg cgtaaaattg acgcatgcat tcttgaaata ttgctctctc tttctaaata   2580
gcgcgaatcc gtcgctgtgc atttaggaca tctcagtcgc cgcttggagc tcccgtgagg   2640
cgtgcttgtc aatgcggtaa gtgtcactga ttttgaacta taacgaccgc gtgagtcaaa   2700
atgacgcatg attatctttt acgtgacttt taagatttaa ctcatacgat aattatattg   2760
ttatttcatg ttctacttac gtgataactt attatatata tattttcttg ttatagatat   2820
caagcttatc gataccgtcg acctcgaggg ggggcccggt acccaattcg ccctatagtg   2880
agtcgtatta agatctaatt aaccctcact aaagggaaca aaagctggag ctccaccgcg   2940
gtggcggccg ctctagaggg acagccccccc cccaaagccc ccagggatgt aattacgtcc   3000
ctcccccgct aggggcagc agcgagccgc ccggggctcc gctccggtcc ggcgctcccc   3060
ccgcatcccc gagccggcag cgtgcgggga cagcccgggc acggggaagg tggcacggga   3120
tcgctttcct ctgaacgctt ctcgctgctc tttgagcctg cagacacctg ggggatacg    3180 gggaaaaagc cataccaatg ggccctaaaa aaggaatcca gtcaattccg gggctaaacc   3240
tggctgccac tgtttcttta gggacttcgt tcctgtgagg acacctgcag gccggccgga   3300
tcctaggtat acgcgttaat taaagcttgt taacgacatt gattattgac tagttattaa   3360
tagtaatcaa ttacggggtc attagttcat agcccatata tggagttccg cgttacataa   3420
cttacggtaa atggcccgcc tggctgaccg cccaacgacc cccgcccatt gacgtcaata   3480
atgacgtatg ttcccatagt aacgccaata gggactttcc attgacgtca atgggtggag   3540
tatttacggt aaactgccca cttggcagta catcaagtgt atcatatgcc aagtacgccc   3600
cctattgacg tcaatgacgg taaatggccc gcctggcatt atgcccagta catgacctta   3660
tgggactttc ctacttggca gtacatctac gtattagtca tcgctattac catggtgatg   3720
cggttttggc agtacatcaa tgggcgtgga tagcggtttg actcacgggg atttccaagt   3780
ctccacccca ttgacgtcaa tgggagtttg ttttggcacc aaaatcaacg ggactttcca   3840
aaatgtcgta caactccgcc ccattgacg caaatgggcg gtaggcgtgt acggtgggag   3900
gtctatataa gcagcgcgtt ttgcctgtac tgggtctctc tggttagacc agatctgagc   3960
ctgggagctc tctggctaac tagggaaccc actgcttaag cctcaataaa gcttgccttg   4020
agtgcttcaa gtagtgtgtg cccgtctgtt gtgtgactct ggtaactaga gatccctcag   4080
acccttttag tcagtgtgga aaatctctag cagtggcgcc cgaacaggga cttgaaagcg   4140
aaagggaaac cagaggagct ctctcgacgc aggactcggc ttgctgaagc gcgcacggca   4200
agaggcgagg ggcggcgact ggtgagtacg ccaaaaattt tgactagcgg aggctagaag   4260
gagagagatg ggtgcgagag cgtcagtatt aagcggggga gaattagatc gcgatgggaa   4320
```

```
aaaattcggt taaggccagg gggaagaaa aatataaat taaaacatat agtatgggca    4380
agcagggagc tagaacgatt cgcagttaat cctggcctgt tagaaacatc agaaggctgt    4440
agacaaatac tgggacagct acaaccatcc cttcagacag gatcagaaga acttagatca    4500
ttatataata cagtagcaac cctctattgt gtgcatcaaa ggatagagat aaaagacacc    4560
aaggaagctt tagacaagat agaggaagag caaaacaaaa gtaagaccac cgcacagcaa    4620
gcggccggcc gctgatcttc agacctggag gaggagatat gagggacaat ggagaagtg    4680
aattatataa atataaagta gtaaaaattg aaccattagg agtagcaccc accaaggcaa    4740
agagaagagt ggtgcagaga gaaaaaagag cagtgggaat aggagctttg ttccttgggt    4800
tcttgggagc agcaggaagc actatgggcg cagcgtcaat gacgctgacg gtacaggcca    4860
gacaattatt gtctggtata gtgcagcagc agaacaattt gctgagggct attgaggcgc    4920
aacagcatct gttgcaactc acagtctggg gcatcaagca gctccaggca agaatcctgg    4980
ctgtggaaag atacctaaag gatcaacagc tcctggggat ttggggttgc tctggaaaac    5040
tcatttgcac cactgctgtg ccttggaatg ctagttggag taataaatct ctggaacaga    5100
tttggaatca cacgacctgg atggagtggg acagagaaat taacaattac acaagcttaa    5160
tacactcctt aattgaagaa tcgcaaaacc agcaagaaaa gaatgaacaa gaattattgg    5220
aattagataa atgggcaagt ttgtggaatt ggtttaacat aacaaattgg ctgtggtata    5280
taaaattatt cataatgata gtaggaggct tggtaggttt aagaatagtt tttgctgtac    5340
tttctatagt gaatagagtt aggcagggat attcaccatt atcgtttcag acccacctcc    5400
caaccccgag ggacccgac aggcccgaag gaatagaaga agaaggtgga gagagagaca    5460
gagacagatc cattcgatta gtgaacggat cggcactgcg tgcgccaatt ctgcagacaa    5520
atggcagtat tcatccacaa ttttaaaaga aaggggggga ttggggggta cagtgcaggg    5580
gaaagaatag tagacataat agcaacagac atacaaacta agaattaca aaaacaaatt    5640
acaaaaattc aaaattttcg ggtttattac agggacagca gagatccagt ttggttagta    5700
ccgggcccgc tctagagatc cgacgcgcca tctctaggcc cgcgccggcc ccctcgcaca    5760
gacttgtggg agaagctcgg ctactcccct gccccggtta atttgcatat aatatttcct    5820
agtaactata gaggcttaat gtgcgataaa agacagataa tctgttcttt ttaatactag    5880
ctacatttta catgataggc ttggatttct ataagagata caaatactaa attattattt    5940
taaaaacag cacaaaagga aactcaccct aactgtaaag taattgtgtg ttttgagact    6000
ataaatatcc cttggagaaa agccttgtta acgcgcggtg accctcgagg tcgacggtat    6060
cgataagctc gcttcacgag attccagcag gtcgagggac ctaataactt cgtatagcat    6120
acattatacg aagttatatt aagggttcca agcttaagcg gccgcgtgga taaccgtatt    6180
accgccatgc attagttatt aatagtaatc aattacgggg tcattagttc atagcccata    6240
tatggagttc cgcgttacat aacttacggt aaatggcccg cctggctgac cgcccaacga    6300
cccccgccca ttgacgtcaa taatgacgta tgttcccata gtaacgccaa tagggacttt    6360
ccattgacgt caatgggtgg agtatttacg gtaaactgcc cacttggcag tacatcaagt    6420
gtatcatatg ccaagtacgc ccccattga cgtcaatgac ggtaaatggc ccgcctggca    6480
ttatgcccag tacatgacct tatgggactt tcctacttgg cagtacatct acgtattagt    6540
catcgctatt accatggtga tgcggttttg gcagtacatc aatgggcgtg atagcggtt    6600
tgactcacgg ggatttccaa gtctccaccc cattgacgtc aatgggagtt tgttttggca    6660
ccaaaatcaa cgggactttc caaaatgtcg taacaactcc gccccattga cgcaaatggg    6720
```

```
cggtaggcgt gtacggtggg aggtctatat aagcagagct ggtttagtga accgtcagat    6780
ccgctagcgc taccggtcgc caccatggtg agcaagggcg aggagctgtt caccggggtg    6840
gtgcccatcc tggtcgagct ggacggcgac gtaaacggcc acaagttcag cgtgtccggc    6900
gagggcgagg gcgatgccac ctacggcaag ctgaccctga agttcatctg caccaccggc    6960
aagctgcccg tgccctggcc caccctcgtg accaccctga cctacggcgt gcagtgcttc    7020
agccgctacc ccgaccacat gaagcagcac gacttcttca agtccgccat gcccgaaggc    7080
tacgtccagg agcgcaccat cttcttcaag gacgacggca actacaagac ccgcgccgag    7140
gtgaagttcg agggcgacac cctggtgaac cgcatcgagc tgaagggcat cgacttcaag    7200
gaggacggca acatcctggg gcacaagctg gagtacaact acaacagcca caacgtctat    7260
atcatggccg acaagcagaa gaacggcatc aaggtgaact tcaagatccg ccacaacatc    7320
gaggacggca gcgtgcagct cgccgaccac taccagcaga cacccccat cggcgacggc    7380 cccgtgctgc tgcccgacaa ccactacctg agcacccagt ccgccctgag caaagacccc    7440
aacgagaagc gcgatcacat ggtcctgctg gagttcgtga ccgccgccgg gatcactctc    7500
ggcatggacg agctgtacaa gtaggaattc gtcgagggac ctaataactt cgtatagcat    7560
acattatacg aagttataca tgtttaaggg ttccggttcc actaggtaca attcgatatc    7620
aagcttatcg ataatcaacc tctgattac aaaatttgtg aaagattgac tggtattctt    7680
aactatgttg ctccttttac gctatgtgga tacgctgctt taatgccttt gtatcatgct    7740
attgcttccc gtatggcttt cattttctcc tccttgtata atcctggtt gctgtctctt    7800 tatgaggagt tgtggcccgt tgtcaggcaa cgtggcgtgg tgtgcactgt gtttgctgac    7860 gcaacccca ctggttgggg cattgccacc acctgtcagc tcctttccgg gactttcgct    7920
ttccccctcc ctattgccac ggcggaactc atcgccgcct gccttgcccg ctgctggaca    7980
ggggctcggc tgttgggcac tgacaattcc gtggtgttgt cggggaaatc atcgtccttt    8040
ccttggctgc tcgcctgtgt tgccacctgg attctgcgcg gacgtccttt ctgctacgtc    8100
ccttcggccc tcaatccagc ggaccttcct tcccgcggcc tgctgccggc tctgcggcct    8160
cttccgcgtc ttcgccttcg ccctcagacg agtcggatct ccctttgggc cgcctccccg    8220
catcgatacc gtcgacctcg atcgagacct agaaaaacat ggagcaatca caagtagcaa    8280
tacagcagct accaatgctg attgtgcctg gctagaagca caagaggagg aggaggtggg    8340
ttttccagtc acacctcagg taccctttaag accaatgact tacaaggcag ctgtagatct    8400
tagccacttt ttaaaagaaa aggggggact ggaagggcta attcactccc aacgaagaca    8460
agatatcctt gatctgtgga tctaccacac acaaggctac ttccctgatt ggcagaacta    8520
cacaccaggg ccagggatca gatatccact gacctttgga tggtgctaca agctagtacc    8580
agttgagcaa gagaaggtag aagaagccaa tgaaggagag aacacccgct tgttacaccc    8640
tgtgagcctg catgggatgg atgacccgga gagagaagta ttagagtgga ggtttgacag    8700
ccgcctagca tttcatcaca tggcccgaga gctgcatccg gactgtactg ggtctctctg    8760
gttagaccag atctgagcct gggagctctc tggctaacta gggaacccac tgcttaagcc    8820
tcaataaagc ttgccttgag tgcttcaagt agtgtgtgcc cgtctgttgt gtgactctgg    8880
taactagaga tccctcagac ccttttagtc agtgtggaaa atctctagca gttaacgaat    8940
tcggcgcgcc aattgatcag cgcttaagct agcgatcgcg ggactttcca caccctaact    9000
gacacacatt ccacagaatt cccatcacaa agctctgacc tcaatcctat agaaaggagg    9060
```

```
aatgagccaa aattcaccca acttattgtg ggaagctggc cttggaggcc tgtgtgtcag    9120
ttagggtgtg gaaagtcccc aggctcccca ggcaggcaga agtatgcaaa gcatgcatct    9180
caattagtca gcaaccaggt gtggaaagtc cccaggctcc ccagcaggca gaagtatgca    9240
aagcatgcat ctcaattagt cagcaaccat agtcccgccc ctaactccgc ccatcccgcc    9300
cctaactccg cccagttccg cccattctcc gccccatggc tgactaattt ttttttattta   9360 tgcagaggcc gaggccgcct ctgcctctga gctattccag aagtagtgag gaggcttttt    9420
tggaggccta ggcttttgca aaaagctccc gggagcttgt atatccatttt tcggatctga   9480 tcagcacgtg ttgacaatta atcatcggca tagtatatcg gcatagtata atacgacaag    9540
gtgaggaact aaaccatggc caagttgacc agtgccgttc cggtgctcac cgcgcgcgac    9600
gtcgccggag cggtcgagtt ctggaccgac cggctcgggt tctcccggga cttcgtggag    9660
gacgacttcg ccggtgtggt ccgggacgac gtgaccctgt tcatcagcgc ggtccaggac    9720
caggtggtgc cggacaacac cctggcctgg gtgtgggtgc gcggcctgga cgagctgtac    9780
gccgagtggt cggaggtcgt gtccacgaac ttccggacg cctccgggcc ggccatgacc    9840
gagatcggcg agcagccgtg ggggcgggag ttcgccctgc gcgacccggc cggcaactgc    9900
gtgcacttcg tggccgagga gcaggactga cacgtgctac gagatttcga ttccaccgcc    9960
gccttctatg aaaggttggg cttcggaatc gttttccggg acgccggctg gatgatcctc    10020
cagcgcgggg atctcatgct ggagttcttc gcccacccca acttgtttat tgcagcttat    10080
aatggttaca aataaagcaa tagcatcaca aatttcacaa ataaagcatt ttttttcactg   10140 cattctagtt gtggtttgtc caaactcatc aatgtatctt aaggcctttt ccccgtatcc    10200
ccccaggtgt ctgcaggctc aaagagcagc gagaagcgtt cagaggaaag cgatcccgtg    10260
ccaccttccc cgtgcccggg ctgtccccgc acgctgccgg ctcggggatg cgggggggagc   10320 gccggaccgg agcggagccc cgggcggctc gctgctgccc cctagcgggg gagggacgta    10380
attacatccc tgggggcttt gggggggggc tgtccctcta gaactagtgg atcccccggg    10440
ctgcaggaat tcgataaaag ttttgttact ttatagaaga aattttgagt ttttgttttt    10500
ttttaataaa taaataaaca taaataaatt gtttgttgaa tttattatta gtatgtaagt    10560
gtaaatataa taaaacttaa tatctattca aattaataaa taaacctcga tatacagacc    10620
gataaaacac atgcgtcaat tttacgcatg attatcttta acgtacgtca caatatgatt    10680
atctttctag ggttaatcta gctgcgtgtt ctgcagcgtg tcgagcatct tcatctgctc    10740
catcacgctg taaaacacat ttgcaccgcg agtctgcccg tcctccacgg gttcaaaaac    10800
gtgaatgaac gaggcgcgct cactggccgt cgttttacaa cgtcgtgact gggaaaaccc    10860
tggcgttacc caacttaatc gccttgcagc acatccccct ttcgccagct ggcgtaatag    10920
cgaagaggcc cgcaccgatc gcccttccca acagttgcgc agcctgaatg gcgaatggga    10980
cgcgccctgt agcggcgcat taagcgcggc gggtgtggtg gttacgcgca gcgtgaccgc    11040
tacacttgcc agcgccctag cgcccgctcc tttcgctttc ttcccttcct ttctcgccac    11100
gttcgccggc tttccccgtc aagctctaaa tcggggctc cctttagggt tccgatttag    11160
tgctttacgg cacctcgacc ccaaaaaact tgattaggt gatggttcac gtagtgggcc    11220
atcgccctga tagacggttt ttcgcccttt gacgttggag tccacgttct ttaatagtgg    11280
actcttgttc caaactggaa caacactcaa ccctatctcg gtctattctt ttgatttata    11340
agggattttg ccgatttcgg cctattggtt aaaaaatgag ctgatttaac aaaaatttaa    11400
cgcgaatttt aacaaaatat taacgcttac aatttaggtg gcacttttcg gggaaatgtg    11460
```

```
cgcggaaccc ctatttgttt atttttctaa atacattcaa atatgtatcc gctcatgaga    11520
caataaccct gataaatgct tcaataatat tgaaaaagga agagt                    11565
```

METHODS AND CONSTRUCTS FOR PRODUCTION OF LENTIVIRAL VECTOR

CROSS-REFERENCE TO RELATED APPLICATIONS

The present application claims benefit of U.S. Provisional Patent Application No. 62/890,904, filed Aug. 23, 2019, the disclosure of which is incorporated by reference herein in its entirety.

SEQUENCE LISTING

The instant application contains a Sequence Listing which has been submitted electronically in ASCII format and is hereby incorporated by reference in its entirety. Said ASCII copy, created on Sep. 22, 2020, is named 0132-0051US1_SL.txt and is 40,938 bytes in size.

FIELD OF THE INVENTION

The present disclosure relates to methods for producing lentiviral vector-producing cells. Specifically the methods utilize two plasmids, rather than four, to provide the required packaging elements and transfer vector to a cell, allowing for the production of a large number of lentiviral producer cells, including suspension-based cells, and the production of high amounts of lentivirus. These methods allow for the production of cells that can be later induced to produce lentivirus, and can be tailored to include a specific gene of interest.

BACKGROUND OF THE INVENTION

Lentiviral vectors are one of the most commonly used delivery methods in the field of gene and cell therapy. In the process of lentiviral vector production, the sequences required for production of the vector are divided into several different plasmids or expression cassettes to minimize the chance of yielding a replication-competent lentivirus (RCL). In general, 3rd generation lentivirus production systems utilize four separate plasmids or expression cassettes that express:

1) Lentiviral group specific antigen (GAG) gene and a lentiviral polymerase (POL) protein;
2) Envelope protein (usually Vesicular Stomatitis Virus Glycoprotein (VSV-G));
3) HIV regulator of expression of virion proteins (Rev) protein; and
4) A Transfer vector (TV) containing a gene of interest (GOI).

In the most common approach, the above four plasmids are transiently transfected into cells to produce lentiviral vectors, which is labor-intensive and costly. In addition, transient transfection has a limitation in scalability as it requires large amounts of plasmid DNAs, which also raises a concern for safety.

What are needed to overcome difficulties associated with transient transfection, are methods for preparing a producer cell line (PCL), in which all or most of the genes or sequences required for lentiviral vector production are stably integrated into the chromosome of a mamalian cell allowing for the production of lentiviral vectors by a simple induction method. The present invention fulfills these needs.

SUMMARY OF THE INVENTION

In some embodiments, provided herein is method of producing a lentiviral packaging vector-containing mammalian cell, comprising: transfecting a mammalian cell with: a packaging vector including an expression cassette, encoding: a lentiviral regulator of expression of virion proteins (REV) gene under control of a first promoter; a lentiviral envelope gene under control of a second promoter; and a lentiviral group specific antigen (GAG) gene and a lentiviral polymerase (POL) gene both under control of a third promoter, wherein the expression cassette is flanked on both the 5' and 3' ends by transposon-specific inverted terminal repeats (ITR); and culturing the transfected mammalian cell; and isolating the lentiviral packaging vector-containing mammalian cell.

Also provided herein is a method of producing a lentiviral vector-producing mammalian cell, comprising: transfecting a mammalian cell with: a packaging vector including an expression cassette, encoding: a lentiviral regulator of expression of virion proteins (REV) gene under control of a first promoter; a lentiviral envelope gene under control of a second promoter; and a lentiviral group specific antigen (GAG) gene and a lentiviral polymerase (POL) gene both under control of a third promoter, wherein the expression cassette is flanked on both the 5' and 3' ends by transposon-specific inverted terminal repeats (ITR); and a transfer vector, comprising: a nucleic acid sequence encoding a gene of interest under control of a fourth promoter, wherein the nucleic acid sequence is flanked on both the 5' and 3' ends by transposon-specific inverted terminal repeats (ITR); culturing the transfected mammalian cell; and isolating the lentiviral vector-producing mammalian cell.

In further embodiments, provided herein is a method of producing a lentiviral vector, comprising: producing a lentiviral packaging vector-containing mammalian cell according to methods described herein; transfecting the mammalian cell with a transfer vector, comprising: a nucleic acid sequence encoding a gene of interest under control of a fourth promoter; inducing production of the expression cassette and the nucleic acid; culturing the transfected mammalian cell; and harvesting the lentiviral vector.

Also provided herein is a method of producing a lentiviral vector, comprising: producing a lentiviral vector-producing mammalian cell according to the methods described herein, inducing production of the expression cassette and the nucleic acid; culturing the mammalian cell; and harvesting the lentiviral vector.

In additional embodiments, provided herein is a method of treatment with a lentiviral vector, comprising: administering the lentiviral vector produced according to the methods described herein to a mammalian subject.

In further embodiments, provided herein is a mammalian cell for producing a lentiviral vector, comprising: a nucleic acid molecule chromosomally integrated into the mammalian cell, the nucleic acid molecule comprising a lentiviral regulator of expression of virion proteins (REV) gene under control of a first promoter; a lentiviral envelope gene under control of a second promoter; and a lentiviral group specific antigen (GAG) gene and a lentiviral polymerase (POL) gene both under control of a third promoter, wherein the nucleic acid sequence is flanked on both the 5' and 3' ends by sequences resulting from the recombination of transposon-specific inverted terminal repeats (ITRs).

Also provided herein is a method of producing a lentiviral vector, comprising: transfecting the mammalian cells described herein with a transfer vector, comprising: an nucleic acid sequence encoding a gene of interest under control of a fourth promoter; inducing production of the expression cassette and the nucleic acid; culturing the transfected mammalian cell; and harvesting the lentiviral vector.

In further embodiments, provided herein is a method of producing a lentiviral vector, comprising: inducing production of the chromosomally integrated nucleic acid sequence and the chromosomally integrated nucleic acid sequence encoding a gene of interest of the mammalian cells described herein; culturing the mammalian cell; and harvesting the lentiviral vector.

DETAILED DESCRIPTION OF THE INVENTION

Figure 1:
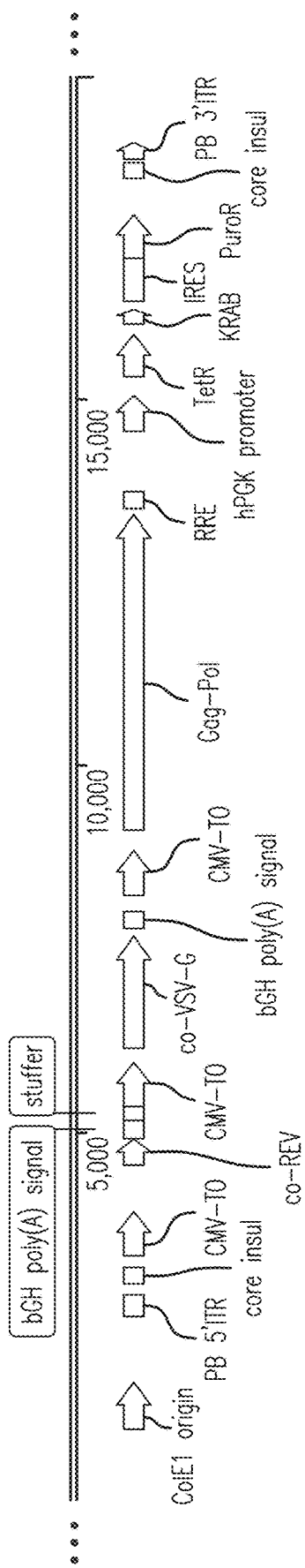
FIG. 1 shows a packaging plasmid in accordance with embodiments hereof.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the method/device being employed to determine the value. Typically the term is meant to encompass approximately or less than 1%, 2%, 3%, 4%, 5%, 6%, 7%, 8%, 9%, 10%, 11%, 12%, 13%, 14%, 15%, 16%, 17%, 18%, 19% or 20% variability depending on the situation.

The use of the term "or" in the claims is used to mean "and/or" unless explicitly indicated to refer only to alternatives or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited, elements or method steps. It is contemplated that any embodiment discussed in this specification can be implemented with respect to any method, system, host cells, expression vectors, and/or composition of the invention. Furthermore, compositions, systems, cells, and/or nucleic acids of the invention can be used to achieve any of the methods as described herein.

As used herein, "nucleic acid," "nucleic acid molecule," or "oligonucleotide" means a polymeric compound comprising covalently linked nucleotides. The term "nucleic acid" includes polyribonucleic acid (RNA) and polydeoxyribonucleic acid (DNA), both of which may be single- or double-stranded. DNA includes, but is not limited to, complimentary DNA (cDNA), genomic DNA, plasmid or vector DNA, and synthetic DNA. RNA includes, but is not limited to, mRNA, tRNA, rRNA, snRNA, microRNA, miRNA, or MIRNA.

A "gene" as used herein refers to an assembly of nucleotides that encode a polypeptide, and includes cDNA and genomic DNA nucleic acid molecules. "Gene" also refers to a nucleic acid fragment that can act as a regulatory sequence preceding (5' non-coding sequences) and following (3' non-coding sequences) the coding sequence. In some embodiments, genes are integrated with multiple copies. In some embodiments, genes are integrated at predefined copy numbers.

Lentiviral Vectors and Their Production

Lentiviral vector is a well studied vector system based on human immunodeficiency virus (HIV-1). Other lentiviral systems have also been developed as gene transfer systems, including HIV-2 simian immunodeficiency virus, nonprimate lentiviruses, feline immunodeficiency virus, and bovine immunodeficiency virus, etc. Guided by safety concerns due to the pathogenic nature of HIV-1 in humans, the most widely used lentiviral system for use in clinical and research and development purposes is based on the four-plasmid system that expresses:

1) Lentiviral group specific antigen (GAG) gene and a lentiviral polymerase (POL) protein
2) Envelope protein (usually Vesicular Stomatitis Virus Glycoprotein (VSV-G))
3) HIV regulator of expression of virion proteins (Rev) protein; and
4) A Transfer vector (TV) containing a gene of interest (GOI)

Traditionally, mammalian cells, such as human embryonic kidney cells (e.g., HEK293) are transfected with each of the four plasmids as an adherent cell culture, and then the desired lentivirus containing the gene of interest is produced. Generally, these transiently transfected cells are able to produce lentivirus.

Lentiviral vectors are generally produced with a gene of interest that is to be introduced into a desired cell for therapy and disease treatment, including immunodeficiencies and neurodegenerative diseases.

The present invention provides an improved methods of producing lentivirus, including methods for preparing lentivirus-producing cell lines that can be grown in suspension, allowing for a significant increase in the amount of lentivirus produced.

Lentiviral-Producing Cell Lines

In embodiments, provided herein is a method of producing a lentiviral packaging vector-containing mammalian cell. As used herein a "lentiviral packaging vector-containing cell" refers to a cell that contains, integrated into its genome, the elements required to produce a lentiviral vector, but that lacks a desired gene of interest that is to be carried by the lentiviral vector. Lentiviral packaging vector-containing cells can be later transfected with an e.g., transfer vector, that contains a desired gene of interest, and then subsequently induced to produce the desired lentivirus for ultimate delivery of the gene of interest.

Suitably, the cells that can be produced using the various methods described herein are mammalian cells and cell lines or cultures. As used herein, the term "mammalian cell" includes cells from any member of the order Mammalia, such as, for example, human cells, mouse cells, rat cells, monkey cells, hamster cells, and the like. In some embodiments, the cell is a mouse cell, a human cell, a Chinese hamster ovary (CHO) cell, a CHOK1 cell, a CHO-DXB11 cell, a CHO-DG44 cell, a CHOK1SV cell including all variants (e.g. POTELLIGENT®, Lonza, Slough, UK), a CHOK1SV GS-KO (glutamine synthetase knockout) cell including all variants (e.g., XCEED™ Lonza, Slough, UK). Exemplary human cells include human embryonic kidney (HEK) cells, such as HEK293, a HeLa cell, or a HT1080 cell.

Mammalian cells include mammalian cell cultures which can be either adherent cultures or suspension cultures. Adherent cultures refer to cells that are grown on a substrate surface, for example a plastic plate, dish or other suitable cell culture growth platform, and may be anchorage dependent. Suspension cultures refer to cells that can be maintained in, for example, culture flasks or large suspension vats, which allows for a large surface area for gas and nutrient exchange. Suspension cell cultures often utilize a stirring or agitation mechanism to provide appropriate mixing. Media and conditions for maintaining cells in suspension are generally known in the art. An exemplary suspension cell culture includes human HEK293 clonal cells.

In embodiments, the methods described herein include transfecting a mammalian cell with a packaging vector including an expression cassette. As used herein, a "vector" or "expression vector" is a replicon, such as a plasmid, phage, virus, or cosmid, to which a nucleic acid molecule described herein may be attached to bring about the replication and/or expression of the attached nucleic acid molecule in a cell. "Vector" includes episomal (e.g., plasmids) and non-episomal vectors. The term "vector" includes both viral and nonviral means for introducing a nucleic acid molecule into a cell in vitro, in vivo, or ex vivo. The term vector may include synthetic vectors. Vectors may be introduced into the desired host cells by well-known methods, including, but not limited to, transfection, transduction, cell fusion, and lipofection. Vectors can comprise various regulatory elements including promoters.

"Transfection" as used herein means the introduction of an exogenous nucleic acid molecule, including a vector, into a cell. A "transfected" cell comprises an exogenous nucleic acid molecule inside the cell and a "transformed" cell is one in which the exogenous nucleic acid molecule within the cell induces a phenotypic change in the cell. The transfected nucleic acid molecule can be integrated into the host cell's genomic DNA and/or can be maintained by the cell, temporarily or for a prolonged period of time, extra-chromosomally. Host cells or organisms that express exogenous nucleic acid molecules or fragments are referred to as "recombinant," "transformed," or "transgenic" organisms. A number of transfection techniques are generally known in the art. See, e.g., Graham et al., *Virology*, 52:456 (1973); Sambrook et al., Molecular Cloning, a laboratory manual, Cold Spring Harbor Laboratories, New York (1989); Davis et al., Basic Methods in Molecular Biology, Elsevier (1986); and Chu et al., *Gene* 13:197 (1981). Suitably, transfection of a mammalian cell with one or more of the vectors described herein utilizes a transfection agent, such as polyethylenimine (PEI) or other suitable agent, including various lipids and polymers, to integrate the nucleic acids into the host cell's genomic DNA.

As used herein, a "packaging vector" refers to a vector that contains the components necessary to produce a lentiviral vector and "package" a gene of interest in the final, lentivirus. The packaging vector includes an expression cassette, which refers to a distinct component of a vector, and includes one or more genes and regulatory sequences to be inserted into, and ultimately expressed by, a transfected cell.

Suitably, the expression cassette used in the packaging vector includes a lentiviral regulator of expression of virion proteins (REV) gene under control of a first promoter; a lentiviral envelope gene under control of a second promoter; and a lentiviral group specific antigen (GAG) gene and a lentiviral polymerase (POL) gene both under control of a third promoter. In other embodiments, a single promoter can control the expression of each of the REV, ENV, GAG and POL genes, or one promoter can control expression of GAG and POL, and a second promoter control the expression or REV and ENV. Other combinations are also possible and included herein.

The lentiviral regulator of expression of virion proteins (REV) is an RNA-binding protein that promotes late phase gene expression. It is also important for the transport of the unspliced or singly-spliced mRNAs, which encode viral structural proteins, from the nucleus to the cytoplasm.

The lentiviral envelope (ENV) gene, suitably a Vesicular Stomatitis Virus Glycoprotein (VSV-G) gene, encodes a polyprotein precursor which is cleaved by a cellular protease into the surface (SU) envelope glycoprotein gp120 and the transmembrane (TM) glycoprotein gp41.

GAG encodes a polyprotein that is translated from an unspliced mRNA which is then cleaved by the viral protease (PR) into the matrix protein, capsid, and nucleocapsid proteins. The lentiviral polymerase (POL) is expressed as a GAG-POL polyprotein as a result of ribosomal frameshifting during GAG mRNA translation, and encodes the enzymatic proteins reverse transcriptase, protease, and integrase. These three proteins are associated with the viral genome within the virion. Suitably the GAG gene is an HIV GAG gene and the POL gene is an HIV POL gene.

In suitable embodiments, the expression cassette is flanked on both the 5' and 3' ends by transposon-specific inverted terminal repeats (ITR). As described in detail herein, it is the use of transposon ITRs (in combination with a corresponding transposase) that allow for the specific integration of the expression cassette into the genome of the target cell.

The methods for producing the lentiviral packaging vector-containing mammalian cell further comprise culturing the transfected mammalian cell to allow for integration of the desired nucleic acids (i.e., the expression cassette) into the genome of the cell, followed by isolating the lentiviral packaging vector-containing mammalian cell.

Methods for culturing the transfected mammalian cell are known in the art and include the use of various cell culture media, appropriate gas concentration/exchange and temperature control to promote growth of the cells and integration of the constructs into the genome of the cell.

Methods of isolating the desired cells include various filtration techniques, including the use of sieves, filter apparatus, cell-selection apparatus and sorting, cell counting, etc.

As noted herein, each of the components of the expression cassette are under the control of a promoter. As used herein "under control" refers to a gene being regulated by a "promoter," "promoter sequence," or "promoter region," which refers to a DNA regulatory region/sequence capable of binding RNA polymerase and initiating transcription of a downstream coding or non-coding gene sequence. In other words, the promoter and the gene are in operable combination or operably linked. As referred to herein, the terms "in operable combination", "in operable order" and "operably linked" refer to the linkage of nucleic acid sequences in such a manner that a promoter capable of directing the transcription of a given gene and/or the synthesis of a desired protein molecule is produced. The term also refers to the linkage of amino acid sequences in such a manner so that a functional protein is produced.

In some examples of the present disclosure, the promoter sequence includes the transcription initiation site and extends upstream to include the minimum number of bases or elements necessary to initiate transcription at levels detectable above background. In some embodiments, the promoter sequence includes a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the gene expression, e.g., in the host cell or vectors of the present disclosure. In some embodiments, the promoter is not a leaky promoter, i.e., the promoter is not constitutively expressing any of the gene products as described herein. In other embodiments as described herein, the promoter is a constitutive promoter, which initiates mRNA synthesis independent of the influence of an external regulation.

Suitably, the promoters used to control the transcription of the various genes in the expression cassettes are derepressible promoters. As used herein, a "derepressible promoter" refers to a structure that includes a functional promoter and additional elements or sequences capable of binding to a repressor element to cause repression of the functional promoter. "Repression" refers to the decrease or inhibition of the initiation of transcription of a downstream coding or non-coding gene sequence by a promoter. A "repressor element" refers to a protein or polypeptide that is capable of binding to a promoter (or near a promoter) so as to decrease or inhibit the activity of the promoter. A repressor element can interact with a substrate or binding partner of the repressor element, such that the repressor element undergoes a conformation change. This conformation change in the repressor element takes away the ability of the repressor element to decrease or inhibit the promoter, resulting in the "derepression" of the promoter, thereby allowing the promoter to proceed with the initiation of transcription. A "functional promoter" refers to a promoter, that absent the action of the repressor element, would be capable of initiation transcription. Various functional promoters that can be used in the practice of the present invention are known in the art, and include for example, PCMV, PH1, P19, P5, P40 and promoters of Adenovirus helper genes (e.g., E1A, E1B, E2A, E4Orf6, and VA).

Exemplary repressor elements and their corresponding binding partners that can be used as derepressible promoters are known in the art, and include systems such as the cumate gene-switch system (CuO operator, CymR repressor and cumate binding partner) (see, e.g., Mullick et al., "The cumate gene-switch: a system for regulated expression in mammalian cells," BMC Biotechnology 6:43 (1-18) (2006), the disclosure of which is incorporated by reference herein in its entirety, including the disclosure of the derepressible promoter system described therein) and the TetO/TetR system described herein (see, e.g., Yao et al., "Tetracycline Repressor, tetR, rather than the tetR-Mammalian Cell Transcription Factor Fusion Derivatives, Regulates Inducible Gene Expression in Mammalian Cells," Human Gene Therapy 9:1939-1950 (1998), the disclosure of which is incorporated by reference herein in its entirety). In exemplary embodiments, the derepressible promoters comprise a functional promoter and either one two tetracycline operator sequences (TetO or TetO$_2$). Suitably, the expression cassette further encodes a repressor element of the first, second and third derepressible promoters, including a tetracycline repressor protein.

A schematic showing a depressible promoter system is provided in FIG. 1, illustrating an exemplary packaging plasmid in accordance with embodiments hereof. A derepressible promoter including the CMV promoter, including a TetO sequence is noted (CMV-TO). CMV-TO depressible promoters are illustrated operably linked to REV, VSV-G and GAG-POL genes; that is the first, second and third promoters can all be derepressible promoters, in suitable embodiments. Also illustrated is the TetR repressor element, under the control of another promoter system, the hPGK promoter.

Upon binding of a tetracycline repressor protein (TetR—the repressor elements for the TetO sequences), to the TetO sequences, the CMV promoters are repressed. That is, little or no transcription takes place from these promoters. Upon binding of a binding partner for TetR (suitably Doxycycline (Dox)), the TetR proteins change conformation, release from the TetO sequences, and the functional promoters begin their normal transcription processes, as they would naturally.

As shown in FIG. 1, the expression cassette can further include a Kruppel-associated box (KRAB) sequence following the sequence encoding the repressor element, suitably the tetracycline repressor protein. A KRAB sequence (approximately 75 amino acids) is a transcriptional repression domain from the human zinc finger protein 10, and provides increased regulation of the repressor element, suitably the TetR repressor element. The KRAB domain functions as a transcriptional repressor when tethered to the template DNA by a DNA-binding domain. Also illustrated are exemplary locations of the 5' and 3' ITR transposon sequences. As noted, the ITR sequences are located such that the entirety of the expression cassette is transposed into the cell of interest, allowing for all of the desired genes to be inserted into the host genome.

In exemplary embodiments, the expression cassette further includes one or more reporter genes for determining the appropriate integration of the cassette into the genome of the cell. As referred to herein, a "reporter gene" is a gene whose expression confers a phenotype upon a cell that can be easily identified and measured. In some embodiments, the reporter gene comprises a fluorescent protein gene. In some embodiments, the reporter gene comprises a selection gene. As referred to herein, the term "selection gene" refers to the use of a gene which encodes an enzymatic activity that confers the ability to grow in medium lacking what would otherwise be an essential nutrient; in addition, a selection gene may confer resistance to an antibiotic or drug upon the cell in which the selection gene is expressed. A selection gene may be used to confer a particular phenotype upon a host cell. When a host cell must express a selection gene to grow in selective medium, the gene is said to be a positive selection gene. A selection gene can also be used to select against host cells containing a particular gene; a selection gene used in this manner is referred to as a negative selection gene. In exemplary embodiments the selection gene is placed downstream of KRAB sequence following the repressor protein, and also downstream of an internal ribosome entry site (IRES) sequence. In exemplary embodiments, the selection gene is an antibiotic resistance gene, including for example a gene that confers resistance to gentamycin, thymidine kinase, ampicillin, puromycin, and/or kanamycin.

As described in detail herein, it has been determined that the use of transposon-specific ITRs allow for the insertion of the expression cassette into the genome of a target cell with increased specificity, frequency and stability. In exemplary embodiments, the transposon-specific ITRs are Lepidopteran transposon (PIGGYBAC®) ITRs.

Transposable elements (transposons) can move around a genome of a cell and are useful for inserting genes for the production of transgenic organisms. The Lepidopteran transposon PIGGYBAC® is capable of moving within the genomes of a wide variety of species, and is useful in gene transduction vectors. The transposon structure includes a complex repeat configuration consisting of an internal repeat (IR), a spacer, and a terminal repeat (TR) at both ends, and a single open reading frame encoding a transposase.

The Lepidopteran transposable element PIGGYBAC® was originally isolated from the TN-368 *Trichoplusia ni* cell culture as a gene disrupting insertion within spontaneous baculovirus plaque morphology mutants. PIGGYBAC® is a 2475 bp short inverted repeat element that has an asymmetric terminal repeat structure with a 3-bp spacer between the 5' 13-bp TR (terminal repeat) and the 19-bp IR (internal repeat), and a 31-bp spacer between the 3' TR and IR. The single 2.1 kb open reading frame encodes a functional transposase (Cary et al., 1989; Fraser et al., 1983, 1995; Elick et al., 1996a; Lobo et al., 1999; Handler et al., 1998). PIGGYBAC® transposes via a unique cut-and-paste mechanism, inserting exclusively at 5' TTAA 3' target sites that are duplicated upon insertion, and excising precisely, leaving no footprint (Elick et al., 1996b; Fraser et al., 1996; Wang and Fraser 1993).

Exemplary Lepidopteran transposon (PIGGYBAC®) ITRs that can be used in the plasmids and expression cassettes described herein include those disclosed in U.S. Pat. No. 7,105,343, the disclosure of which is incorporated by reference herein in its entirety.

In suitable embodiments, transfecting of the mammalian cells with the packaging vector takes place in the presence of a transposase that recognizes the transposon-specific ITRs. This transposase facilitates the transposition of the expression cassette into the cellular genome of the target mammalian cell. Transposase can be provided to the cell either as an active enzyme, or as a nucleic acid sequence that encodes the transposase, including mRNA or cDNA. In embodiments, the transposase is Lepidopteran (PIGGYBAC®) transposase mRNA or Lepidopteran (PIGGYBAC®) transpose cDNA. As described herein, the frequency of the transposition utilizing Lepidopteran transposon (PIGGYBAC®) ITRs and corresponding Lepidopteran (PIGGYBAC®) transposase is suitably at least about $10^{-4}$.

In further embodiments, provided herein are methods of producing a lentiviral vector-producing mammalian cell. As used herein a "lentiviral vector-producing cell" refers to a cell that contains, integrated into its genome, the elements required to produce a lentiviral vector, as well a desired gene of interest that is to be carried by the lentiviral vector. Lentiviral vector-producing cells can be later induced to produce the desire lentivirus for ultimate delivery of the gene of interest.

Methods producing a lentiviral vector-producing cell, and in particular mammalian cells, include transfecting a mammalian cell with: packaging vector including an expression cassette, encoding: a lentiviral regulator of expression of virion proteins (REV) gene under control of a first promoter; a lentiviral envelope gene under control of a second promoter; and a lentiviral group specific antigen (GAG) gene and a lentiviral polymerase (POL) gene both under control of a third promoter.

As described herein the expression cassette is suitably flanked on both the 5' and 3' ends by transposon-specific inverted terminal repeats (ITR) to facilitate high transposition into the target cell.

The methods further include transecting the mammalian cell with a transfer vector, comprising: a nucleic acid sequence encoding a gene of interest under control of a fourth promoter. As with the expression cassette, the nucleic acid sequence encoding the gene of interest is also suitably flanked on both the 5' and 3' ends by transposon-specific inverted terminal repeats (ITR) for increased transposition. In embodiments both the transfer vector and the packaging vector are transfected at the same time; in other embodiments, the transfer vector or the packaging vector can be transfected first, with the other vector transfected at a later time.

Following the transfection, the mammalian cell is cultured, and the lentiviral vector-producing mammalian cell is isolated.

As with the lentiviral packaging vector-containing cells, lentiviral vector-producing cells prepared herein are suitably stored prior to the desired time at which they can be utilized to produce lentiviral vectors. Suitable storage techniques and characteristics are known in the art and can include refrigeration or freezing of cells, as well as other methods of maintaining the cells in a suspended state prior to induction of the vector production.

As described herein, suitably the mammalian cell is a mammalian cell culture, and in embodiments is a suspension culture. Exemplary cells include HEK293T cells.

As in the lentiviral packaging vector-containing cells, the genes of the expression vector suitably include a GAG gene that is an HIV GAG gene and a POL gene that is an HIV POL gene. Suitably, the lentiviral envelope gene is a Vesicular Stomatitis Virus Glycoprotein (VSV-G) gene.

Exemplary promoters for use in the lentiviral vector-producing cells are known in the art and include derepressible promoters, and suitably the expression cassette further encodes a repressor element of the first, second and third derepressible promoters. In embodiments, the derepressible promoters comprises a functional promoter and a tetracycline operator sequence (TetO), and the repressor element is a tetracycline repressor protein. Additional characteristics of the expression cassette, including the transposon-specific ITRs are described herein.

In suitable embodiments, the gene of interest that is to be contained in the lentiviral vector is a gene of therapeutic interest. As referred to herein, the term "gene of interest" or "GOI" is used to describe a heterologous gene. As referred to herein, the term "heterologous gene" or "HG" as it relates to nucleic acid sequences such as a coding sequence or a control sequence, denotes a nucleic acid sequence, e.g. a gene, that is not normally joined together, and/or are not normally associated with a particular cell. In some embodiments, a heterologous gene is a construct where the coding sequence itself is not found in nature (e.g., synthetic sequences having codons different from the native gene). Allelic variation or naturally occurring mutational events do not give rise to heterologous DNA, as used herein.

As referred to herein, the term "gene of therapeutic interest" refers to any functionally relevant nucleotide sequence. Thus, the gene of therapeutic interest of the present disclosure can comprise any desired gene that encodes a protein that is defective or missing from a therapy-target cell genome or that encodes a non-native protein having a desired biological or therapeutic effect (e.g., an antiviral function), or the sequence can correspond to a molecule having an antisense or ribozyme function. Representative (non-limiting) examples of suitable genes of therapeutic interest include those used for the treatment of inflammatory diseases, autoimmune, chronic and infectious diseases, including such disorders as AIDS, cancer, neurological diseases, cardiovascular disease, hypercholestemia; various blood disorders including various anemias, thalassemias and hemophilia; genetic defects such as cystic fibrosis, Gaucher's Disease, adenosine deaminase (ADA) deficiency, emphysema, etc. Several antisense oligonucleotides (e.g., short oligonucleotides complementary to sequences around the translational initiation site (AUG codon) of an mRNA) that are useful in antisense therapy for cancer and for viral diseases have been described in the art and are also examples of suitable genes of therapeutic interest.

Figure 2:
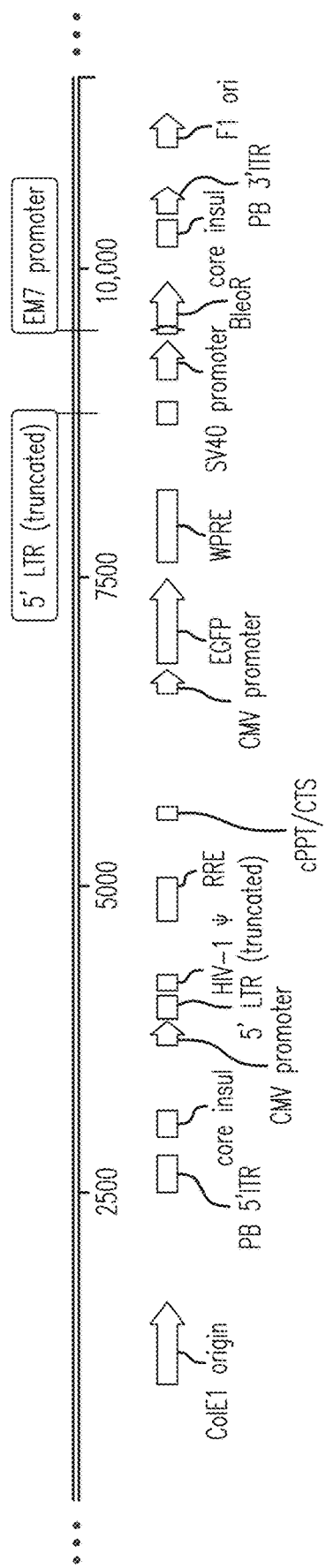
FIG. 2 shows a transfer vector in accordance with embodiments hereof.
Figure 3A:
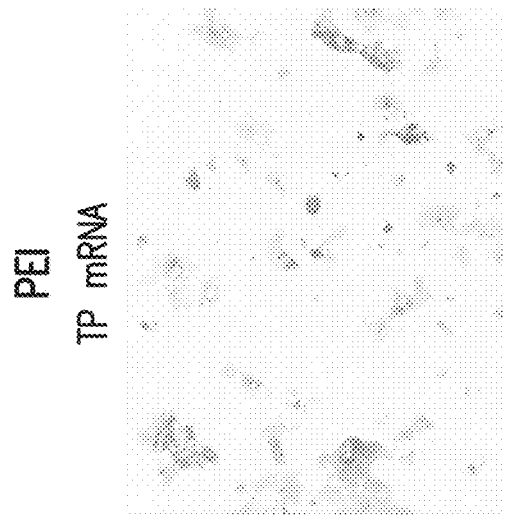
FIGS. 3A-3D show HEK293T cells transfected with packaging and transfer vectors, in accordance with embodiments hereof.
Figure 3B:
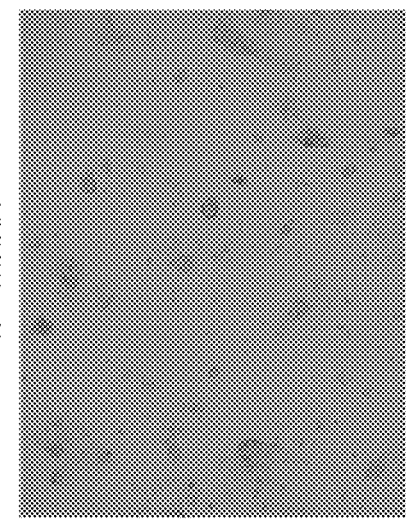
Figure 3C:
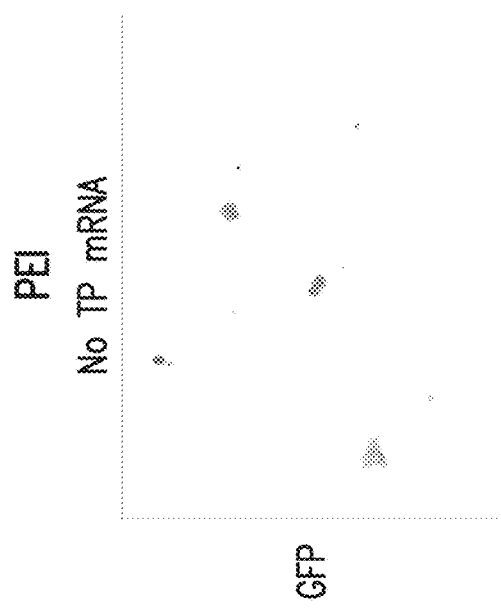
Figure 3D:
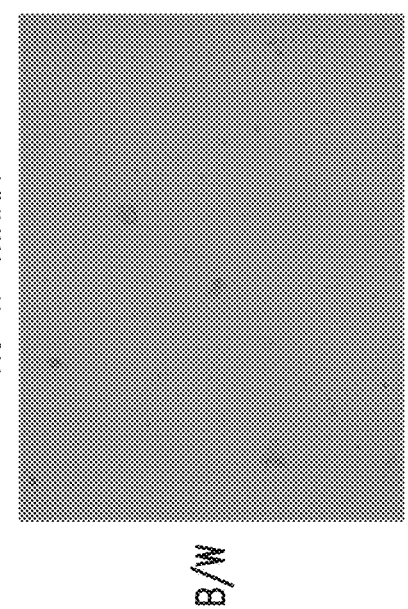

FIG. 2 shows an exemplary transfer vector that includes a gene of interest (enhanced green fluorescent protein for illustrative purposes). The gene of interest is under the control of a promoter, suitably a constitutive promoter, in this case a CMV promoter. Also illustrated are exemplary locations for the 5' and 3' ITR transposon sequences. As noted, the ITR sequences are located such that the entirety of the nucleic acid that contains the gene of interest and the promoter is transposed into the cell of interest, allowing for all of the desired genes to be inserted into the host genome. As indicated, the exemplary transfer vector also includes a selection gene, in this case a bleomycin resistance gene, downstream of the gene of interest. Additional elements of the transfer vector are shown in FIG. 2.

In additional embodiments, provided herein is a method of producing a lentiviral vector, comprising producing or providing a lentiviral packaging vector-containing mammalian cell as described herein, then transfecting the mammalian cell with a transfer vector, comprising a nucleic acid sequence encoding a gene of interest under control of a fourth promoter. Following the introduction of the gene of interest into the cellular genome, the production of the expression cassette and the nucleic acid encoding the gene of interest are induced. The cells are then cultured, and finally the lentiviral vector containing the gene of interest is harvested.

In still further embodiments, methods of producing a lentiviral vector suitably include producing or providing a lentiviral vector-producing mammalian cell as described herein. The production of the expression cassette and the nucleic acid encoding the gene of interest are induced. The cells are then cultured, and finally the lentiviral vector containing the gene of interest is harvested.

The methods of producing lentiviral vector using the cells described herein, whether they contain simply the lentiviral packaging vector, or also contain the gene of interest, integrated into the cellular genome, provide a mechanism for generation of large amounts of lentiviral vector, as well as controlling when the induction begins and the conditions under which the induction takes place. Induction suitably comprises the introduction of a chemical or agent that interacts with the repressor element, thereby derepressing the derepressible promoter, and allowing production of the packaging components of the lentiviral vector.

As described herein, suitably each of the promoters in the expression cassette is a derepressible promoter comprising a functional promoter and a tetracycline operator sequence (TetO), and the repressor element is a tetracycline repressor protein. In such embodiments, induction of packing components includes adding doxycycline to the mammalian cell.

The methods described herein provide for an increased amount of production of lentiviral vector, as a result of the increase in insertion of the desired nucleic acid sequences into the cellular genome and the suspension-based cell culture allowing for large volume production. In embodiments, the amount of the lentiviral vector produced is at least about $10^4$, more suitably about $10^5$ or about $10^6$ transduction units/mL, within about 1-5 days, suitably about two days after the inducing of the cells.

Production methods using the cells described herein can utilize any suitable reactor(s) including but not limited to stirred tank, airlift, fiber, microfiber, hollow fiber, ceramic matrix, fluidized bed, fixed bed, and/or spouted bed bioreactors. As used herein, "reactor" can include a fermenter or fermentation unit, or any other reaction vessel and the term "reactor" is used interchangeably with "fermenter." The term fermenter or fermentation refers to both microbial and mammalian cultures. For example, in some aspects, an example bioreactor unit can perform one or more, or all, of the following: feeding of nutrients and/or carbon sources, injection of suitable gas (e.g., oxygen), inlet and outlet flow of fermentation or cell culture medium, separation of gas and liquid phases, maintenance of temperature, maintenance of oxygen and $CO_2$ levels, maintenance of pH level, agitation (e.g., stirring), and/or cleaning/sterilizing. Example reactor units, such as a fermentation unit, may contain multiple reactors within the unit, for example the unit can have 1, 2, 3, 4, 5, 10, 15, 20, 25, 30, 35, 40, 45, 50, 60, 70, 80, 90, or 100, or more bioreactors in each unit and/or a facility may contain multiple units having a single or multiple reactors within the facility. In various embodiments, the bioreactor can be suitable for batch, semi fed-batch, fed-batch, perfusion, and/or a continuous fermentation processes. Any suitable reactor diameter can be used. In embodiments, the bioreactor can have a volume between about 100 mL and about 50,000 L. Non-limiting examples include a volume of 100 mL, 250 mL, 500 mL, 750 mL, 1 liter, 2 liters, 3 liters, 4 liters, 5 liters, 6 liters, 7 liters, 8 liters, 9 liters, 10 liters, 15 liters, 20 liters, 25 liters, 30 liters, 40 liters, 50 liters, 60 liters, 70 liters, 80 liters, 90 liters, 100 liters, 150 liters, 200 liters, 250 liters, 300 liters, 350 liters, 400 liters, 450 liters, 500 liters, 550 liters, 600 liters, 650 liters, 700 liters, 750 liters, 800 liters, 850 liters, 900 liters, 950 liters, 1000 liters, 1500 liters, 2000 liters, 2500 liters, 3000 liters, 3500 liters, 4000 liters, 4500 liters, 5000 liters, 6000 liters, 7000 liters, 8000 liters, 9000 liters, 10,000 liters, 15,000 liters, 20,000 liters, and/or 50,000 liters. Additionally, suitable reactors can be multi-use, single-use, disposable, or non-disposable and can be formed of any suitable material including metal alloys such as stainless steel (e.g., 316L or any other suitable stainless steel) and Inconel, plastics, and/or glass.

As described herein, it has been surprisingly determined that at least portions of the methods for producing lentivirus using producing cells lines can be carried out in the absence of antibiotics, including seed train production, cell passages, large volume cell culture and/or main manufacturing stages. By removing antibiotics from at least a portion of the lentivirus production process, the resulting methods reduce or remove concerns related to the use of antibiotics in cell processes and products that will ultimately be utilized in humans.

Figure 10:
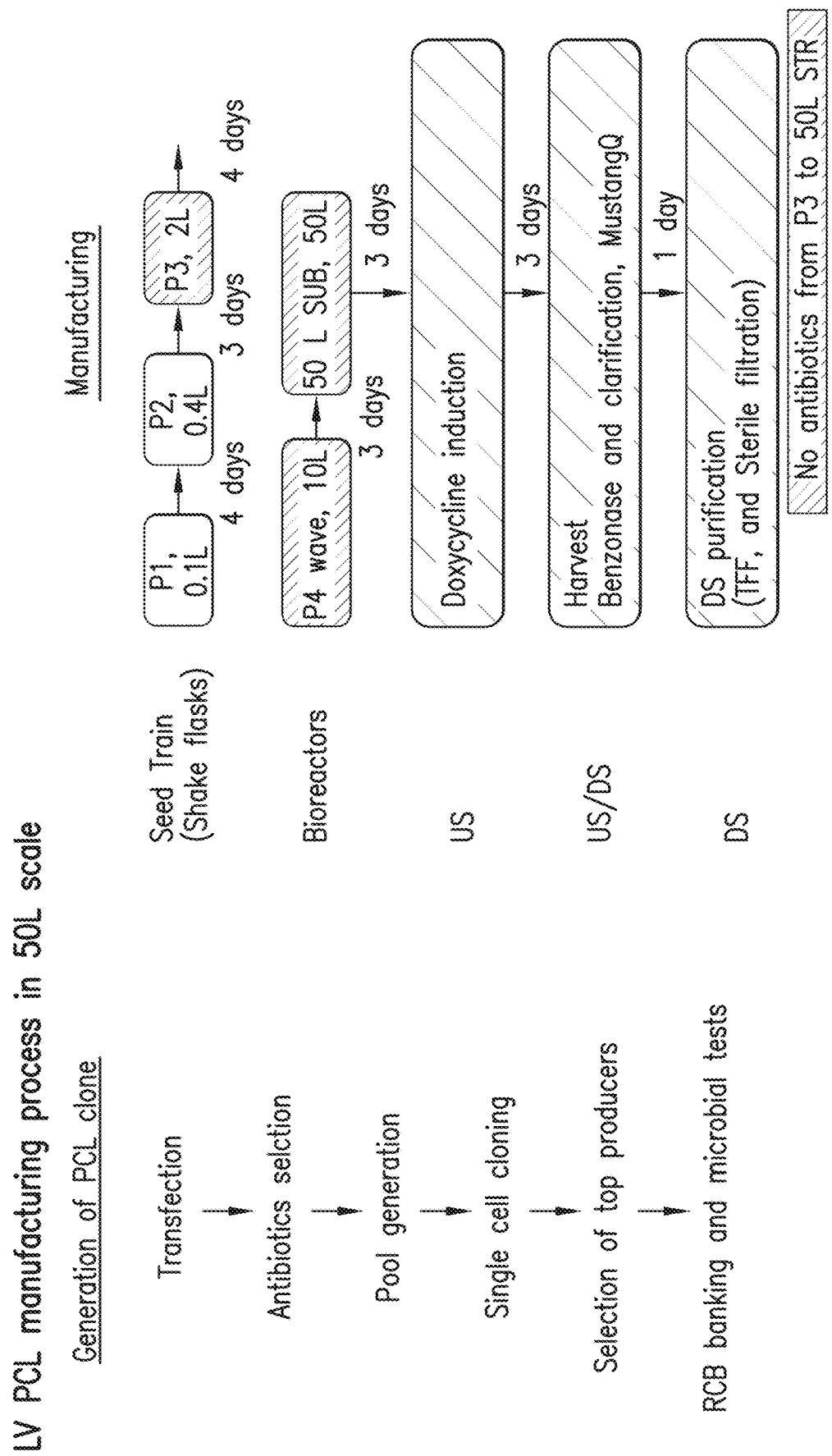
FIG. 10 shows an exemplary manufacturing flow for lentivirus PCL without antibiotics during parts of a seed train culture.

FIG. 10 shows an exemplary manufacturing process flow for preparing lentivirus from producer cell lines as described herein. As shown, PCL clones are first generated, and then selected for use in a large scale manufacturing process. During initial stages of the manufacturing process, the PCLs are passaged up to about 3 times (e.g., a volume of about 2 L), at which time antibiotics such as puromycin and/or zeocin, can be removed from the process. The passages can then be continued in the absence of antibiotic, for example from passage 3, passage 4, passage 5, etc., until the desired volume of cells is reached. For example, as shown in FIG. 10, suitably a volume of about 50 L is reached in a bioreactor, in the absence of an antibiotic. The PCLs are then suitably induced (e.g., using doxycycline as described herein) to begin the production of the lentiviral vector. Thus, in embodiments, a at least a portion of the culturing of the mammalian cells (PCLs) occurs in the absence of an antibiotic, and suitably this period is from passage 3 up to an induction phase. Following induction, downstream processing can take place, including harvesting (including benzonase treatment and clarification steps) and purification of the lentiviral vector (including tangential flow filtration and sterile filtration). The ability to carry out significant portions of the lentiviral vector production process using PCLs as described herein is a surprising and unexpected result and provides significant advantages to large scale manufacturing processes.

Also provided herein are methods of treating a mammalian subject, suitably a human subject, with a lentiviral vector produced according to the various methods described herein. Suitably, the methods are used to treat a human subject with a gene of interested, including a gene of therapeutic interest. Administration to a human subject can include, for example, inhalation, injection, or intravenous administration, as well as other administration methods known in the art.

Also provided herein are mammalian cells for producing a lentiviral vector. Using the methods described herein, or variations thereof, mammalian cells are readily produced that include a nucleic acid molecule chromosomally integrated into the mammalian cell, the nucleic acid molecule comprising a lentiviral regulator of expression of virion proteins (REV) gene under control of a first promoter; a lentiviral envelope gene under control of a second promoter; and a lentiviral group specific antigen (GAG) gene and a lentiviral polymerase (POL) gene both under control of a third promoter. In further embodiments, mammalian cells containing the packaging components integrated into the genome can further include a chromosomally integrated nucleic acid sequence encoding a gene of interest under control of a fourth promoter.

As described herein, the use of transposase-based methods, including PIGGYBAC® transposase, results in the nucleic acid sequence in the host cell genome being flanked on both the 5' and 3' ends by sequences resulting from the recombination of transposon-specific inverted terminal repeats (ITRs).

Exemplary mammalian cells are described herein, as are the gene components of the expression cassette and the nucleic acid encoding the gene of interest.

Methods of producing lentivirus utilizing these cells are described herein, and suitably include inducing production of the expression cassette and the nucleic acid encoding the gene of interest, culturing the transfected mammalian cell, and harvesting the lentiviral vector.

Additional Exemplary Embodiments

Embodiment 1 is a method of producing a lentiviral packaging vector-containing mammalian cell, comprising: transfecting a mammalian cell with: a packaging vector including an expression cassette, encoding: a lentiviral regulator of expression of virion proteins (REV) gene under control of a first promoter; a lentiviral envelope gene under control of a second promoter; and a lentiviral group specific antigen (GAG) gene and a lentiviral polymerase (POL) gene both under control of a third promoter, wherein the expression cassette is flanked on both the 5' and 3' ends by transposon-specific inverted terminal repeats (ITR); and culturing the transfected mammalian cell; and isolating the lentiviral packaging vector-containing mammalian cell.

Embodiment 2 includes the method of embodiment 1, wherein the mammalian cell is a mammalian cell culture.

Embodiment 3 includes the method of embodiment 2, wherein the mammalian cell culture is a suspension culture.

Embodiment 4 includes the method of embodiment 3, wherein the mammalian cell is an HEK293T cell.

Embodiment 5 includes the method of any one of embodiments 1-4, wherein the GAG gene is an HIV GAG gene and the POL gene is an HIV POL gene.

Embodiment 6 includes the method of any one of embodiments 1-5, wherein the lentiviral envelope gene is a Vesicular Stomatitis Virus Glycoprotein (VSV-G) gene.

Embodiment 7 includes the method of any one of embodiments 1-6, wherein the first, second and third promoters are derepressible promoters.

Embodiment 8 includes the method of embodiment 7, wherein the expression cassette further encodes a repressor element of the first, second and third derepressible promoters Embodiment 9 includes the method of embodiment 8, wherein each of the derepressible promoters comprises a functional promoter and a tetracycline operator sequence (TetO), and the repressor element is a tetracycline repressor protein.

Embodiment 10 includes the method of embodiment 9, wherein the expression cassette further comprises a Kruppel-associated box sequence following a sequence encoding the tetracycline repressor protein.

Embodiment 11 includes the method of any one of embodiments 1-10, wherein the transposon-specific ITRs are Lepidopteran transposon (PIGGYBAC®) ITRs.

Embodiment 12 includes the method of any one of embodiments 1-11, wherein the transfecting is in the presence of a transposase that recognizes the transposon-specific ITRs.

Embodiment 13 includes the method of embodiment 12, wherein the transposase is Lepidopteran (PIGGYBAC®) transposase mRNA or Lepidopteran (PIGGYBAC®) transpose cDNA.

Embodiment 14 is a method of producing a lentiviral vector-producing mammalian cell, comprising: transfecting a mammalian cell with: a packaging vector including an expression cassette, encoding: a lentiviral regulator of expression of virion proteins (REV) gene under control of a first promoter; a lentiviral envelope gene under control of a second promoter; and a lentiviral group specific antigen (GAG) gene and a lentiviral polymerase (POL) gene both under control of a third promoter, wherein the expression cassette is flanked on both the 5' and 3' ends by transposon-specific inverted terminal repeats (ITR); and a transfer vector, comprising: a nucleic acid sequence encoding a gene of interest under control of a fourth promoter, wherein the nucleic acid sequence is flanked on both the 5' and 3' ends by transposon-specific inverted terminal repeats (ITR); culturing the transfected mammalian cell; and isolating the lentiviral vector-producing mammalian cell.

Embodiment 15 includes the method of embodiment 14, wherein the mammalian cell is a mammalian cell culture.

Embodiment 16 includes the method of embodiment 15, wherein the mammalian cell culture is a suspension culture.

Embodiment 17 includes the method of embodiment 16, wherein the mammalian cell is an HEK293T cell.

Embodiment 18 includes the method of any one of embodiments 14-17, wherein the GAG gene is an HIV GAG gene and the POL gene is an HIV POL gene.

Embodiment 19 includes the method of any one of embodiments 14-18, wherein the lentiviral envelope gene is a Vesicular Stomatitis Virus Glycoprotein (VSV-G) gene.

Embodiment 20 includes the method of any one of embodiments 14-19, wherein the first, second and third promoters are derepressible promoters.

Embodiment 21 includes the method of embodiment 20, wherein the expression cassette further encodes a repressor element of the first, second and third derepressible promoters Embodiment 22 includes the method of embodiment 21, wherein each of the derepressible promoters comprises a functional promoter and a tetracycline operator sequence (TetO), and the repressor element is a tetracycline repressor protein.

Embodiment 23 includes the method of embodiment 22, wherein the expression cassette further comprises a Kruppel-associated box sequence following a sequence encoding the tetracycline repressor protein.

Embodiment 24 includes the method of any one of embodiments 14-23, wherein the transposon-specific ITRs are Lepidopteran transposon (PIGGYBAC®) ITRs.

Embodiment 25 includes the method of any one of embodiments 14-24, wherein the transfecting is in the presence of a transposase that recognizes the transposon-specific ITRs.

Embodiment 26 includes the method of embodiment 25, wherein the transposase is Lepidopteran (PIGGYBAC®) transposase mRNA or Lepidopteran (PIGGYBAC®) transpose cDNA.

Embodiment 27 includes the method of any one of embodiments 14-26, wherein the gene of interest is a gene of therapeutic interest.

Embodiment 28 is a method of producing a lentiviral vector, comprising: producing a lentiviral packaging vector-containing mammalian cell according to embodiment 1; transfecting the mammalian cell with a transfer vector, comprising: a nucleic acid sequence encoding a gene of interest under control of a fourth promoter; inducing production of the expression cassette and the nucleic acid; culturing the transfected mammalian cell; and harvesting the lentiviral vector.

Embodiment 29 is a method of producing a lentiviral vector, comprising: producing a lentiviral vector-producing mammalian cell according to embodiment 14; inducing production of the expression cassette and the nucleic acid; culturing the mammalian cell; and harvesting the lentiviral vector.

Embodiment 30 includes the method of embodiment 28 or embodiment 29, wherein each of the promoters in the expression cassette is a derepressible promoter comprising a functional promoter and a tetracycline operator sequence (TetO), and the repressor element is a tetracycline repressor protein, and the inducing includes adding doxycycline to the mammalian cell.

Embodiment 31 includes the method of embodiment 28 or embodiment 29, wherein an amount of the lentiviral vector produced is at least about $10^6$ transduction units/mL two days after the inducing.

Embodiment 32 is a method of treatment with a lentiviral vector, comprising: administering the lentiviral vector produced according to embodiment 28 or embodiment 29 to a mammalian subject.

Embodiment 33 includes the method of embodiment 32, wherein the administering comprises inhalation, injection or intravenous administration.

Embodiment 34 is a mammalian cell for producing a lentiviral vector, comprising: a nucleic acid molecule chromosomally integrated into the mammalian cell, the nucleic acid molecule comprising a lentiviral regulator of expression of virion proteins (REV) gene under control of a first promoter; a lentiviral envelope gene under control of a second promoter; and a lentiviral group specific antigen (GAG) gene and a lentiviral polymerase (POL) gene both under control of a third promoter, wherein the nucleic acid sequence is flanked on both the 5' and 3' ends by sequences resulting from the recombination of transposon-specific inverted terminal repeats (ITRs).

Embodiment 35 includes the mammalian cell of embodiment 34, further comprising a chromosomally integrated nucleic acid sequence encoding a gene of interest under control of a fourth promoter.

Embodiment 36 includes the mammalian cell of embodiment 34 or embodiment 35, wherein the mammalian cell is a mammalian cell culture.

Embodiment 37 includes the mammalian cell of embodiment 36, wherein the mammalian cell culture is a suspension culture.

Embodiment 38 includes the mammalian cell of embodiment 37, wherein the mammalian cell is an HEK293T cell.

Embodiment 39 includes the mammalian cell of any one of embodiments 34-38, wherein the GAG gene is an HIV GAG gene and the POL gene is an HIV POL gene.

Embodiment 40 includes the mammalian cell of any one of embodiments 34-39, wherein the lentiviral envelope gene is a Vesicular Stomatitis Virus Glycoprotein (VSV-G) gene.

Embodiment 41 includes the mammalian cell of any one of embodiments 34-40, wherein the first, second and third promoters are derepressible promoters.

Embodiment 42 includes the mammalian cell of embodiment 41, wherein the expression cassette further encodes a repressor element of the first, second and third derepressible promoters Embodiment 43 includes the mammalian cell of embodiment 42, wherein each of the derepressible promoters comprises a functional promoter and a tetracycline operator sequence (TetO), and the repressor element is a tetracycline repressor protein.

Embodiment 44 includes the mammalian cell of embodiment 43, wherein the expression cassette further comprises a Kruppel-associated box sequence following a sequence encoding the tetracycline repressor protein.

Embodiment 45 includes the mammalian cell of any one of embodiments 34-44, wherein the transposon-specific ITRs are Lepidopteran transposon (PIGGYBAC®) ITRs.

Embodiment 46 includes the mammalian cell of embodiment 35, wherein the gene of interest is a gene of therapeutic interest.

Embodiment 47 is a method of producing a lentiviral vector, comprising: transfecting the mammalian cell of embodiment 34 with a transfer vector, comprising: a nucleic acid sequence encoding a gene of interest under control of a fourth promoter; inducing production of the expression cassette and the nucleic acid; culturing the transfected mammalian cell; and harvesting the lentiviral vector.

Embodiment 48 is a method of producing a lentiviral vector, comprising: inducing production of the chromosomally integrated nucleic acid sequence and the chromosomally integrated nucleic acid sequence encoding a gene of interest of the mammalian of embodiment 35; culturing the mammalian cell; and harvesting the lentiviral vector.

Embodiment 49 includes the method embodiment 47 or embodiment 48, wherein each of the promoters in the expression cassette is a derepressible promoter comprising a functional promoter and a tetracycline operator sequence (TetO), and the repressor element is a tetracycline repressor protein, and the inducing includes adding doxycycline to the mammalian cell.

Embodiment 50 includes the method embodiment 47 or embodiment 48, wherein an amount of the lentiviral vector produced is at least about $10^6$ transduction units/mL two days after the inducing.

Embodiment 51 is a method of treatment with a lentiviral vector, comprising: administering the lentiviral vector produced according to embodiment 47 or embodiment 48 to a mammalian subject.

Embodiment 52 includes the method of embodiment 51, wherein the administering comprises inhalation, injection or intravenous administration.

Embodiment 53 includes the methods of any of embodiments 28-31 and 47-50, wherein at least a portion of the culturing the mammalian cell occurs in the absence of an antibiotic.

Embodiment 54 includes the method of embodiment 53, wherein the portion of the culturing is from passage 3 up to an induction phase.

EXAMPLES

Example 1: Design and Construction of Lentiviral Producer Cell Line

Materials and Methods

To construct a lentiviral producer cell line, two plasmids were designed:
1) A packaging plasmid that expresses GAG-Pol, VSV-G, and Rev in a regulated fashion; and
2) A transfer vector that expresses a gene of interest.

The coding sequence for VSV-G, and Rev is codon-optimized (co) as codon optimization has been proven as one of the most effective ways to increase the protein synthesis without changing the actual amino acid sequence of proteins.

The sequence encoding GAG-Pol is not codon-optimized. All these sequences are put under the control of CMV-TO promoter, the activity of which is repressed in the absence of tetracycline or doxycycline by TetR. In our design, the sequence of Kruppel-associated box (KRAB), which is a transcriptional repression domain from the human zinc finger protein 10, was inserted right after the TetR coding sequence to achieve more tight regulation of CMV-TO.

Addition of doxycycline, upon its binding to TetR, induces a conformation change in TetR to release TetR from CMV-TO. As a result, CMV-TO becomes active and expresses VSV-G, Rev, and GAG-Pol. The regulated expression of VSV-G, Rev, and GAG-Pol minimizes any cytotoxicity associated with these proteins and also, keeps the lentiviral vector production in a basal level before any induction. In order to facilitate the selection process, an antibiotic resistance marker (puromycin) was introduced into this plasmid downstream of the IRES sequence, which was placed right after KRAB sequence. Therefore, human phosphoglycerate promoter drives the expression of TetR-KRAB and puromycin resistance gene altogether.

To test lentiviral vector production, enhanced green fluorescent protein (eGFP) was selected as a gene of interest (GOI). It was put under the CMV promoter for a constitutive expression. Bleomycin resistance marker (BleoR) was introduced in the transfer vector to make the selection process more efficient.

In the traditional approach, the integration of an expression cassettes relies on the random integration events. Therefore, it has not been a controlled, efficient process by nature. Furthermore, the final selected clones can be false-positive (i.e., not expressing the intended GOI) as the fragmented, partial antibiotics marker(s) with incomplete expression cassettes can integrate into the chromosome by chance.

To avoid these unwanted events during the producer cell line generation, all the expression cassettes in the packaging and transfer vector plasmids were flanked by PIGGYBAC® inverted terminal repeat (ITR) sequences. PIGGYBAC® transposase specifically recognizes these ITR sequences to promote a site specific recombination in vivo. Therefore, upon the co-transfection of PIGGYBAC® transposase mRNA, the plasmid region that contains the whole expression cassette is efficiently integrated into the chromosome of the cell.

The schematic of the packaging vector is shown in FIG. 1; the schematic of the transfer vector is shown in FIG. 2. The sequence encoding eGFP with its promoter are shown. Also shown are PIGGYBAC® 5' and 3'ITR. The elements for the production of lentiviral vector such as 5' LTR, HIV-1 ψ, RRE, cPPT/CTS, and 3'LTR are also shown.

The nucleic acid sequence for the packaging vector shown in FIG. 1 is provided below:

(SEQ ID NO: 1)
ATGAGTATTCAACATTTCCGTGTCGCCCTTATTCCCTTTTTTGCGGCATT

TTGCCTTCCTGTTTTTGCTCACCCAGAAACGCTGGTGAAAGTAAAAGATG

CTGAAGATCAGTTGGGTGCACGAGTGGGTTACATCGAACTGGATCTCAAC

AGCGGTAAGATCCTTGAGAGTTTTCGCCCCGAAGAACGTTTTCCAATGAT

GAGCACTTTTAAAGTTCTGCTATGTGGCGCGGTATTATCCCGTATTGACG

CCGGGCAAGAGCAACTCGGTCGCCGCATACACTATTCTCAGAATGACTTG

GTTGAGTACTCACCAGTCACAGAAAAGCATCTTACGGATGGCATGACAGT

AAGAGAATTATGCAGTGCTGCCATAACCATGAGTGATAACACTGCGGCCA

ACTTACTTCTGACAACGATCGGAGGACCGAAGGAGCTAACCGCTTTTTTG

CACAACATGGGGGATCATGTAACTCGCCTTGATCGTTGGGAACCGGAGCT

GAATGAAGCCATACCAAACGACGAGCGTGACACCACGATGCCTGTAGCAA

TGGCAACAACGTTGCGCAAACTATTAACTGGCGAACTACTTACTCTAGCT

TCCCGGCAACAATTAATAGACTGGATGGAGGCGGATAAAGTTGCAGGACC

ACTTCTGCGCTCGGCCCTTCCGGCTGGCTGGTTTATTGCTGATAAATCTG

GAGCCGGTGAGCGTGGGTCTCGCGGTATCATTGCAGCACTGGGGCCAGAT

GGTAAGCCCTCCCGTATCGTAGTTATCTACACGACGGGGAGTCAGGCAAC

TATGGATGAACGAAATAGACAGATCGCTGAGATAGGTGCCTCACTGATTA

AGCATTGGTAACTGTCAGACCAAGTTTACTCATATATACTTTAGATTGAT

TTAAAACTTCATTTTTAATTTAAAAGGATCTAGGTGAAGATCCTTTTTGA

-continued

TAATCTCATGACCAAAATCCCTTAACGTGAGTTTTCGTTCCACTGAGCGT

CAGACCCCGTAGAAAAGATCAAAGGATCTTCTTGAGATCCTTTTTTTCTG

CGCGTAATCTGCTGCTTGCAAACAAAAAAACCACCGCTACCAGCGGTGGT

TTGTTTGCCGGATCAAGAGCTACCAACTCTTTTTCCGAAGGTAACTGGCT

TCAGCAGAGCGCAGATACCAAATACTGTCCTTCTAGTGTAGCCGTAGTTA

GGCCACCACTTCAAGAACTCTGTAGCACCGCCTACATACCTCGCTCTGCT

AATCCTGTTACCAGTGGCTGCTGCCAGTGGCGATAAGTCGTGTCTTACCG

GGTTGGACTCAAGACGATAGTTACCGGATAAGGCGCAGCGGTCGGGCTGA

ACGGGGGGTTCGTGCACACAGCCCAGCTTGGAGCGAACGACCTACACCGA

ACTGAGATACCTACAGCGTGAGCTATGAGAAAGCGCCACGCTTCCCGAAG

GGAGAAAGGCGGACAGGTATCCGGTAAGCGGCAGGGTCGGAACAGGAGAG

CGCACGAGGGAGCTTCCAGGGGGAAACGCCTGGTATCTTTATAGTCCTGT

CGGGTTTCGCCACCTCTGACTTGAGCGTCGATTTTTGTGATGCTCGTCAG

GGGGGCGGAGCCTATGGAAAAACGCCAGCAACGCGGCCTTTTTACGGTTC

CTGGCCTTTTGCTGGCCTTTTGCTCACATGTTCTTTCCTGCGTTATCCCC

TGATTCTGTGGATAACCGTATTACCGCCTTTGAGTGAGCTGATACCGCTC

GCCGCAGCCGAACGACCGAGCGCAGCGAGTCAGTGAGCGAGGAAGCGGAA

GAGCGCCCAATACGCAAACCGCCTCTCCCCGCGCGTTGGCCGATTCATTA

ATGCAGCTGGCACGACAGGTTTCCCGACTGGAAAGCGGGCAGTGAGCGCA

ACGCAATTAATGTGAGTTAGCTCACTCATTAGGCACCCCAGGCTTTACAC

TTTATGCTTCCGGCTCGTATGTTGTGTGGAATTGTGAGCGGATAACAATT

TCACACAGGAAACAGCTATGACCATGATTACGCCAAGCGCGCCCGCCGGG

TAACTCACGGGGTATCCATGTCCATTTCTGCGGCATCCAGCCAGGATACC

CGTCCTCGCTGACGTAATATCCCAGCGCCGCACCGCTGTCATTAATCTGC

ACACCGGCACGGCAGTTCCGGCTGTCGCCGGTATTGTTCGGGTTGCTGAT

GCGCTTCGGGCTGACCATCCGGAACTGTGTCCGGAAAAGCCGCGACGAAC

TGGTATCCCAGGTGGCCTGAACGAACAGTTCACCGTTAAAGGCGTGCATG

GCCACACCTTCCCGAATCATCATGGTAAACGTGCGTTTTCGCTCAACGTC

AATGCAGCAGCAGTCATCCTCGGCAAACTCTTTCCATGCCGCTTCAACCT

CGCGGGAAAAGGCACGGGCTTCTTCCTCCCCGATGCCCAGATAGCGCCAG

CTTGGGCGATGACTGAGCCGGAAAAAGACCCGACGATATGATCCTGATG

CAGCTAGATTAACCCTAGAAAGATAGTCTGCGTAAAATTGACGCATGCAT

TCTTGAAATATTGCTCTCTCTTTCTAAATAGCGCGAATCCGTCGCTGTGC

ATTTAGGACATCTCAGTCGCCGCTTGGAGCTCCCGTGAGGCGTGCTTGTC

AATGCGGTAAGTGTCACTGATTTTGAACTATAACGACCGCGTGAGTCAAA

ATGACGCATGATTATCTTTTACGTGACTTTTAAGATTTAACTCATACGAT

AATTATATTGTTATTTCATGTTCTACTTACGTGATAACTTATTATATATA

TATTTTCTTGTTATAGATATCAAGCTTATCGATACCGTCGACCTCGAGGG

GGGGCCCGGTACCCAATTCGCCCTATAGTGAGTCGTATTAAGATCTAATT

AACCCTCACTAAAGGGAACAAAAGCTGGAGCTCCACCGCGGTGGCGGCCG

CTCTAGAGGGACAGCCCCCCCCCAAAGCCCCCAGGGATGTAATTACGTCC

CTCCCCCGCTAGGGGGCAGCAGCGAGCCGCCCGGGGCTCCGCTCCGGTCC

GGCGCTCCCCCCGCATCCCCGAGCCGGCAGCGTGCGGGGACAGCCCGGGC

ACGGGGAAGGTGGCACGGGATCGCTTTCCTCTGAACGCTTCTCGCTGCTC

TTTGAGCCTGCAGACACCTGGGGGGATACGGGGAAAAAGCCATACCAATG

GGCCCTAAAAAAGGAATCCAGTCAATTCCGGGGCTAAACCTGGCTGCCAC

TGTTTCTTTAGGGACTTCGTTCCTGTGAGGACAccTGCAggCCGGCCGGA

TccTAGgTATacGCGtTAATTAaAGCTTGTTAACGACATTGATTATTGAC

TAGTTATTAATAGTAATCAATTACGGGGTCATTAGTTCATAGCCCATATA

TGGAGTTCCGCGTTACATAACTTACGGTAAATGGCCCGCCTGGCTGACCG

CCCAACGACCCCCGCCCATTGACGTCAATAATGACGTATGTTCCCATAGT

AACGCCAATAGGGACTTTCCATTGACGTCAATGGGTGGAGTATTTACGGT

AAACTGCCCACTTGGCAGTACATCAAGTGTATCATATGCCAAGTACGCCC

CCTATTGACGTCAATGACGGTAAATGGCCCGCCTGGCATTATGCCCAGTA

CATGACCTTATGGGACTTTCCTACTTGGCAGTACATCTACGTATTAGTCA

TCGCTATTACCATGGTGATGCGGTTTTGGCAGTACATCAATGGGCGTGGA

TAGCGGTTTGACTCACGGGGATTTCCAAGTCTCCACCCCATTGACGTCAA

TGGGAGTTTGTTTTGGAACCAAAATCAACGGGACTTTCCAAAATGTCGTA

ACAACTCCGCCCCATTGACGCAAATGGGCGGTAGGCGTGTACGGTGGGAG

GTCTATATAAGCAGAGCTCTCCCTATCAGTGATAGAGATCTCCCTATCAG

TGATAGAGATCGTCGACGAGgtgagtttggggacccttgattgttattat tttcgctattgtaaaattcatgttatatggaggggcaaagttttcaggg tgttgtttagaatgggaagatgtcccttgtatcaccatggaccctcatga taattttgtttctttcactttctactctgttgacaaccattgtctcctct tattttcttttcattttctgtaacttttcgttaaactttagcttgcatt tgtaacgaattttaaattcacttttgtttatttgtcagattgtaagtac tttctctaatcactttttttttcaaggcaatcagggtatattatattgtac ttcagcacagttttagagaacaattgttataattaaatgataaggtagaa tatttctgcatataaattctggctggcgtggaaatattcttattggtaga aacaactacatcctggtcatcatcctgcctttctctttatggttacaatg atatacactgtttgagatgaggataaaatactctgagtccaaaccgggcc cctctgctaaccatgttcatgccttcttctttttcctacagAGACGCCAT

CCACGCTGTTTTGACCTCCTGCCACCATGGCTGGAAGATCTGGCGACTCT

GACGAGGACCTGCTGAAAGCTGTGCGGCTGATCAAGTTCCTGTACCAGAG

CAACCCTCCACCTAATCCTGAGGGCACCAGACAGGCCAGAAGAAACAGGC

GGAGAAGATGGCGCGAGCGGCAGAGACAGATCCACTCCATCTCCGAGCGG

ATCCTGTCCACCTACCTGGGAAGATCCGCTGAGCCTGTTCCTCTGCAGCT

GCCTCCTCTGGAAAGACTGACCCTGGACTGCAACGAGGACTGCGGCACCT

CTGGAACAAGGCGTTGGCTCTCCACAGATCCTGGTGGAAAGCCCCACC

ATCCTGGAATCCGCGCCAAAGAATGAGTTTAAACCGCTGATCAGCCTCG

ACTGTGCCTTCTAGTTGCCAGCCATCTGTTGTTTGCCCCTCCCCCGTGCC

-continued

TTCCTTGACCCTGGAAGGTGCCACTCCCACTGTCCTTTCCTAATAAAATG

AGGAAATTGCATCGCATTGTCTGAGTAGGTGTCATTCTATTCTGGGGGT

GGGGTGGGGCAGGACAGCAAGGGGGAGGATTGGGAAGACAATAGCAGGCA

TGCTGGGGATGCGGTGGGCTCTATGGTACCACAGATTCCCGCTTCTCGAC

TAATTCCTCTTGTACGTGTACTTCGACATGTACCTCCCGTGGCACTTGTT

GGTGGTGAAGTTCACGTGTAGGCTCCCGCTTCCGTTCGGATGCTCCCGT

GGGTCTGGTACTCTTAGTTCCACCAGCTCCCGCCGGGAGAGGGGAAGCGG

AAGCTGTAGGACCGATGGTCGAAGTAGACATTGATTATTGACTAGTTATT

AATAGTAATCAATTACGGGGTCATTAGTTCATAGCCCATATATGGAGTTC

CGCGTTACATAACTTACGGTAAATGGCCCGCCTGGCTGACCGCCCAACGA

CCCCCGCCCATTGACGTCAATAATGACGTATGTTCCCATAGTAACGCCAA

TAGGGACTTTCCATTGACGTCAATGGGTGGAGTATTTACGGTAAACTGCC

CACTTGGCAGTACATCAAGTGTATCATATGCCAAGTACGCCCCCTATTGA

CGTCAATGACGGTAAATGGCCCGCCTGGCATTATGCCCAGTACATGACCT

TATGGGACTTTCCTACTTGGCAGTACATCTACGTATTAGTCATCGCTATT

ACCATGGTGATGCGGTTTTGGCAGTACATCAATGGGCGTGGATAGCGGTT

TGACTCACGGGGATTTCCAAGTCTCCACCCCATTGACGTCAATGGGAGTT

TGTTTTGGAACCAAAATCAACGGGACTTTCCAAAATGTCGTAACAACTCC

GCCCCATTGACGCAAATGGGCGGTAGGCGTGTACGGTGGGAGGTCTATAT

AAGCAGAGCTCTCCCTATCAGTGATAGAGATCTCCCTATCAGTGATAGAG

ATCGTCGACGAGGTAAGTATCAAGGTTACAAGACAGGTTTAAGGAGACCA

ATAGAAACTGGGCTTGTCGAGACAGAGAAGACTCTTGCGTTTCTGATAGG

CACCTATTGGTCTTACTGACATCCACTTTGCCTTTCTCTCCACAGGCGGC

CGCGACACTGCCACCATGAAGTGCCTGCTGTACCTGGCCTTTCTGTTCAT

CGGCGTGAACTGTAAGTTTACCATCGTGTTCCCTCACAATCAGAAGGCA

ACTGGAAGAATGTGCCAAGCAACTACCACTATTGCCCCAGCTCCTCTGAC

CTGAACTGGCACAATGATCTGATCGGCACAGCCCTGCAGGTGAAGATGCC

AAAGAGCCACAAGGCCATCCAGGCAGACGGATGGATGTGCCACGCCTCCA

AGTGGGTGACCACATGTGATTTTCGGTGGTACGGCCCAAAGTATATCACC

CACAGCATCAGATCCTTCACACCCTCTGTGGAGCAGTGCAAGGAGAGCAT

CGAGCAGACAAAGCAGGGCACCTGGCTGAATCCTGGCTTTCCCCCTCAGT

CCTGTGGATACGCAACAGTGACCGACGCAGAGGCCGTGATCGTGCAGGTG

ACCCCACACCACGTGCTGGTGGACGAGTATACAGGCGAGTGGGTGGATTC

CCAGTTCATCAACGGCAAGTGCTCTAATTACATCTGTCCCACCGTGCACA

ACTCCACCACATGGCACTCTGATTATAAGGTGAAGGGCCTGTGCGATTCT

AATCTGATCAGCATGGACATCACATTCTTTTCTGAGGATGGAGAGCTGAG

CTCCCTGGGCAAGGAGGGAACCGGCTTTCGGAGCAACTACTTCGCCTATG

AGACAGGCGGCAAGGCCTGCAAGATGCAGTACTGTAAGCACTGGGCGTG

AGGCTGCCAAGCGGCGTGTGGTTCGAGATGGCCGACAAGGATCTGTTTGC

TGCCGCCAGGTTCCCAGAGTGCCCAGAGGGATCTAGCATCTCTGCCCAA

GCCAGACCTCCGTGGACGTGTCCCTGATCCAGGATGTGGAGCGGATCCTG

GACTACTCCCTGTGCCAGGAGACATGGTCTAAGATCAGAGCCGGCCTGCC

TATCAGCCCAGTGGACCTGTCCTATCTGGCACCAAAGAACCCTGGAACAG

GACCAGCCTTTACCATCATCAATGGCACACTGAAGTACTTCGAGACCCGG

TATATCAGAGTGGACATCGCCGCCCCTATCCTGAGCAGGATGGTGGGCAT

GATCTCCGGAACCACAACCGAGAGGGAGCTGTGGGACGATTGGGCACCTT

ACGAGGATGTGGAGATCGGCCCAAATGGCGTGCTGCGGACCTCCTCTGGC

TACAAGTTTCCCCTGTATATGATCGGCCACGGCATGCTGGACAGCGATCT

GCACCTGAGCTCCAAGGCCCAGGTGTTCGAGCACCCACACATCCAGGACG

CAGCATCTCAGCTGCCTGACGATGAGAGCCTGTTCTTTGGCGATACCGGC

CTGTCCAAGAACCCTATCGAGCTGGTGGAGGGCTGGTTTTCTAGCTGGAA

GTCCTCTATCGCCTCTTTCTTTTTCATCATCGGCCTGATCATCGGCCTGT

TCCTGGTGCTGAGAGTGGGCATCCACCTGTGCATCAAGCTGAAGCACACC

AAGAAGAGGCAGATCTATACAGACATCGAGATGAATCGCCTGGGCAAGTG

ATCTAGACTCGAGCGGCCGCCACTGTGCTGGATATCTGCAGAATTCCACC

ACACTGGACTAGTGGATCCGAGCTCGGTACCAAGCTTAAGTTTAAACCGC

TGATCAGCCTCGACTGTGCCTTCTAGTTGCCAGCCATCTGTTGTTTGCCC

CTCCCCCGTGCCTTCCTTGACCCTGGAAGGTGCCACTCCCACTGTCCTTT

CCTAATAAAATGAGGAAATTGCATCGCATTGTCTGAGTAGGTGTCATTCT

ATTCTGGGGGTGGGGTGGGGCAGGACAGCAAGGGGGAGGATTGGGAAGA

CAATAGCAGGCATGCTGGGGATGCGGTGGGCTCTATGGCATGCCGTCGTC

TTGGAAGTAGTTGGTGTGGGTCCCGTAGGGGCTGAAGAAATTCGTCAGGA

AGGGACTCCCGAAGTGTACCCTCTCTCAGTGGTGTATGCTTCTGCCCCCG

CACGACTGGCGATGGGTCCTGTGGTCGGAGGTCCTGCCGACGGAGTAGAT

GTTGCAGTTCTAGTCTCCCCACTTGAAGGGTAGGTTGCGACATTGATTAT

TGACTAGTTATTAATAGTAATCAATTACGGGGTCATTAGTTCATAGCCCA

TATATGGAGTTCCGCGTTACATAACTTACGGTAAATGGCCCGCCTGGCTG

ACCGCCCAACGACCCCCGCCCATTGACGTCAATAATGACGTATGTTCCCA

TAGTAACGCCAATAGGGACTTTCCATTGACGTCAATGGGTGGAGTATTTA

CGGTAAACTGCCCACTTGGCAGTACATCAAGTGTATCATATGCCAAGTAC

GCCCCCTATTGACGTCAATGACGGTAAATGGCCCGCCTGGCATTATGCCC

AGTACATGACCTTATGGGACTTTCCTACTTGGCAGTACATCTACGTATTA

GTCATCGCTATTACCATGGTGATGCGGTTTTGGCAGTACATCAATGGGCG

TGGATAGCGGTTTGACTCACGGGGATTTCCAAGTCTCCACCCCATTGACG

TCAATGGGAGTTTGTTTTGGAACCAAAATCAACGGGACTTTCCAAAATGT

CGTAACAACTCCGCCCCATTGACGCAAATGGGCGGTAGGCGTGTACGGTG

GGAGGTCTATATAAGCAGAGCTCTCCCTATCAGTGATAGAGATCTCCCTA

TCAGTGATAGAGATCGTCGACGAGGTAAGTATCAAGGTTACAAGACAGGT

TTAAGGAGACCAATAGAAACTGGGCTTGTCGAGACAGAGAAGACTCTTGC

GTTTCTGATAGGCACCTATTGGTCTTACTGACATCCACTTTGCCTTTCTC

TCCACAGGTGTCCACTCCCAGTTCAATTACAGCTCTTAAGGCTAGAGTAC

```
TTAATACGACTCACTATAGGCTAGCCTCGAGAATTCACGCGCACGGCAAG
AGGCGAGGGGCGGCGACTGGTGAGTACGCCAGGATCCGCGGATCCATGGG
CGCCCGCGCCAGCGTGCTGTCCGGCGGCGAGCTGGATAAATGGGAAAAAA
TTCGGTTAAGGCCAGGGGAAAGAAACAATATAAACTAAAACATATAGTA
TGGGCAAGCAGGGAGCTAGAACGATTCGCAGTTAATCCTGGCCTTTTAGA
GACATCAGAAGGCTGTAGACAAATACTGGGACAGCTACAACCATCCCTTC
AGACAGGATCAGAAGAACTTAGATCATTATATAATACAATAGCAGTCCTC
TATTGTGTGCATCAAAGGATAGATGTAAAAGACACCAAGGAAGCCTTAGA
TAAGATAGAGGAAGAGCAAAACAAAAGTAAGAAAAAGGCACAGCAAGCAG
CAGCTGACACAGGAAACAACAGCCAGGTCAGCCAAAATTACCCTATAGTG
CAGAACCTCCAGGGGCAAATGGTACATCAGGCCATATCACCTAGAACTTT
AAATGCATGGGTAAAAGTAGTAGAAGAGAAGGCTTTCAGCCCAGAAGTAA
TACCCATGTTTTCAGCATTATCAGAAGGAGCCACCCCACAAGATTTAAAT
ACCATGCTAAACACAGTGGGGGACATCAAGCAGCCATGCAAATGTTAAA
AGAGACCATCAATGAGGAAGCTGCAGAATGGGATAGATTGCATCCAGTGC
ATGCAGGGCCTATTGCACCAGGCCAGATGAGAGAACCAAGGGGAAGTGAC
ATAGCAGGAACTACTAGTACCCTTCAGGAACAAATAGGATGGATGACACA
TAATCCACCTATCCCAGTAGGAGAAATCTATAAAAGATGGATAATCCTGG
GATTAAATAAAATAGTAAGAATGTATAGCCCTACCAGCATTCTGGACATA
AGACAAGGACCAAAGGAACCCTTTAGAGACTATGTAGACCGATTCTATAA
AACTCTAAGAGCCGAGCAAGCTTCACAAGAGGTAAAAAATTGGATGACAG
AAACCTTGTTGGTCCAAAATGCGAACCCAGATTGTAAGACTATTTTAAAA
GCATTGGGACCAGGAGCGACACTAGAAGAAATGATGACAGCATGTCAGGG
AGTGGGGGGACCCGGCCATAAAGCAAGAGTTTTGGCTGAAGCAATGAGCC
AAGTAACAAATCCAGCTACCATAATGATACAGAAAGGCAATTTTAGGAAC
CAAAGAAAGACTGTTAAGTGTTTCAATTGTGGCAAAGAAGGGCACATAGC
CAAAAATTGCAGGGCCCCTAGGAAAAAGGGCTGTTGGAAATGTGGAAAGG
AAGGACACCAAATGAAAGATTGTACTGAGAGACAGGCTAATTTTTTAGGG
AAGATCTGGCCTTCCCACAAGGGAAGGCCAGGGAATTTTCTTCAGAGCAG
ACCAGAGCCAACAGCCCCACCAGAAGAGAGCTTCAGGTTTGGGGAAGAGA
CAACAACTCCCTCTCAGAAGCAGGAGCCGATAGACAAGGAACTGTATCCT
TTAGCTTCCCTCAGATCACTCTTTGGCAGCGACCCCTCGTCACAATAAAG
ATAGGGGGGCAATTAAAGGAAGCTCTATTAGATACAGGAGCAGATGATAC
AGTATTAGAAGAAATGAATTTGCCAGGAAGATGGAAACCAAAAATGATAG
GGGGAATTGGAGGTTTTATCAAAGTAaGACAGTATGATCAGATACTCATA
GAAATCTGCGGACATAAAGCTATAGGTACAGTATTAGTAGGACCTACACC
TGTCAACATAATTGGAAGAAATCTGTTGACTCAGATTGGCTGCACTTTAA
ATTTTCCCATTAGTCCTATTGAGACTGTACCAGTAAAATTAAAGCCAGGA
ATGGATGGCCCAAAAGTTAAACAATGGCCATTGACAGAAGAAAAAATAAA
AGCATTAGTAGAAATTTGTACAGAAATGGAAAAGGAAGGAAAAATTTCAA
AAATTGGGCCTGAAAATCCATACAATACTCCAGTATTTGCCATAAAGAAA
AAAGACAGTACTAAATGGAGAAAATTAGTAGATTTCAGAGAACTTAATAA
GAGAACTCAAGATTTCTGGGAAGTTCAATTAGGAATACCACATCCTGCAG
GGTTAAAACAGAAAAAATCAGTAACAGTACTGGATGTGGGCGATGCATAT
TTTTCAGTTCCCTTAGATAAAGACTTCAGGAAGTATACTGCATTTACCAT
ACCTAGTATAAACAATGAGACACCAGGGATTAGATATCAGTACAATGTGC
TTCCACAGGGATGGAAAGGATCACCAGCAATATTCCAGTGTAGCATGACA
AAAATCTTAGAGCCTTTTAGAAAACAAAATCCAGACATAGTTATCTATCA
ATACATGGATGATTTGTATGTAGGATCTGACTTAGAAATAGGGCAGCATA
GAACAAAAATAGAGGAACTGAGACAACATCTGTTGAGGTGGGGATTTACC
ACACCAGACAAAAAACATCAGAAAGAACCTCCATTCCTTTGGATGGGTTA
TGAACTCCATCCTGATAAATGGACAGTACAGCCTATAGTGCTGCCAGAAA
AGGACAGCTGGACTGTCAATGACATACAGAAATTAGTGGGAAAATTGAAT
TGGGCAAGTCAGATTTATGCAGGGATTAAAGTAAGGCAATTATGTAAACT
TCTTAGGGGAACCAAAGCACTAACAGAAGTAGTACCACTAACAGAAGAAG
CAGAGCTAGAACTGGCAGAAAACAGGGAGATTCTAAAAGAACCGGTACAT
GGAGTGTATTATGACCCATCAAAAGACTTAATAGCAGAAATACAGAAGCA
GGGGCAAGGCCAATGGACATATCAAATTTATCAAGAGCCATTTAAAAATC
TGAAAACAGGAAAgTATGCAAGAATGAAGGGTGCCCACACTAATGATGTG
AAACAATTAACAGAGGCAGTACAAAAAATAGCCACAGAAAGCATAGTAAT
ATGGGGAAAGACTCCTAAATTTAAATTACCCATACAAAAGGAAACATGGG
AAGCATGGTGGACAGAGTATTGGCAAGCCACCTGGATTCCTGAGTGGGAG
TTTGTCAATACCCCTCCCTTAGTGAAGTTATGGTACCAGTTAGAGAAAGA
ACCCATAATAGGAGCAGAAACTTTCTATGTAGATGGGGCAGCCAATAGGG
AAACTAAATTAGGAAAAGCAGGATATGTAACTGACAGAGGAAGACAAAAA
GTTGTCCCCCTAACGGACACAACAAATCAGAAGACTGAGTTACAAGCAAT
TCATCTAGCTTTGCAGGATTCGGGATTAGAAGTAAACATAGTGACAGACT
CACAATATGCATTGGGAATCATTCAAGCACAACCAGATAAGAGTGAATCA
GAGTTAGTCAGTCAAATAATAGAGCAGTTAATAAAAAAGGAAAAAGTCTA
CCTGGCATGGGTACCAGCACACAAAGGAATTGGAGGAAATGAACAAGTAG
ATAAATTGGTCAGTGCTGGAATCAGGAAAGTACTATTTTTAGATGGAATA
GATAAGGCCCAAGAAGAACATGAGAAATATCACAGTAATTGGAGAGCAAT
GGCTAGTGATTTTAACCTACCACCTGTAGTAGCAAAAGAAATAGTAGCCA
GCTGTGATAAATGTCAGCTAAAAGGGGAAGCCATGCATGGACAAGTAGAC
TGTAGCCCAGGAATATGGCAGCTAGATTGTACACATTTAGAAGGAAAAGT
TATCTTGGTAGCAGTTCATGTAGCCAGTGGATATATAGAAGCAGAAGTAA
TTCCAGCAGAGACAGGGCAAGAAACAGCATACTTCCTCTTAAAATTAGCA
GGAAGATGGCCAGTAAAAACAGTACATACAGACAATGGCAGCAATTTCAC
CAGTACTACAGTTAAGGCCGCCTGTTGGTGGGCGGGATCAAGCAGGAAT
TTGGCATTCCCTACAATCCCCAAAGTCAAGGAGTAATAGAATCTATGAAT
AAAGAATTAAAGAAAATTATAGGACAGGTAAGAGATCAGGCTGAACATCT
```

-continued

TAAGACAGCAGTACAAATGGCAGTATTCATCCACAATTTTAAAAGAAAAG

GGGGGATTGGGGGGTACAGTGCAGGGGAAAGAATAGTAGACATAATAGCA

ACAGACATACAAACTAAAGAATTACAAAAACAAATTACAAAAATTCAAAA

TTTTCGGGTTTATTACAGGGACAGCAGAGATCCAGTTTGGAAAGGACCAG

CAAAGCTCCTCTGGAAAGGTGAAGGGCAGTAGTAATACAAGATAATAGT

GACATAAAGTAGTGCCAAGAAGAAAAGCAAAGATCATCAGGGATTATGG

AAAACAGATGGCAGGTGATGATTGTGTGGCAAGTAGACAGGATGAGGATT

AACACCCATAGAATGGCCAAGGCAAAGAGAAGAGTGGTGCAGAGAGAAA

AAGAGCAGTGGGAATAGGAGCTTTGTTCCTTGGGTTCTTGGGAGCAGCAG

GAAGCACTATGGGCGCAGCGTCAATGACGCTGACGGTACAGGCCAGACAA

TTATTGTCTGATATAGTGCAGCAGCAGAACAATTTGCTGAGGGCTATTGA

GGCGCAACAGCATCTGTTGCAACTCACAGTCTGGGGCATCAAACAGCTCC

AGGCAAGAATCCTGGCTGTGGAAAGATACCTAAAGGATCAACAGCTCCTG

GGGATTTGGGGTTGCTCTGGAAAACTCATTTGCACCACTGCTGTGCCGCG

GCCGCAAAAAGGGGCTCGTCCCTGTTTCCGGAGGAATTTGCAAGCGGGG

TCTTGCATGACGGGGAGGCAAACCCCCGTTCGGCCGCAGTCCGGCCGGCC

CGAGACTCGAACCGGGGGTCCTGCGACTCAACCCTTGGAAAATAACCCTC

CGGCTACAGGGAGCGAGCCACTTAATGCTTTCGCTTTCCAGCCTAACCGC

TTACGCCGCGCGCGgCCAGTGGCCAAAAAAGCTAGCGCAGCAGCCGCCGC

GCCTGGAAGGAAGCCAAAAGGAGCGCTCCCCCGTTGTCTGACGTCGCACA

CCTGGGTTCGACACGCGGGCGGTAACCGCATGGATCACGCGGACGGCCG

GATCCGGGGTTCGAACCCCGGTCGTCCGCCATGATACCCTTGCGAATTTA

TCCACCAGACCACGGAAGAGTGCCCGCGGCCGCTTCGAGCAGACATGATA

AGATACATTGATGAGTTTGGACAAACCACAACTAGAATGCAGTGAAAAAA

ATGCTTTATTTGTGAAATTTGTGATGCTATTGCTTTATTTGTAACCATTA

TAAGCTGCAATAAACAAGTTCGGGACACTACGTCTTCTTTTGTGAGCCGA

CCCTCCGGTTGTGGCTCTACGACATGGGGCGACTGCCGCCGGACCTTCCG

TCTTCGCTGTACCGGGACTTCGAGCACCCGCCCCCGGTGGACTAGACGTT

GAAGTTCTGGTGTATGTCTAGGTTCTTTGGGCGATTCTTGGAGTTCTACG

GGCCGCAGATGATACACCTGggggttggggttgcgccttttccaaggcag ccctgggtttgcgcagggacgcggctgctctgggcgtggttccgggaaac gcagcggcgccgaccctgggtctcgcacattcttcacgtccgttcgcagc gtcaccggatcttcgccgctaccttgtgggccccccggcgacgcttcc tgctccgcccctaagtcgggaaggttccttgcggttcgcggcgtgccgga cgtgacaaacggaagccgcacgtctcactagtaccctcgcagacggacag cgccagggagcaatggcagcgcgccgaccgcgatgggctgtggccaatag cggctgctcagcagggcgcgccgagagcagcggccgggaaggggcggtgc gggaggcggggtgtggggcggtagtgtgggccctgttcctgcccgcgcgg tgttccgcattctgcaagcctccggagcgcacgtcggcagtcggctccct cgttgaccgaatcaccgacctctctccccaggggGatctGTAAGTATCAA -continued

GGTTACAAGACAGGTTTAAGGAGACCAATAGAAACTGGGCTTGTCGAGAC

AGAGAAGACTCTTGCGTTTCTGATAGGCACCTATTGGTCTTACTGACATC

CACTTTGCCTTTCTCTCCACAGctcctgggcaacgtgctggttattgtgc tgtctcatcattttggcaaagaattgtaatacgactcactatagggcgaG CCACCatggctagattagataaaagtaaagtgattaacagcgcattagag ctgcttaatgaggtcggaatcgaaggttaacaacccgtaaactcgccca gaagctaggtgtagagcagcctacattgtattggcatgtaaaaaataagc gggcttgctcgacgccttagccattgagatgttagataggcaccatact cacttttgcccttagaaggggaaagctggcaagattttttacgtaataa cgctaaaagttttagatgtgctttactaagtcatcgcgatggagcaaaag tacatttaggtacacggcctacagaaaaacagtatgaaactctcgaaaat caattagccttttatgccaacaaggttttttcactagagaatgcCttata tgcactcagcgcCgtggggcattttactttaggttgcgtattggaagatc aagagcatcaagtcgctaaagaagaaagggaaacacctactactgatagt atgccgccattattacgacaagctatcgaattatttgatcaccaaggtgc agagccagccttatattcggccttgaattgatcatatgcggattagaaaa acaactaaatgtgaaagtgggtccccaaaaaagaagagaaaggtcgacg gcggtggtgctttgtctcctcagcactctgctgtcactcaaggaagtatc atcaagaacaaggagggcatggatgctaagtcactaactgcctggtcccg gacactggtgaccttcaaggatgtatttgtggacttcaccagggaggagt ggaagctgctggacactgctcagcagatcgtgtacagaaatgtgatgctg gagaactataagaacctggtttccttgggttatcagcttactaagccaga tgtgatcctccggttggagaagggagaagagccctggctggtggagagag aaattcaccaagagacccatcctgattcagagactgcatttgaaatcaaa tcatcagtttaagcgtacagcggctcccgggagttctagggatctgcccc tctccctccccccccctaacgttactggccgaagccgcttggaataagg ccggtgtgcgtttgtctatatgttattttccaccatattgccgtcttttg gcaatgtgagggcccggaaacctggccctgtcttcttgacgagcattcct aggggtattcccctctcgccaaaggaatgcaaggtctgttgaatgtcgtg aaggaagcagttcctctggaagcttcttgaagacaaacaacgtctgtagc gacccttgcaggcagcggaaccccccacctggcgacaggtgcctctgcg gccaaaagccacgtgtataagatacacctgcaaaggcggcacaacccag tgccacgttgtgagttggatagttgtggaaagagtcaaatggctctcctc aagcgtattcaacaaggggctgaaggatgcccagaaggtaccccattgta tgggatctgatctggggcctcggtgcacatgctttacatgtgtttagtcg aggttaaaaaaacgtctaggcccccgaaccacggggacgtggttttcct ttgaaaaacacgatgataaggatccaccggagGCCACCatgaccgagtac aagcccacggtgcgcctcgccacccgcgacgacgtccccagggccgtacg caccctcgccgccgcgttcgccgactaccccgccacgcgccacaccgtcg atccggaccgccacatcgagcgggtcaccgagctgcaagaactcttcctc acgcgcgtcgggctcgacatcggcaaggtgtgggtcgcggacgacggcgc cgcggtggcggtctggaccacgccggagagcgtcgaagcggggcggtgt
tcgccgagatcggcccgcgcatggccgagttgagcggttcccggctggcc
gcgcagcaacagatggaaggcctcctggcgccgcaccggcccaaggagcc
cgcgtggttcctggccaccgtcggcgtctcgcccgaccaccagggcaagg
gtctgggcagcgccgtcgtgctccccggagtggaggcggccgagcgcgcc
ggggtgcccgccttcctggagacctccgcgccccgcaacctcccccttcta
cgagcggctcggcttcaccgtcaccgccgacgtcgaggtgcccgaaggac
cgcgcacctggtgcatgacccgcaagcccggtgcctgaCCGCGTCTGGAA
CatgcatCGGTACCTTTAAGACCAATGACTTACAAGGCAGCTGTAGATCT
TAGCCACTTTTTAAAAGAAAAGGGGGGACGTAGTAGTTCATGTCATCTTA
TTATTCAGTATTTATAACTTGCAAAGAAATGAATATCAGAGAGTGAGAGG
AACTTGTTTATTGCAGCTTATAATGGTTACAAATAAAGCAATAGCATCAC
AAATTTCACAAATAAAGCATTTTTTTCACTGCATTCTAGTTGTGGTTTGT
CCAAACTCATCAATGTATCTTAGTTAACGAATTCGGCGCGCcAATtgATC
aGCGctTAAgCTAgcGATCgcGGGACTTTCCACACCCTAACTGACACACA
TTCCACAGAATTCCCATCACAAAGCTCTGACCTCAATCCTATAGAAGGA
GGAATGAGCCAAAATTCACCCAACTTATTGTGGGAAGCTGGCCTTGGAGG
CCTTTTCCCCGTATCCCCCAGGTGTCTGCAGGCTCAAAGAGCAGCGAGA
AGCGTTCAGAGGAAAGCGATCCCGTGCCACCTTCCCCGTGCCCGGCTGT
CCCCGCACGCTGCCGGCTCGGGGATGCGGGGGAGCGCCGGACCGGAGCG
GAGCCCCGGGCGGCTCGCTGCTGCCCCCTAGCGGGGAGGGACGTAATTA
CATCCCTGGGGCTTTGGGGGGGGCTGTCCCTCTAGAACTAGTGGATCC
CCCGGGCTGCAGGAATTCGATAAAAGTTTTGTTACTTTATAGAAGAAATT
TTGAGTTTTTGTTTTTTTTAATAAATAAATAAACATAAATAAATTGTTT
GTTGAATTTATTATTAGTATGTAAGTGTAAATATAATAAAACTTAATATC
TATTCAAATTAATAAATAAACCTCGATATACAGACCGATAAAACACATGC
GTCAATTTTACGCATGATTATCTTTAACGTACGTCACAATATGATTATCT
TTCTAGGGTTAATCTAGCTGCGTGTTCTGCAGCGTGTCGAGCATCTTCAT
CTGCTCCATCACGCTGTAAAACACATTTGCACCGCGAGTCTGCCCGTCCT
CCACGGGTTCAAAAACGTGAATGAACGAGGCGCGCTCACTGGCCGTCGTT
TTACAACGTCGTGACTGGGAAAACCCTGGCGTTACCCAACTTAATCGCCT
TGCAGCACATCCCCCTTTCGCCAGCTGGCGTAATAGCGAAGAGGCCCGCA
CCGATCGCCCTTCCCAACAGTTGCGCAGCCTGAATGGCGAATGGGACGCG
CCCTGTAGCGGCGCATTAAGCGCGGCGGGTGTGGTGGTTACGCGCAGCGT
GACCGCTACACTTGCCAGCGCCCTAGCGCCCGCTCCTTTCGCTTTCTTCC
CTTCCTTTCTCGCCACGTTCGCCGGCTTTCCCCGTCAAGCTCTAAATCGG
GGGCTCCCTTTAGGGTTCCGATTTAGTGCTTTACGGCACCTCGACCCCAA
AAAACTTGATTAGGGTGATGGTTCACGTAGTGGGCCATCGCCCTGATAGA
CGGTTTTTCGCCCTTTGACGTTGGAGTCCACGTTCTTTAATAGTGGACTC
TTGTTCCAAACTGGAACAACACTCAACCCTATCTCGGTCTATTCTTTTGA
TTTATAAGGGATTTTGCCGATTTCGGCCTATTGGTTAAAAAATGAGCTGA
TTTAACAAAAATTTAACGCGAATTTTAACAAAATATTAACGCTTACAATT
TAGGTGGCACTTTTCGGGGAAATGTGCGCGGAACCCCTATTTGTTTATTT
TTCTAAATACATTCAAATATGTATCCGCTCATGAGACAATAACCCTGATA
AATGCTTCAATAATATTGAAAAGGAAGAGT The nucleic acid sequence for the transfer vector shown in FIG. 2 is provided below:

(SEQ ID NO: 2)
ATGAGTATTCAACATTTCCGTGTCGCCCTTATTCCCTTTTTTGCGGCATT
TTGCCTTCCTGTTTTTGCTCACCCAGAAACGCTGGTGAAAGTAAAAGATG
CTGAAGATCAGTTGGGTGCACGAGTGGGTTACATCGAACTGGATCTCAAC
AGCGGTAAGATCCTTGAGAGTTTTCGCCCCGAAGAACGTTTTCCAATGAT
GAGCACTTTTAAAGTTCTGCTATGTGGCGCGGTATTATCCCGTATTGACG
CCGGGCAAGAGCAACTCGGTCGCCGCATACACTATTCTCAGAATGACTTG
GTTGAGTACTCACCAGTCACAGAAAAGCATCTTACGGATGGCATGACAGT
AAGAGAATTATGCAGTGCTGCCATAACCATGAGTGATAACACTGCGGCCA
ACTTACTTCTGACAACGATCGGAGGACCGAAGGAGCTAACCGCTTTTTTG
CACAACATGGGGGATCATGTAACTCGCCTTGATCGTTGGGAACCGGAGCT
GAATGAAGCCATACCAAACGACGAGCGTGACACCACGATGCCTGTAGCAA
TGGCAACAACGTTGCGCAAACTATTAACTGGCGAACTACTTACTCTAGCT
TCCCGGCAACAATTAATAGACTGGATGGAGGCGGATAAAGTTGCAGGACC
ACTTCTGCGCTCGGCCCTTCCGGCTGGCTGGTTTATTGCTGATAAATCTG
GAGCCGGTGAGCGTGGGTCTCGCGGTATCATTGCAGCACTGGGGCCAGAT
GGTAAGCCCTCCCGTATCGTAGTTATCTACACGACGGGGAGTCAGGCAAC
TATGGATGAACGAAATAGACAGATCGCTGAGATAGGTGCCTCACTGATTA
AGCATTGGTAACTGTCAGACCAAGTTTACTCATATATACTTTAGATTGAT
TTAAAACTTCATTTTTAATTTAAAAGGATCTAGGTGAAGATCCTTTTTGA
TAATCTCATGACCAAAATCCCTTAACGTGAGTTTTCGTTCCACTGAGCGT
CAGACCCCGTAGAAAAGATCAAAGGATCTTCTTGAGATCCTTTTTTTCTG
CGCGTAATCTGCTGCTTGCAAACAAAAAAACCACCGCTACCAGCGGTGGT
TTGTTTGCCGGATCAAGAGCTACCAACTCTTTTTCCGAAGGTAACTGGCT
TCAGCAGAGCGCAGATACCAAATACTGTCCTTCTAGTGTAGCCGTAGTTA
GGCCACCACTTCAAGAACTCTGTAGCACCGCCTACATACCTCGCTCTGCT
AATCCTGTTACCAGTGGCTGCTGCCAGTGGCGATAAGTCGTGTCTTACCG
GGTTGGACTCAAGACGATAGTTACCGGATAAGGCGCAGCGGTCGGGCTGA
ACGGGGGGTTCGTGCACACAGCCCAGCTTGGAGCGAACGACCTACACCGA
ACTGAGATACCTACAGCGTGAGCTATGAGAAAGCGCCACGCTTCCCGAAG
GGAGAAAGGCGGACAGGTATCCGGTAAGCGGCAGGGTCGGAACAGGAGAG
CGCACGAGGGAGCTTCCAGGGGGAAACGCCTGGTATCTTTATAGTCCTGT
CGGGTTTCGCCACCTCTGACTTGAGCGTCGATTTTTGTGATGCTCGTCAG
GGGGGCGGAGCCTATGGAAAAACGCCAGCAACGCGGCCTTTTTACGGTTC

CTGGCCTTTTGCTGGCCTTTTGCTCACATGTTCTTTCCTGCGTTATCCCC

TGATTCTGTGGATAACCGTATTACCGCCTTTGAGTGAGCTGATACCGCTC

GCCGCAGCCGAACGACCGAGCGCAGCGAGTCAGTGAGCGAGGAAGCGGAA

GAGCGCCCAATACGCAAACCGCCTCTCCCCGCGCGTTGGCCGATTCATTA

ATGCAGCTGGCACGACAGGTTTCCCGACTGGAAAGCGGGCAGTGAGCGCA

ACGCAATTAATGTGAGTTAGCTCACTCATTAGGCACCCCAGGCTTTACAC

TTTATGCTTCCGGCTCGTATGTTGTGTGGAATTGTGAGCGGATAACAATT

TCACACAGGAAACAGCTATGACCATGATTACGCCAAGCGCGCCCGCCGGG

TAACTCACGGGGTATCCATGTCCATTTCTGCGGCATCCAGCCAGGATACC

CGTCCTCGCTGACGTAATATCCCAGCGCCGCACCGCTGTCATTAATCTGC

ACACCGGCACGGCAGTTCCGGCTGTCGCCGGTATTGTTCGGGTTGCTGAT

GCGCTTCGGGCTGACCATCCGGAACTGTGTCCGGAAAAGCCGCGACGAAC

TGGTATCCCAGGTGGCCTGAACGAACAGTTCACCGTTAAAGGCGTGCATG

GCCACACCTTCCCGAATCATCATGGTAAACGTGCGTTTTCGCTCAACGTC

AATGCAGCAGCAGTCATCCTCGGCAAACTCTTTCCATGCCGCTTCAACCT

CGCGGGAAAGGCACGGGCTTCTTCCTCCCCGATGCCCAGATAGCGCCAG

CTTGGGCGATGACTGAGCCGGAAAAAAGACCCGACGATATGATCCTGATG

CAGCTAGATTAACCCTAGAAAGATAGTCTGCGTAAAATTGACGCATGCAT

TCTTGAAATATTGCTCTCTCTTTCTAAATAGCGCGAATCCGTCGCTGTGC

ATTTAGGACATCTCAGTCGCCGCTTGGAGCTCCCGTGAGGCGTGCTTGTC

AATGCGGTAAGTGTCACTGATTTTGAACTATAACGACCGCGTGAGTCAAA

ATGACGCATGATTATCTTTTACGTGACTTTTAAGATTTAACTCATACGAT

AATTATATTGTTATTTCATGTTCTACTTACGTGATAACTTATTATATATA

TATTTTCTTGTTATAGATATCAAGCTTATCGATACCGTCGACCTCGAGGG

GGGGCCCGGTACCCAATTCGCCCTATAGTGAGTCGTATTAAGATCTAATT

AACCCTCACTAAAGGGAACAAAAGCTGGAGCTCCACCGCGGTGGCGGCCG

CTCTAGAGGGACAGCCCCCCCCCAAAGCCCCCAGGGATGTAATTACGTCC

CTCCCCCGCTAGGGGGCAGCAGCGAGCCGCCCGGGGCTCCGCTCCGGTCC

GGCGCTCCCCCGCATCCCCGAGCCGGCAGCGTGCGGGGACAGCCCGGGC

ACGGGGAAGGTGGCACGGGATCGCTTTCCTCTGAACGCTTCTCGCTGCTC

TTTGAGCCTGCAGACACCTGGGGGGATACGGGGAAAAAGCCATACCAATG

GGCCCTAAAAAAGGAATCCAGTCAATTCCGGGGCTAAACCTGGCTGCCAC

TGTTTCTTTAGGGACTTCGTTCCTGTGAGGACAccTGCAggCCGGCCGGA

TccTAGgtATacGCGtTAATTAaAGCTTGTTAACGACATTGATTATTGAC

TAGTTATTAATAGTAATCAATTACGGGGTCATTAGTTCATAGCCCATATA

TGGAGTTCCGCGTTACATAACTTACGGTAAATGGCCCGCCTGGCTGACCG

CCCAACGACCCCCGCCCATTGACGTCAATAATGACGTATGTTCCCATAGT

AACGCCAATAGGGACTTTCCATTGACGTCAATGGGTGGAGTATTTACGGT

AAACTGCCCACTTGGCAGTACATCAAGTGTATCATATGCCAAGTACGCCC

CCTATTGACGTCAATGACGGTAAATGGCCCGCCTGGCATTATGCCCAGTA

CATGACCTTATGGGACTTTCCTACTTGGCAGTACATCTACGTATTAGTCA

TCGCTATTACCATGGTGATGCGGTTTTGGCAGTACATCAATGGGCGTGGA

TAGCGGTTTGACTCACGGGGATTTCCAAGTCTCCACCCCATTGACGTCAA

TGGGAGTTTGTTTTGGCACCAAAATCAACGGGACTTTCCAAAATGTCGTA

ACAACTCCGCCCCATTGACGCAAATGGGCGGTAGGCGTGTACGGTGGGAG

GTCTATATAAGCAGCGCGTTTTGCCTGTACTGGGTCTCTCTGGTTAGACC

AGATCTGAGCCTGGGAGCTCTCTGGCTAACTAGGGAACCCACTGCTTAAG

CCTCAATAAAGCTTGCCTTGAGTGCTTCAAGTAGTGTGTGCCCGTCTGTT

GTGTGACTCTGGTAACTAGAGATCCCTCAGACCCTTTTAGTCAGTGTGGA

AAATCTCTAGCAGTGGCGCCCGAACAGGGACTTGAAAGCGAAAGGGAAAC

CAGAGGAGCTCTCTCGACGCAGGACTCGGCTTGCTGAAGCGCGCACGGCA

AGAGGCGAGGGCGGCGACTGGTGAGTACGCCAAAAATTTTGACTAGCGG

AGGCTAGAAGGAGAGAGATGGGTGCGAGAGCGTCAGTATTAAGCGGGGA

GAATTAGATCGCGATGGGAAAAAATTCGGTTAAGGCCAGGGGGAAAGAAA

AAATATAAATTAAAACATATAGTATGGGCAAGCAGGGAGCTAGAACGATT

CGCAGTTAATCCTGGCCTGTTAGAAACATCAGAAGGCTGTAGACAAATAC

TGGGACAGCTACAACCATCCCTTCAGACAGGATCAGAAGAACTTAGATCA

TTATATAATACAGTAGCAACCCTCTATTGTGTGCATCAAAGGATAGAGAT

AAAAGACACCAAGGAAGCTTTAGACAAGATAGAGGAAGAGCAAAACAAAA

GTAAGACCACCGCACAGCAAGCGGCCGGCCGCTGATCTTCAGACCTGGAG

GAGGAGATATGAGGGACAATTGGAGAAGTGAATTATATAAATATAAAGTA

GTAAAAATTGAACCATTAGGAGTAGCACCCACCAAGGCAAAGAGAAGAGT

GGTGCAGAGAGAAAAAAGAGCAGTGGGAATAGGAGCTTTGTTCCTTGGGT

TCTTGGGAGCAGCAGGAAGCACTATGGGCGCAGCGTCAATGACGCTGACG

GTACAGGCCAGACAATTATTGTCTGGTATAGTGCAGCAGCAGAACAATTT

GCTGAGGGCTATTGAGGCGCAACAGCATCTGTTGCAACTCACAGTCTGGG

GCATCAAGCAGCTCCAGGCAAGAATCCTGGCTGTGGAAAGATACCTAAAG

GATCAACAGCTCCTGGGGATTTGGGGTTGCTCTGGAAAACTCATTTGCAC

CACTGCTGTGCCTTGGAATGCTAGTTGGAGTAATAAATCTCTGGAACAGA

TTTGGAATCACACGACCTGGATGGAGTGGGACAGAGAAATTAACAATTAC

ACAAGCTTAATACACTCCTTAATTGAAGAATCGCAAAACCAGCAAGAAAA

GAATGAACAAGAATTATTGGAATTAGATAAATGGGCAAGTTTGTGGAATT

GGTTTAACATAACAAATTGGCTGTGGTATATAAAATTATTCATAATGATA

GTAGGAGGCTTGGTAGGTTTAAGAATAGTTTTTGCTGTACTTTCTATAGT

GAATAGAGTTAGGCAGGGATATTCACCATTATCGTTTCAGACCCACCTCC

CAACCCCGAGGGGACCCGACAGGCCCGAAGGAATAGAAGAAGAAGGTGGA

GAGAGAGACAGAGACAGATCCATTCGATTAGTGAACGGATCGGCACTGCG

TGCGCCAATTCTGCAGACAAATGGCAGTATTCATCCACAATTTTAAAAGA

AAAGGGGGGATTGGGGGGTACAGTGCAGGGGAAAGAATAGTAGACATAAT

AGCAACAGACATACAAACTAAAGAATTACAAAAACAAATTACAAAAATTC

AAAATTTTCGGGTTTATTACAGGGACAGCAGAGATCCAGTTTGGTTAGTA

-continued

CCGGGCCCGCTCTAGAGATCCGACGCGCCATCTCTAGGCCCGCGCCGGCC
CCCTCGCACAGACTTGTGGGAGAAGCTCGGCTACTCCCCTGCCCCGGTTA
ATTTGCATATAATATTTCCTAGTAACTATAGAGGCTTAATGTGCGATAAA
AGACAGATAATCTGTTCTTTTTAATACTAGCTACATTTTACATGATAGGC
TTGGATTTCTATAAGAGATACAAATACTAAATTATTATTTTAAAAAACAG
CACAAAAGGAAACTCACCCTAACTGTAAAGTAATTGTGTGTTTTGAGACT
ATAAATATCCCTTGGAGAAAAGCCTTGTTAACGCGCGGTGACCCTCGAGG
TCGACGGTATCGATAAGCTCGCTTCACGAGATTCCAGCAGGTCGAGGGAC
CTAATAACTTCGTATAGCATACATTATACGAAGTTATATTAAGGGTTCCA
AGCTTAAGCGGCCGCGTGGATAACCGTATTACCGCCATGCATTAGTTATT
AATAGTAATCAATTACGGGGTCATTAGTTCATAGCCCATATATGGAGTTC
CGCGTTACATAACTTACGGTAAATGGCCCGCCTGGCTGACCGCCCAACGA
CCCCCGCCCATTGACGTCAATAATGACGTATGTTCCCATAGTAACGCCAA
TAGGGACTTTCCATTGACGTCAATGGGTGGAGTATTTACGGTAAACTGCC
CACTTGGCAGTACATCAAGTGTATCATATGCCAAGTACGCCCCCTATTGA
CGTCAATGACGGTAAATGGCCCGCCTGGCATTATGCCCAGTACATGACCT
TATGGGACTTTCCTACTTGGCAGTACATCTACGTATTAGTCATCGCTATT
ACCATGGTGATGCGGTTTTGGCAGTACATCAATGGGCGTGGATAGCGGTT
TGACTCACGGGGATTTCCAAGTCTCCACCCCATTGACGTCAATGGGAGTT
TGTTTTGGCACCAAAATCAACGGGACTTTCCAAAATGTCGTAACAACTCC
GCCCCATTGACGCAAATGGGCGGTAGGCGTGTACGGTGGAGGTCTATAT
AAGCAGAGCTGGTTTAGTGAACCGTCAGATCCGCTAGCGCTACCGGTCGC
CACCATGGTGAGCAAGGGCGAGGAGCTGTTCACCGGGGTGGTGCCCATCC
TGGTCGAGCTGGACGGCGACGTAAACGGCCACAAGTTCAGCGTGTCCGGC
GAGGGCGAGGGCGATGCCACCTACGGCAAGCTGACCCTGAAGTTCATCTG
CACCACCGGCAAGCTGCCCGTGCCCTGGCCCACCCTCGTGACCACCCTGA
CCTACGGCGTGCAGTGCTTCAGCCGCTACCCCGACCACATGAAGCAGCAC
GACTTCTTCAAGTCCGCCATGCCCGAAGGCTACGTCCAGGAGCGCACCAT
CTTCTTCAAGGACGACGGCAACTACAAGACCCGCGCCGAGGTGAAGTTCG
AGGGCGACACCCTGGTGAACCGCATCGAGCTGAAGGGCATCGACTTCAAG
GAGGACGGCAACATCCTGGGGCACAAGCTGGAGTACAACTACAACAGCCA
CAACGTCTATATCATGGCCGACAAGCAGAAGAACGGCATCAAGGTGAACT
TCAAGATCCGCCACAACATCGAGGACGGCAGCGTGCAGCTCGCCGACCAC
TACCAGCAGAACACCCCCATCGGCGACGGCCCCGTGCTGCTGCCCGACAA
CCACTACCTGAGCACCCAGTCCGCCCTGAGCAAAGACCCCAACGAGAAGC
GCGATCACATGGTCCTGCTGGAGTTCGTGACCGCCGCCGGGATCACTCTC
GGCATGGACGAGCTGTACAAGTAGGAATTCGTCGAGGGACCTAATAACTT
CGTATAGCATACATTATACGAAGTTATACATGTTTAAGGGTTCCGGTTCC
ACTAGGTACAATTCGATATCAAGCTTATCGATAATCAACCTCTGGATTAC
AAAATTTGTGAAAGATTGACTGGTATTCTTAACTATGTTGCTCCTTTTAC

GCTATGTGGATACGCTGCTTTAATGCCTTTGTATCATGCTATTGCTTCCC
GTATGGCTTTCATTTTCTCCTCCTTGTATAAATCCTGGTTGCTGTCTCTT
TATGAGGAGTTGTGGCCCGTTGTCAGGCAACGTGGCGTGGTGTGCACTGT
GTTTGCTGACGCAACCCCCACTGGTTGGGGCATTGCCACCACCTGTCAGC
TCCTTTCCGGGACTTTCGCTTTCCCCCTCCCTATTGCCACGGCGGAACTC
ATCGCCGCCTGCCTTGCCCGCTGCTGGACAGGGGCTCGGCTGTTGGGCAC
TGACAATTCCGTGGTGTTGTCGGGGAAATCATCGTCCTTTCCTTGGCTGC
TCGCCTGTGTTGCCACCTGGATTCTGCGCGGGACGTCCTTCTGCTACGTC
CCTTCGGCCCTCAATCCAGCGGACCTTCCTTCCCGCGGCCTGCTGCCGGC
TCTGCGGCCTCTTCCGCGTCTTCGCCTTCGCCCTCAGACGAGTCGGATCT
CCCTTTGGGCCGCCTCCCCGCATCGATACCGTCGACCTCGATCGAGACCT
AGAAAACATGGAGCAATCACAAGTAGCAATACAGCAGCTACCAATGCTG
ATTGTGCCTGGCTAGAAGCACAAGAGGAGGAGGAGGTGGGTTTTCCAGTC
ACACCTCAGGTACCTTTAAGACCAATGACTTACAAGGCAGCTGTAGATCT
TAGCCACTTTTTAAAAGAAAAGGGGGGACTGGAAGGGCTAATTCACTCCC
AACGAAGACAAGATATCCTTGATCTGTGGATCTACCACACACAAGGCTAC
TTCCCTGATTGGCAGAACTACACACCAGGGCCAGGGATCAGATATCCACT
GACCTTTGGATGGTGCTACAAGCTAGTACCAGTTGAGCAAGAGAAGGTAG
AAGAAGCCAATGAAGGAGAGAACACCCGCTTGTTACACCCTGTGAGCCTG
CATGGGATGGATGACCCGGAGAGAGAAGTATTAGAGTGGAGGTTTGACAG
CCGCCTAGCATTTCATCACATGGCCCGAGAGCTGCATCCGGACTGTACTG
GGTCTCTCTGGTTAGACCAGATCTGAGCCTGGGAGCTCTCTGGCTAACTA
GGGAACCCACTGCTTAAGCCTCAATAAAGCTTGCCTTGAGTGCTTCAAGT
AGTGTGTGCCCGTCTGTTGTGTGACTCTGGTAACTAGAGATCCCTCAGAC
CCTTTTAGTCAGTGTGGAAAATCTCTAGCAGTTAACGAATTCGGCGCGCc
AATtgATCaGCGctTAAgCTAgcGATCgcGGGACTTTCCACACCCTAACT
GACACACATTCCACAGAATTCCCATCACAAAGCTCTGACCTCAATCCTAT
AGAAAGGAGGAATGAGCCAAAATTCACCCAACTTATTGTGGGAAGCTGGC
CTTGGAGGCCTGTGTGTCAGTTAGGGTGTGGAAAGTCCCCAGGCTCCCCA
GGCAGGCAGAAGTATGCAAAGCATGCATCTCAATTAGTCAGCAACCAGGT
GTGGAAAGTCCCCAGGCTCCCCAGCAGGCAGAAGTATGCAAAGCATGCAT
CTCAATTAGTCAGCAACCATAGTCCCGCCCCTAACTCCGCCCATCCCGCC
CCTAACTCCGCCCAGTTCCGCCCATTCTCCGCCCCATGGCTGACTAATTT
TTTTTATTTATGCAGAGGCCGAGGCCGCCTCTGCCTCTGAGCTATTCCAG
AAGTAGTGAGGAGGCTTTTTTGGAGGCCTAGGCTTTTGCAAAAAGCTCCC
GGGAGCTTGTATATCCATTTTCGGATCTGATCAGCACGTGTTGACAATTA
ATCATCGGCATAGTATATCGGCATAGTATAATACGACAAGGTGAGGAACT
AAACCATGGCCAAGTTGACCAGTGCCGTTCCGGTGCTCACCGCGCGCGAC
GTCGCCGGAGCGGTCGAGTTCTGGACCGACCGGCTCGGGTTCTCCCGGGA
CTTCGTGGAGGACGACTTCGCCGGTGTGGTCCGGGACGACGTGACCCTGT
TCATCAGCGCGGTCCAGGACCAGGTGGTGCCGGACAACACCCTGGCCTGG

-continued

```
GTGTGGGTGCGCGGCCTGGACGAGCTGTACGCCGAGTGGTCGGAGGTCGT

GTCCACGAACTTCCGGGACGCCTCCGGGCCGGCCATGACCGAGATCGGCG

AGCAGCCGTGGGGGCGGGAGTTCGCCCTGCGCGACCCGGCCGGCAACTGC

GTGCACTTCGTGGCCGAGGAGCAGGACTGACACGTGCTACGAGATTTCGA

TTCCACCGCCGCCTTCTATGAAAGGTTGGGCTTCGGAATCGTTTTCCGGG

ACGCCGGCTGGATGATCCTCCAGCGCGGGGATCTCATGCTGGAGTTCTTC

GCCCACCCCAACTTGTTTATTGCAGCTTATAATGGTTACAAATAAAGCAA

TAGCATCACAAATTTCACAAATAAAGCATTTTTTTCACTGCATTCTAGTT

GTGGTTTGTCCAAACTCATCAATGTATCTTAAGGCCTTTTCCCCGTATCC

CCCCAGGTGTCTGCAGGCTCAAAGAGCAGCGAGAAGCGTTCAGAGGAAAG

CGATCCCGTGCCACCTTCCCCGTGCCCGGGCTGTCCCCGCACGCTGCCGG

CTCGGGGATGCGGGGGGAGCGCCGGACCGGAGCGGAGCCCCGGGCGGCTC

GCTGCTGCCCCCTAGCGGGGGAGGGACGTAATTACATCCCTGGGGCTTT

GGGGGGGGGCTGTCCCTCTAGAACTAGTGGATCCCCCGGGCTGCAGGAAT

TCGATAAAGTTTTGTTACTTTATAGAAGAAATTTTGAGTTTTTGTTTTT

TTTTAATAAATAAATAAACATAAATAAATTGTTTGTTGAATTTATTATTA

GTATGTAAGTGTAAATATAATAAAACTTAATATCTATTCAAATTAATAAA

TAAACCTCGATATACAGACCGATAAAACACATGCGTCAATTTTACGCATG

ATTATCTTTAACGTACGTCACAATATGATTATCTTTCTAGGGTTAATCTA

GCTGCGTGTTCTGCAGCGTGTCGAGCATCTTCATCTGCTCCATCACGCTG

TAAAACACATTTGCACCGCGAGTCTGCCCGTCCTCCACGGGTTCAAAAAC

GTGAATGAACGAGGCGCGCTCACTGGCCGTCGTTTTACAACGTCGTGACT

GGGAAAACCCTGGCGTTACCCAACTTAATCGCCTTGCAGCACATCCCCCT

TTCGCCAGCTGGCGTAATAGCGAAGAGGCCCGCACCGATCGCCCTTCCCA

ACAGTTGCGCAGCCTGAATGGCGAATGGGACGCGCCCTGTAGCGGCGCAT

TAAGCGCGGCGGGTGTGGTGGTTACGCGCAGCGTGACCGCTACACTTGCC

AGCGCCCTAGCGCCCGCTCCTTTCGCTTTCTTCCCTTCCTTTCTCGCCAC

GTTCGCCGGCTTTCCCCGTCAAGCTCTAAATCGGGGGCTCCCTTTAGGGT

TCCGATTTAGTGCTTTACGGCACCTCGACCCCAAAAAACTTGATTAGGGT

GATGGTTCACGTAGTGGGCCATCGCCCTGATAGACGGTTTTTCGCCCTTT

GACGTTGGAGTCCACGTTCTTTAATAGTGGACTCTTGTTCCAAACTGGAA

CAACACTCAACCCTATCTCGGTCTATTCTTTTGATTTATAAGGGATTTTG

CCGATTTCGGCCTATTGGTTAAAAAATGAGCTGATTTAACAAAAATTTAA

CGCGAATTTTAACAAAATATTAACGCTTACAATTTAGGTGGCACTTTTCG

GGGAAATGTGCGCGGAACCCCTATTTGTTTATTTTTCTAAATACATTCAA

ATATGTATCCGCTCATGAGACAATAACCCTGATAAATGCTTCAATAATAT

TGAAAAAGGAAGAGT
```

Single cell clones of HEK293T cells were isolated and suspension adapted for transfection of the packaging and transfer vector plasmids. To test and confirm the effect of PIGGYBAC® transposase, the transfection was performed in the absence or presence of PIGGYBAC® transposase mRNA. PEIpro transfection agent was used in the transfection.

To make a packaging cell line for lenti-eGFP, packaging plasmid and transfer vectors encoding eGFP were co-transfected. To make a packing cell line for packaging alone (i.e., no gene of interest expression), the packaging plasmid alone was transfected. Four days post-transfection, the stably transfected cells were selected by adding puromycin and Zeocin for the lenti-eGFP, and puromycin alone for the packaging cell line.

Results

Co-transfection of transposase mRNA significantly enhanced the antibiotic-resistant colonies, indicating that transposase expression indeed promoted the chromosomal integration of the expression cassettes. FIGS. 3A-3D show the results of HEK293T cells transfected with packaging and eGFP transfer vector in the absence (FIGS. 3A and 3C) or presence (FIGS. 3B and 3D) of transposase mRNA (TP mRNA). After 4 days post transfection, antibiotics-resistant cells were selected by adding puromycin (0.5 ug/mL) and Zeocin (300 ug/mL). At 26 days post-transfection, the cells were observed under the fluorescent microscope and images for GFP and black and white (B/W) were collected.

Similarly, co-transfection of transposase mRNA enhanced the antibiotic-resistant colonies during the process of packaging cell line generation (data now shown).

The antibiotic-resistant packaging cell line was amplified and frozen before characterization. The packaging cell encoding LV-eGFP was thawed and cultured in suspension in the presence of puromycin and Zeocin. To induce lentiviral vector production, sodium butyrate (6 mM) and doxycycline (2 ug/mL) were added to the packaging cell culture and further incubated.

Figure 4:
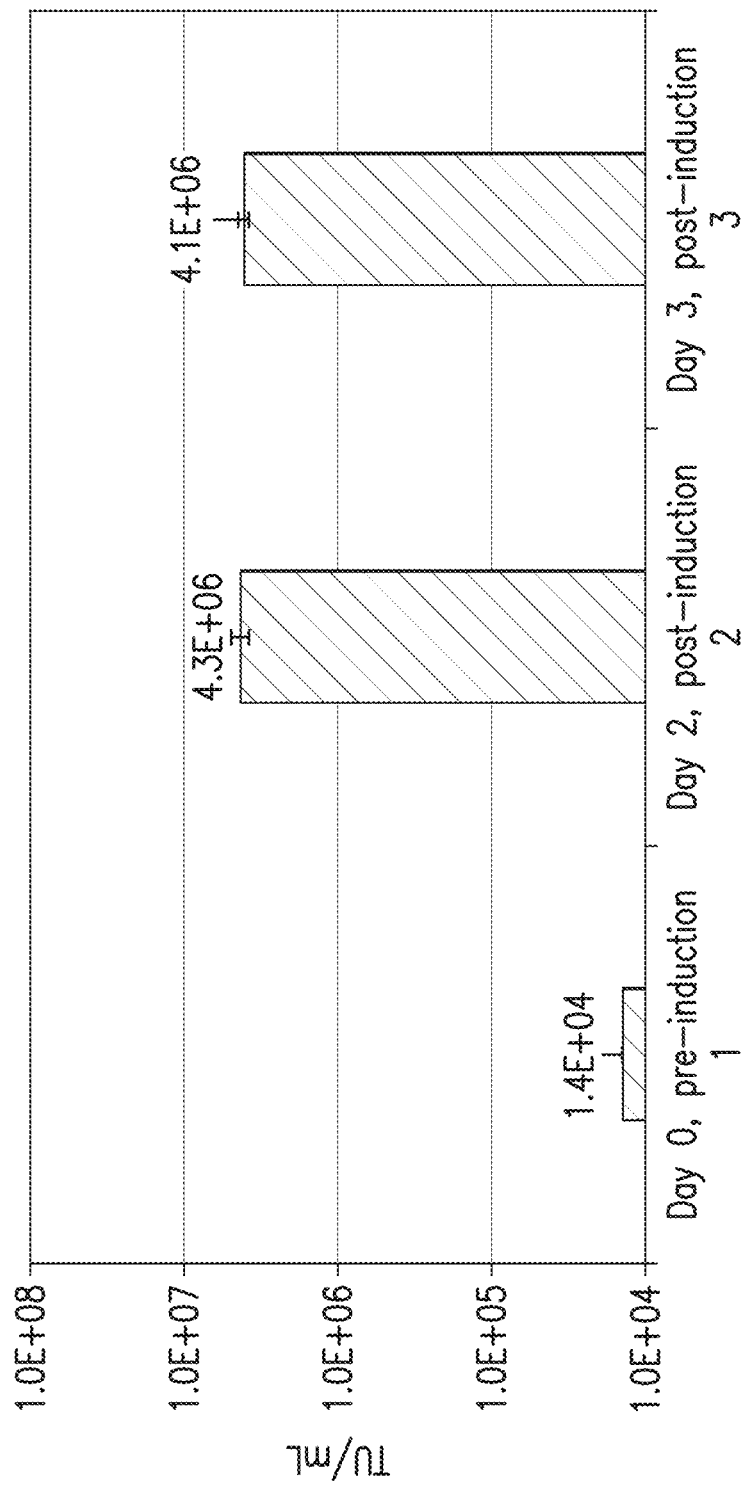
FIG. 4 shows the production of lentiviral vectors using exemplary cell lines described herein.

At day 2 and 3 post-induction, the culture supernatant was collected for the measurement of lentiviral titers. For the measurement of uninduced lentiviral vector titer, the culture supernatant of uninduced sample was used. It was observed that more than 4E6 transduction units/mL of lentiviral vector were produced upon induction (day 2 and day 3) while the basal amount of lentiviral vector production before any induction (day 0) was basal level (FIG. 4).

Example 2: Further Characterization of Lentiviral Producer Cell Line

Figure 5:
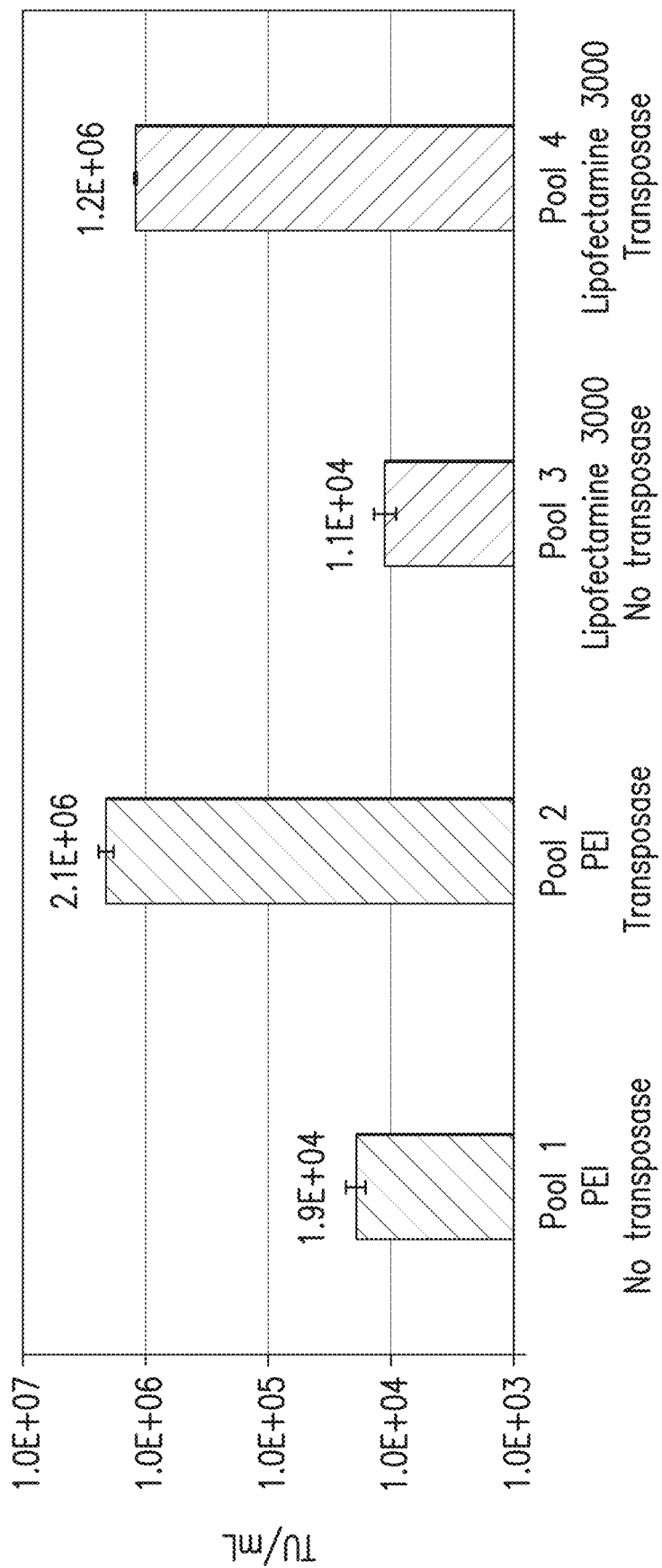
FIG. 5 shows lentivirus titer for PEI and lipofectamine transfection with and without transposase.

A. Additional studies were designed to examine the use of different transfection agents with the vectors described herein. As shown in FIG. 5 both PEI and lipofectamine 3000 successfully increased infectious lentivirus titers from the PCL pools by about 100 times in the presence of PIGGYBAC® transposase mRNA, demonstrating that the expression of the transposase leads to efficient integrations of cargo sequences into the chromosomes of the host cells.

B. Further experiments were conducted to determine the effects of removal of antibiotics on the success of lentiviral production. In such experiments, an HEK-293T, single cell clone (SCC) designated DH4 was selected for demonstrating consistent infectious titers upon induction up to passage 21.

Figure 6:
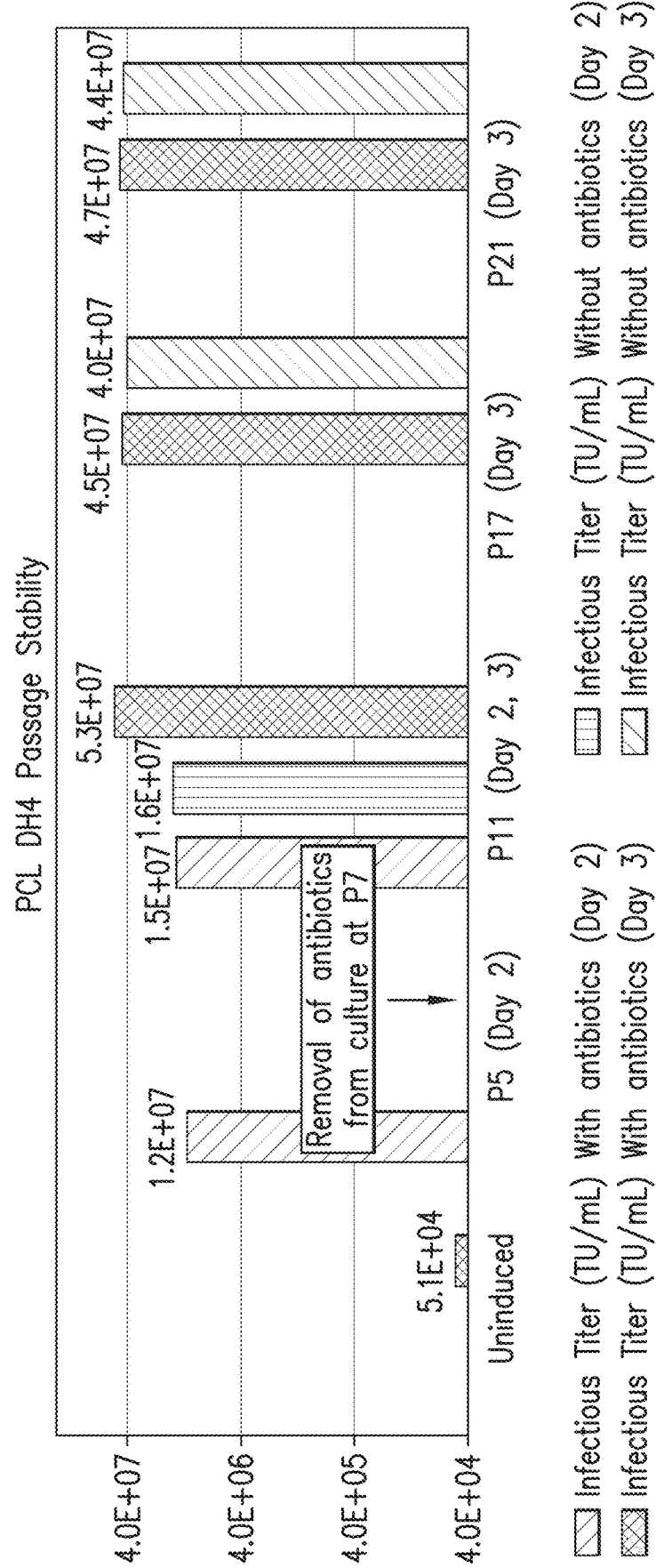
FIG. 6 shows lentivirus productivity and stability of a single cell clone DH4.

As demonstrated in FIG. 6, uninduced cells exhibited a low level of infectious titer. After passage 7 (day 2), the induced cells demonstrated 1.2E7 TU/mL (transduction units/mL). For a selection of the cells, antibiotics were removed, and the cells continued to be passed. At passage 11 (day 2, 3), cells with antibiotics achieved a titer of 1.5E7 TU/mL (day 2) and 5.3E7 TU/mL (day 3). In comparison without antibiotics, the infectious titer still reached 1.6E7

TU/mL on day 2. Extending out to passage 17 and passage 21 (about a seven week period), the viral titer continued to remain at the same level without antibiotics as in the presence of antibiotics (4.4E7). Day 2 vs. Day 3 refers to the days of incubation of the PCLs after induction and before harvest, comparing the effect of an additional day between induction and harvest.

Figure 7:
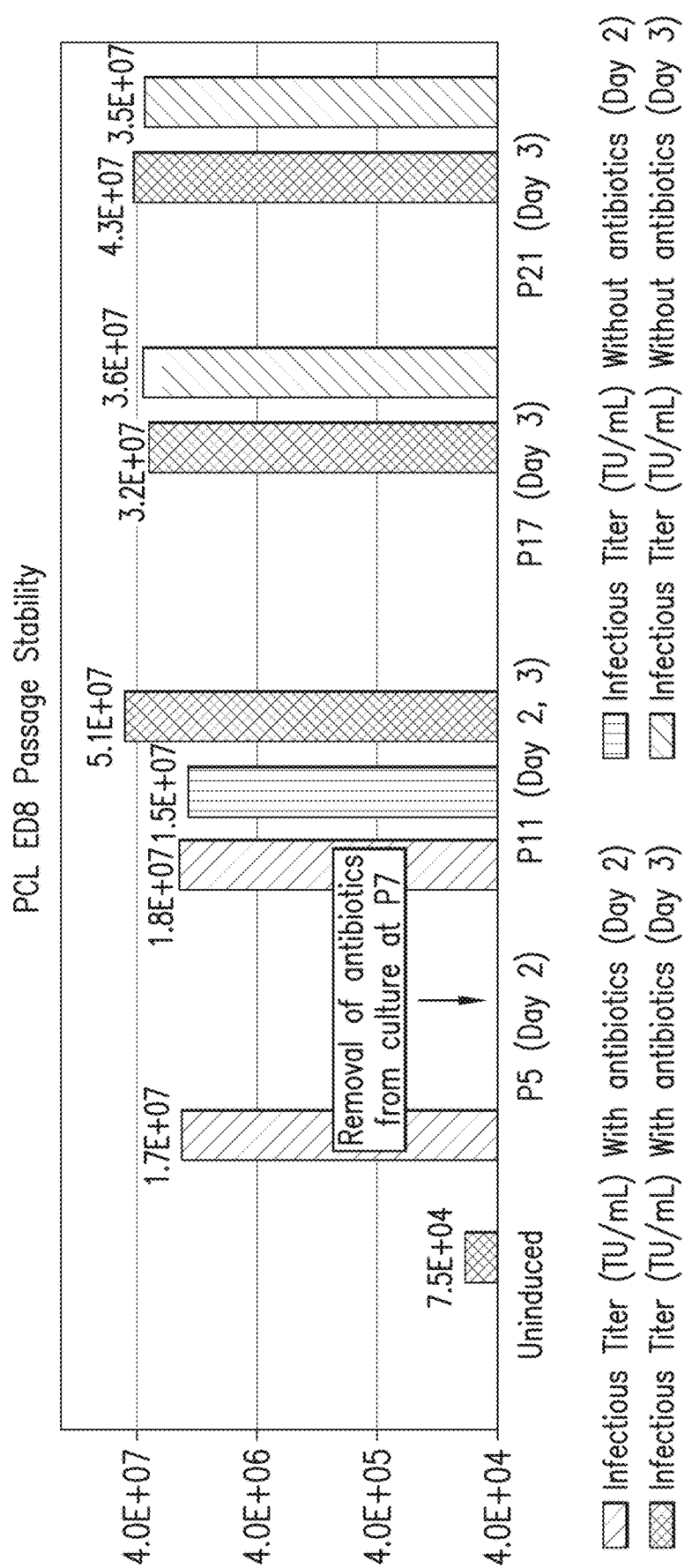
FIG. 7 shows lentivirus productivity and stability of a single cell clone ED8.

FIG. 7 shows similar results using another single cell clone, ED8. As with the DH4 clone, removal of antibiotics at passage 7 did not significantly impact the ability of the cell clone to produce an infectious viral titer of the same scale as cell treated with antibiotic. As noted, by passage 21, an infectious titer of 3.5E7 TU/mL was achieved, similar to the 4.3E7 TU/mL for the cells that were continued to be treated with antibiotics.

Figure 8:
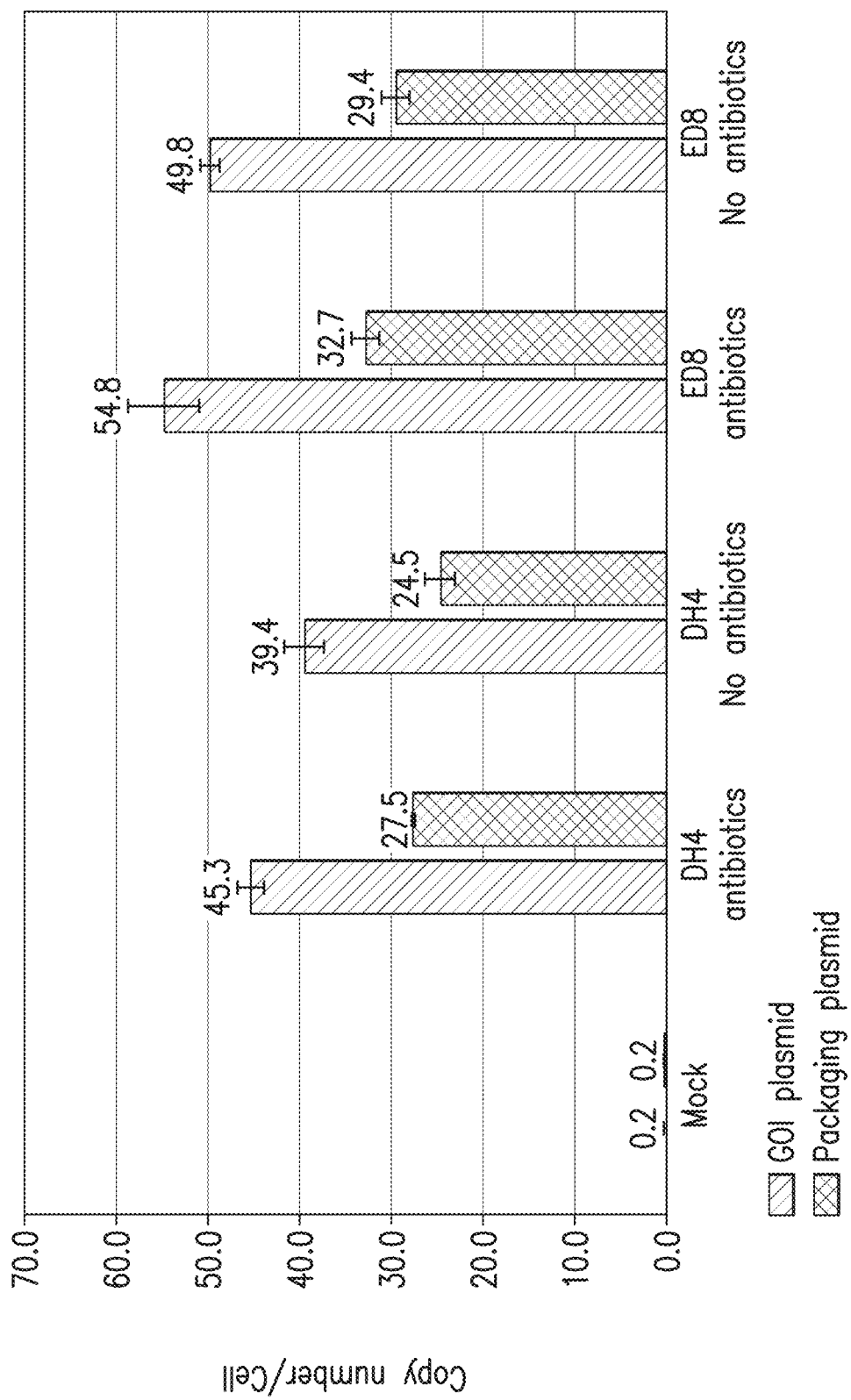
FIG. 8 shows the results of a copy number analysis.

FIG. 8 shows copy numbers (gene of interest or packaging plasmid) integrated into the host cell chromosomes measured using ddPCR assay. The vector copy number (VCN) was calculated by the formula, VCN=copy number of target sequence/copy number of RPP30 (Ribonuclease P/MRP Subunit P30)*2. The primers/probe sets specific to long terminal repeat (LTR) and vesicular stomatitis virus glycoprotein G (VSV-G) were used to detect the GOI and packaging plasmids, respectively. As noted for both cell clones, both the gene of interest and the packaging plasmid were efficiently integrated into the chromosomes of the cells. While the removal of antibiotics during the passage of the cells (again at passage 70) slightly reduced the copy number, there was still sufficient integration of the GOI and packaging plasmid into the cells.

This is a surprising and unexpected result, demonstrating that even in the absence of antibiotics, the producer cell lines prepared according to the methods described herein are able to produce high viral titer. This provides a significant advantage to the manufacturing of lentivirus, as it is highly desirable to remove antibiotics from a producer cell line culture to minimize risks associated with antibiotic contamination, etc., of a product that is to be later utilized in a human patient population.

C. Experiments were also conducted to determine the transduction efficiency of lentiviral vectors produced using the producer cell lines described herein, in comparison with lentivirus produced from transient transfection. Lentivirus was produced using PCL from both the DH4 and ED8 cell lines, along with transient transfection of an HEK-293 cell. Following production, lentiviral vectors were transduced into human peripheral blood mononuclear cells (PBMC) with a multiplicity of infection (MOI) of 5. Briefly, PMBCs were plated at 4E5 cells/well in a 24 well plate. On day 1, the cells were stimulated with IL-2 (15 ng/mL) and anti-CD3 and anti-CD-28 (25 µL/1E6 cells). The cells were then transduced with lentivirus at a multiplicity of infection of 5, using a green fluorescent protein as the gene of interest (GOI). After 5 days, the cells were analyzed using flow cytometry to determine the fraction of fluorescence-positive cells, and transduction efficiency was calculated.

Figure 9:
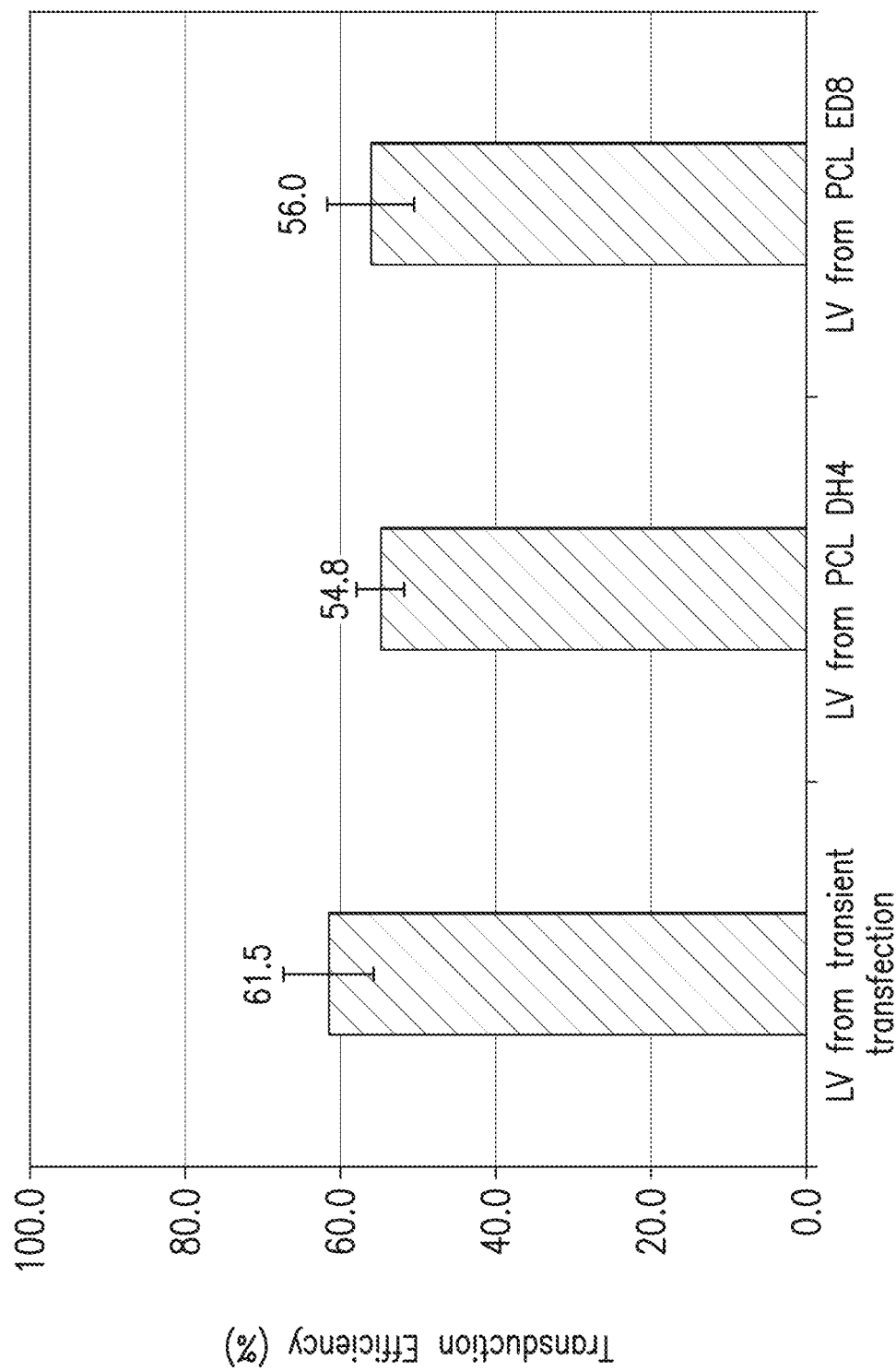
FIG. 9 shows potency comparison for lentivirus produced using transient transfection and producer cell lines.

As demonstrated in FIG. 9, when PMBCs are transduced with a multiplicity of infection of 5, similar transduction efficiency is observed for lentivirus produced using transient transfection methods, when compared with lentivirus produced using PCL (DH4 and ED8 lines) and the methods described herein (between about 55%-62% transduction efficiency).

It will be readily apparent to one of ordinary skill in the relevant arts that other suitable modifications and adaptations to the methods and applications described herein can be made without departing from the scope of any of the embodiments.

It is to be understood that while certain embodiments have been illustrated and described herein, the claims are not to be limited to the specific forms or arrangement of parts described and shown. In the specification, there have been disclosed illustrative embodiments and, although specific terms are employed, they are used in a generic and descriptive sense only and not for purposes of limitation. Modifications and variations of the embodiments are possible in light of the above teachings. It is therefore to be understood that the embodiments may be practiced otherwise than as specifically described.

All publications, patents and patent applications mentioned in this specification are herein incorporated by reference to the same extent as if each individual publication, patent or patent application was specifically and individually indicated to be incorporated by reference.

What is claimed is:

1. A method of producing a lentiviral vector-producing mammalian cell, comprising:
   a. transfecting a mammalian cell with:
      i. a packaging vector including an expression cassette, encoding:
         1. a lentiviral regulator of expression of virion proteins (REV) gene under control of a first promoter;
         2. a lentiviral envelope gene under control of a second promoter; and
         3. a lentiviral group specific antigen gag gene and a lentiviral polymerase pol gene both under control of a third promoter,
      wherein the expression cassette is flanked on both the 5' and 3' ends by transposon-specific inverted terminal repeats (ITR); and
      ii. a transfer vector, comprising:
         1. a nucleic acid sequence encoding a gene of interest under control of a fourth promoter,
      wherein the nucleic acid sequence is flanked on both the 5' and 3' ends by transposon-specific inverted terminal repeats (ITR);
   b. culturing the transfected mammalian cell; and
   c. isolating the lentiviral vector-producing mammalian cell.

2. The method of claim 1, wherein the mammalian cell is a mammalian cell culture.

3. The method of claim 2, wherein the mammalian cell culture is a suspension culture.

4. The method of claim 3, wherein the mammalian cell is an HEK293T cell.

5. The method of claim 1, wherein the gag gene is an HIV gag gene and the pol gene is an HIV pol gene.

6. The method of claim 1, wherein the lentiviral envelope gene is a Vesicular Stomatitis Virus Glycoprotein (VSV-G) gene.

7. The method of claim 1, wherein the first, second and third promoters are derepressible promoters.

8. The method of claim 7, wherein the expression cassette further encodes a repressor element of the first, second and third derepressible promoters.

9. The method of claim 8, wherein each of the derepressible promoters comprises a functional promoter and a tetracycline operator sequence (TetO), and the repressor element is a tetracycline repressor protein.

10. The method of claim 9, wherein the expression cassette further comprises a Kruppel-associated box sequence following a sequence encoding the tetracycline repressor protein.

11. The method of claim 1, wherein the transposon-specific ITRs are Lepidopteran transposon ITRs.

12. The method of claim 1, wherein the transfecting is in the presence of a transposase that recognizes the transposon-specific ITRs.

13. The method of claim 12, wherein the transposase is Lepidopteran transposase mRNA or Lepidopteran transpose cDNA.

14. The method of claim 1, wherein the gene of interest is a gene of therapeutic interest.

* * * * *